United States Patent
Hara et al.

(10) Patent No.: US 10,760,107 B2
(45) Date of Patent: Sep. 1, 2020

(54) TRANSFORMED FUNGUS HAVING ENHANCED ERGOTHIONEINE PRODUCTIVITY AND METHOD FOR PRODUCING ERGOTHIONEINE

(71) Applicant: KIKKOMAN CORPORATION, Noda-shi, Chiba (JP)

(72) Inventors: Seiichi Hara, Noda (JP); Keiko Kurosawa, Noda (JP); Keiichi Ichikawa, Noda (JP)

(73) Assignee: KIKKOMAN CORPORATION, Noda-Shi (JP)

( * ) Notice: Subject to any disclaimer, the term of this patent is extended or adjusted under 35 U.S.C. 154(b) by 0 days.

(21) Appl. No.: 15/533,215

(22) PCT Filed: Dec. 25, 2015

(86) PCT No.: PCT/JP2015/086301
§ 371 (c)(1),
(2) Date: Jun. 5, 2017

(87) PCT Pub. No.: WO2016/121285
PCT Pub. Date: Aug. 4, 2016

(65) Prior Publication Data
US 2017/0321235 A1 Nov. 9, 2017

(30) Foreign Application Priority Data

Jan. 30, 2015 (JP) .................................. 2015-017328
Aug. 7, 2015 (JP) .................................. 2015-157444

(51) Int. Cl.
| | |
|---|---|
| *C12N 9/10* | (2006.01) |
| *C12N 9/14* | (2006.01) |
| *C12P 13/04* | (2006.01) |
| *C12N 15/09* | (2006.01) |
| C12R 1/665 | (2006.01) |
| C12R 1/685 | (2006.01) |
| C12R 1/69 | (2006.01) |
| C12R 1/66 | (2006.01) |

(52) U.S. Cl.
CPC ............... *C12P 13/04* (2013.01); *C12N 9/10* (2013.01); *C12N 9/1007* (2013.01); *C12N 9/13* (2013.01); *C12N 15/09* (2013.01); *C12Y 201/01* (2013.01); *C12Y 208/01007* (2013.01); C12R 1/66 (2013.01); C12R 1/665 (2013.01); C12R 1/685 (2013.01); C12R 1/69 (2013.01)

(58) Field of Classification Search
CPC ... C12N 9/14; C12N 9/10; C12N 9/13; C12N 9/1007; C12P 17/10; C12P 13/04; C12Y 201/01; C12Y 208/01007
USPC .............. 435/252.3, 254.4; 530/330
See application file for complete search history.

(56) References Cited

FOREIGN PATENT DOCUMENTS

| | | |
|---|---|---|
| JP | 2005-176602 A | 7/2005 |
| JP | 4865083 B1 | 2/2012 |
| JP | 5231025 B2 | 7/2013 |
| WO | WO 2014/100752 A1 | 6/2014 |
| WO | WO 2017/026173 A1 | 2/2017 |

OTHER PUBLICATIONS

Davos et al., Proteins: Structure, Function and Genetics, 2000, vol. 41: 98-107.*
Wristlock et al., Quarterly Reviews of Biophysics 2003, vol. 36 (3): 307-340.*
Kwiatkowski et al., Biochemistry 38:11643-11650, 1999.*
Kisselev L., Structure, 2002, vol. 10: 8-9.*
Su et al.( Adv in Appld Microbiol 2012, 81, pp. 1-61, abstract enclosed.*
Hynes et al. J. Genet. 1996, 75, pp. 297-311.*
International Preliminary Report on Patentability and Written Opinion and English translation dated Aug. 10, 2017, in PCT International Application No. PCT/JP2015/086301.
Bello et al., "The Neurospora crassa mutant NcΔEgt-1 identifies an ergothioneine biosynthetic gene and demonstrates that ergothioneine enhances conidial survival and protects against peroxide toxicity during conidial germination", Fungal Genet. Biol., 2012, vol. 49, pp. 160-172, ISSN 1087-1845.
Database GenBank, [online], Jun. 4, 2011, accession No. BAE60470, [retrieval date Feb. 25, 2016], Internet <URL:http://www.ncbi.nlm.nih.gov/protein/BAE60470.1>, Features, Origin.
Database GenBank, [online], Jun. 18, 2012, accession No. EIT76462, [retrieval date Feb. 25, 2016], Internet <URL:http://www.ncbi.nlm.nih.gov/protein/EIT76462.1>, Features, Origin.
Database GenBank, [online], Jun. 18, 2012, accession No. EIT79021, [retrieval dated Feb. 25, 2016], Internet <URL:http://www.ncbi.nlm.nih.gov/protein/ EIT79021.1>, Features, Origin.
Database GenBank, [online], May 16, 2014, accession No. KDE85407, [retrieval dated Feb. 25, 2016], Internet <URL:http://www.ncbi.nlm.nih.gov/protein/KDE85407.1>, Features, Origin.

(Continued)

*Primary Examiner* — Robert B Mondesi
*Assistant Examiner* — Mohammad Y Meah
(74) *Attorney, Agent, or Firm* — Birch, Stewart, Kolasch & Birch, LLP

(57) ABSTRACT

The purpose of the present invention is to provide an organism having an ergothioneine productivity that is capable of easily producing ergothioneine within a short period of time at a high yield, as compared with a conventional technology, and, therefore, enables ergothioneine production on an industrial scale. This purpose can be achieved by a transformed fungus into which a gene encoding enzyme (1) or genes encoding enzymes (1) and (2) have been inserted and in which the inserted gene(s) are overexpressed. (1) an enzyme catalyzing a reaction of synthesizing hercynyl cysteine sulfoxide from histidine and cysteine in the presence of S-adenosyl methionine, iron (II) and oxygen. (2) An enzyme catalyzing a reaction of synthesizing ergothioneine from hercynyl cysteine sulfoxide using pyridoxal 5'-phosphate as a coenzyme.

9 Claims, 7 Drawing Sheets
Specification includes a Sequence Listing.

(56) References Cited

OTHER PUBLICATIONS

Database GenBank, [online], Oct. 12, 2011, accession No. EHA24811, [retrieval date Feb. 25, 2016], Internet <URL:http://www.ncbi.nlm.nih.gov/protein/EHA24811.1>, Features, Origin.
Genghof, "Biosynthesis of Ergothioneine and Hercynine by Fungi and Actinomycetales", J. Bacteriol., 1970, vol. 103, No. 2, pp. 475-478, Print ISSN 0021-9193, Online ISSN 1098-5530, p. 475, right column, 13th line from the bottom to p. 476, left column, line 8.
Hu et al., "Bioinformatic and Biochemical Characterizations of C—S Bond Formation and Cleavage Enzymes in the Fungus Neurospora crassa Ergothioneine Biosynthetic Pathway", Organic Letters, 2014, vol. 16, pp. 5382-5385.
International Search Report, issued in PCT/JP2015/086301, dated Mar. 8, 2016.
Melville et al., "Ergothioneine in Microorganisms", J. Biol. Chem., 1956, vol. 223, pp. 9-17, Print ISSN 0021-9258, Online ISSN 1083-351X, p. 9, line 12 to p. 10, 5th line from the bottom.
Pluskal et al., "Genetic and Metabolomic Dissection of the Ergothioneine and Selenoneine Biosynthetic Pathway in the Fission Yeast, S. pombe, and Construction of an Overproduction System", PLoS One, 2014, vol. 9, No. 5, e97774, pp. 1-12, ISSN 1932-6203, fig. 1, 4, table 2.
Vit et al., "Ergothioneine Biosynthetic Methyltransferase EgtD Reveals the Structural Basis of Aromatic Amino Acid Betaine Biosynthesis", Chembiochem, 2015, vol. 16, pp. 119-125, Online ISSN 1439-7633. p. 119, left column, lines 1 to 2.
Written Opinion of the International Searching Authority, issued in PCTUP2015/086301, dated Mar. 8, 2016.
Extended European Search Report for European Application No. 15880177.9, dated May 25, 2018.
Office Action issued in European Application No. 15880177.9 dated Jan. 20, 2020.
Chinese Office Action and Search Report, dated Feb. 26, 2020, for Chinese Application No. 201580074637.8 with an English translation of the Chinese Office Action.
[Aspergillus oryzae], NCBI Reference Sequence: XP_001821768.1, Mar. 11, 2008, 1 page.
[Aspergillus oryzae], NCBI Reference Sequence: XP_001824907.1, Mar. 1, 2008, 1 page.
Chinese Office Action issued in Application No. 20150074637.8, dated Jul. 2, 2020, with English translation.
N-methyltransferase [Aspergillus nigerCBS 513.88], NCBI Reference Sequence: XP_001397117.2, Mar. 3, 2011, 1 page.

* cited by examiner

[FIG.1]
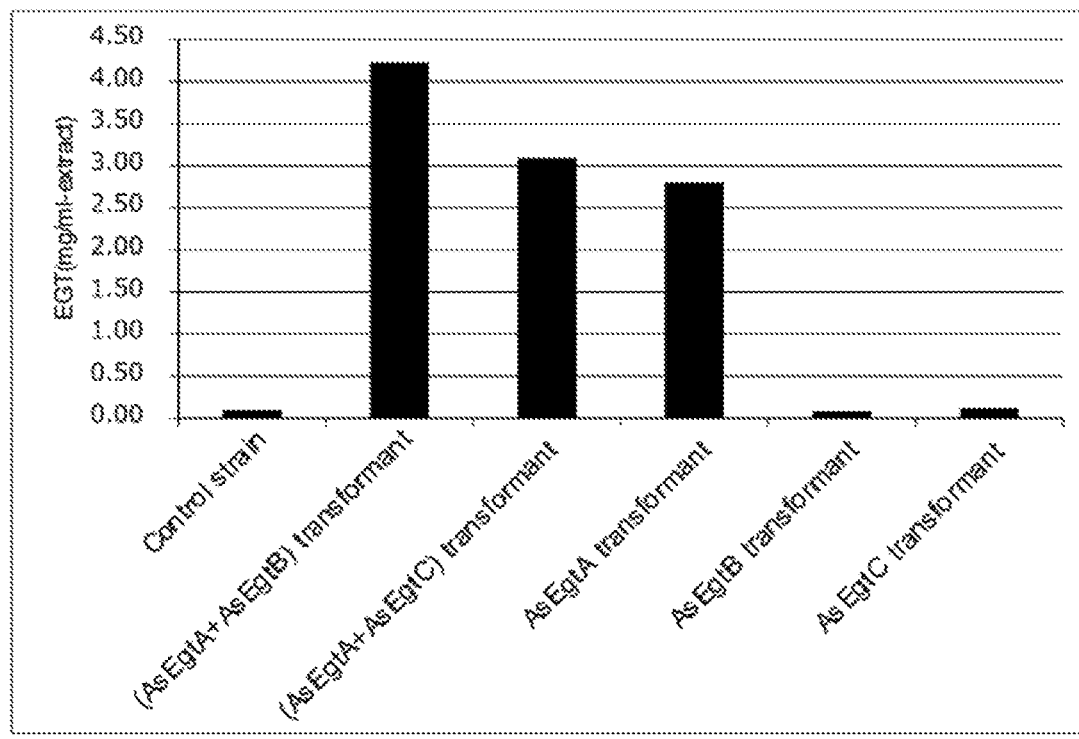

[FIG. 2]
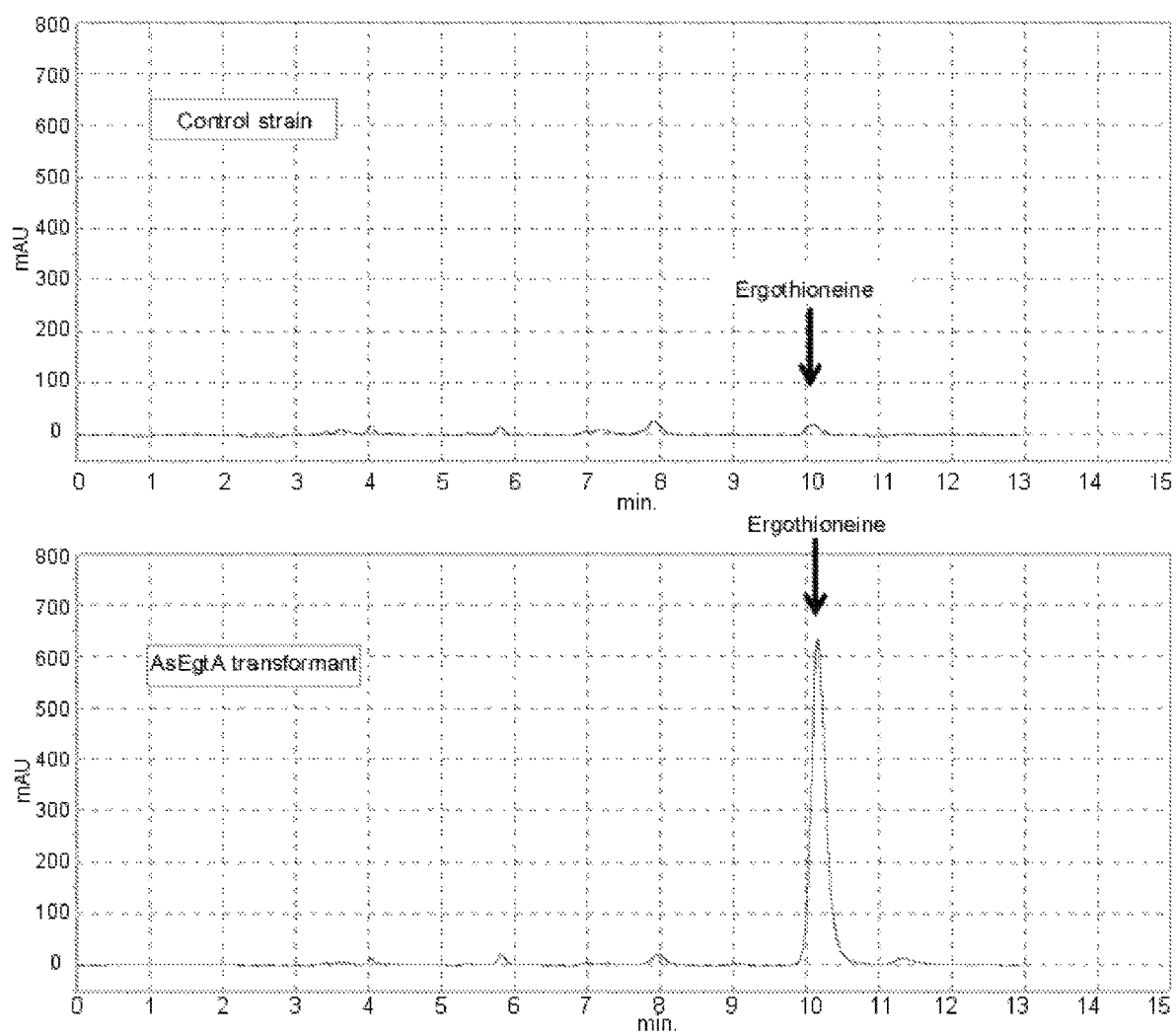

[FIG.3]
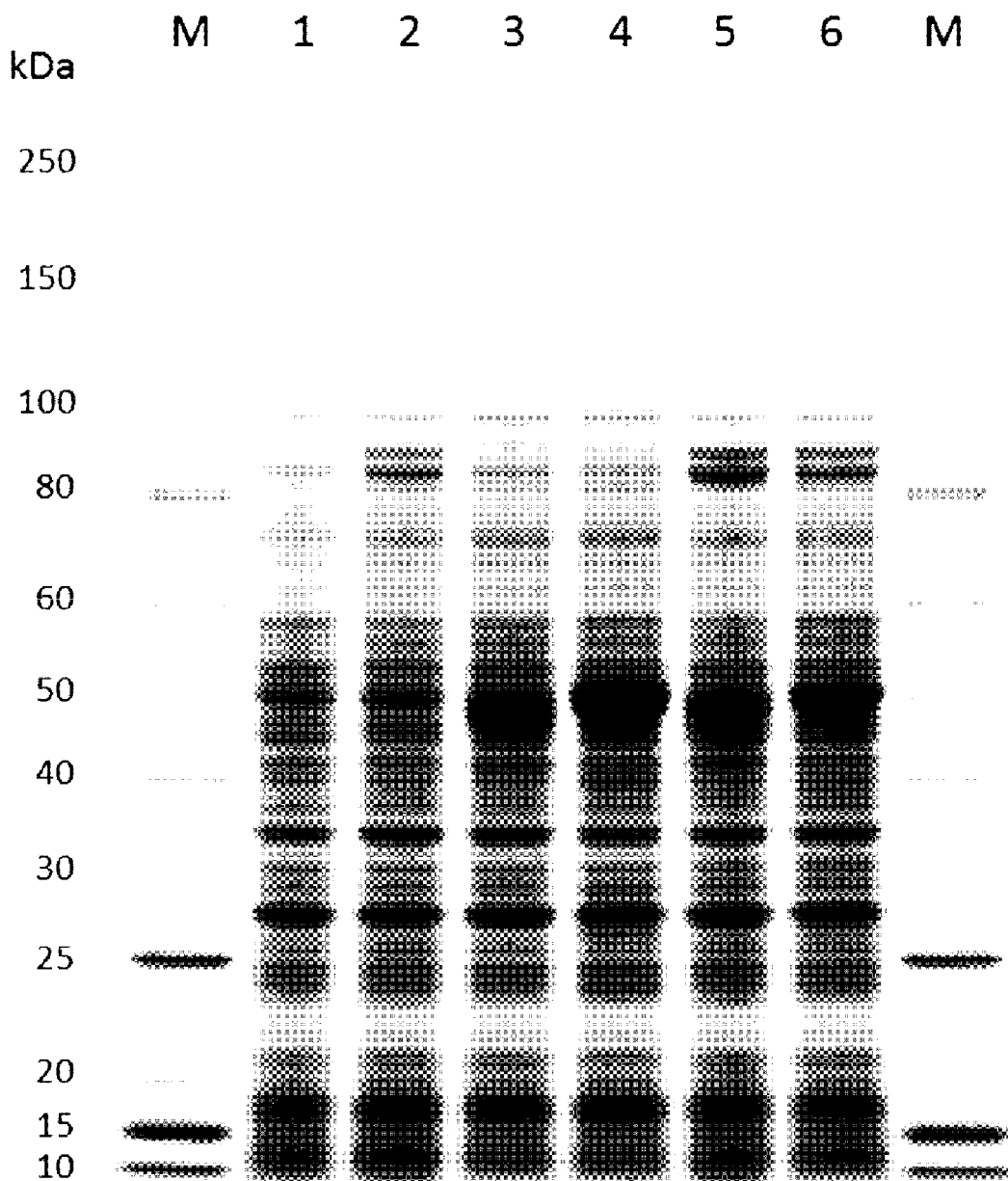

[FIG. 4]
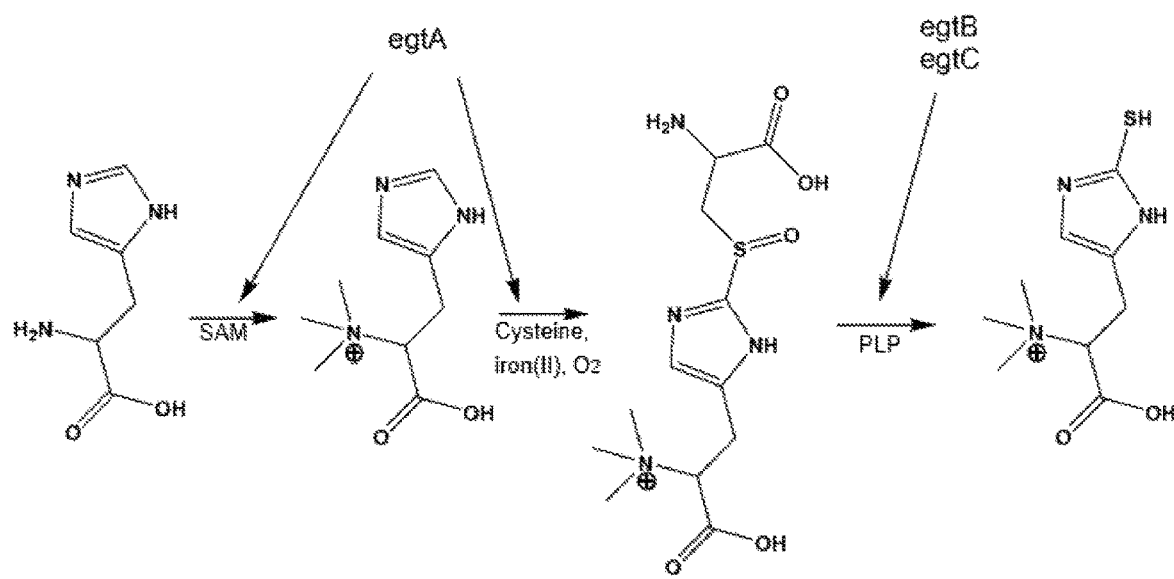
| Fungus | egtA | egtB | egtC |
|---|---|---|---|
| Aspergillus sojae | AsEgtA | AsEgtB | AsEgtC |
| Neurospora crassa | NCU04343 | NCU04636 | NCU11365 |
| Schizosaccharomyces pombe | SPBC1604.01 | SPBC21D10.11c | SPBC660.12c |

[FIG.5]
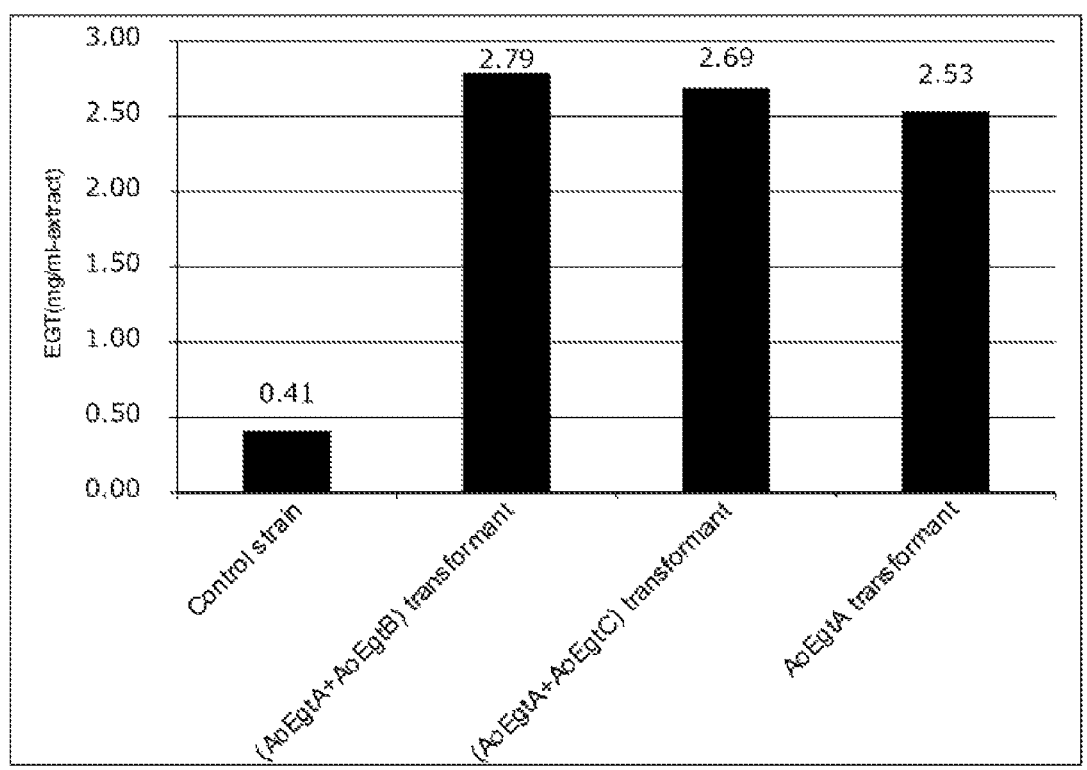

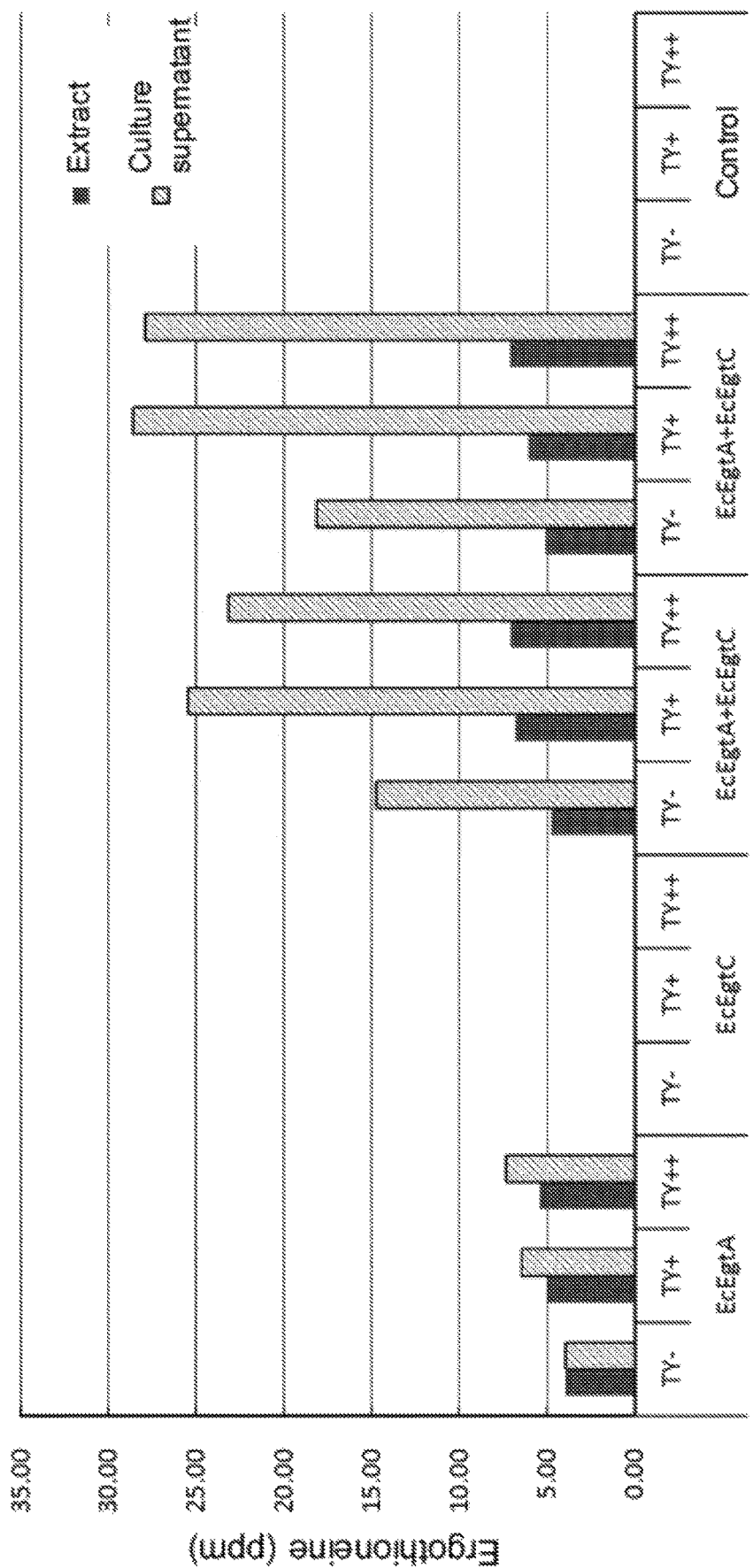
[FIG. 6]

[FIG.7]
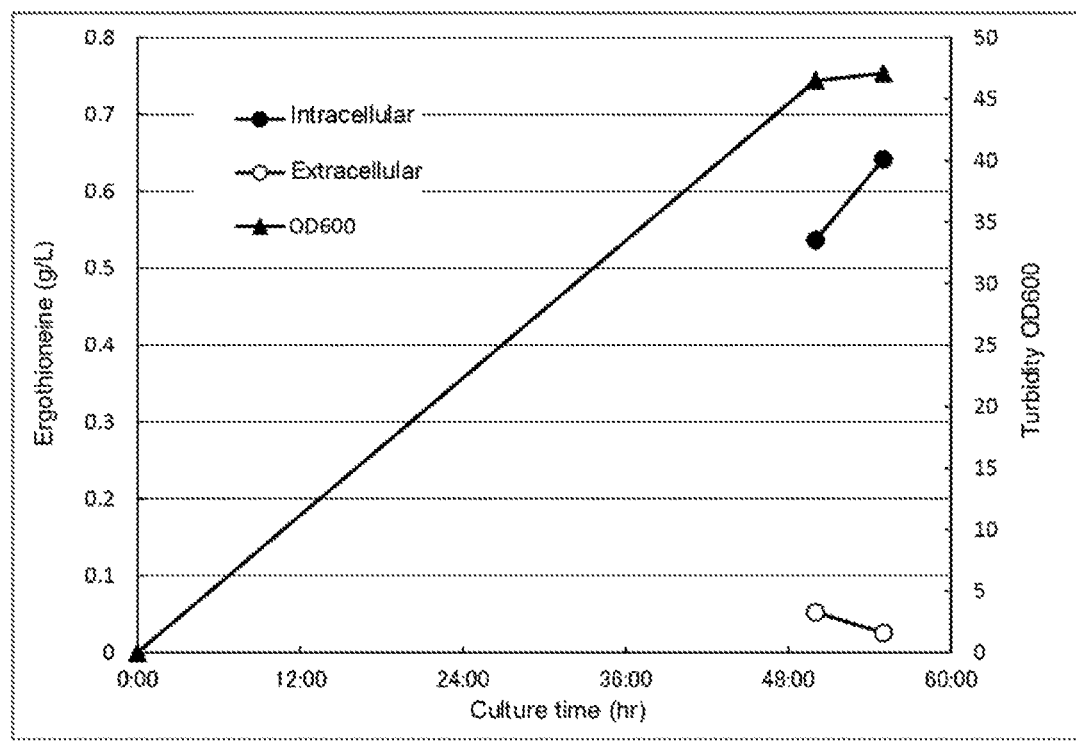

TRANSFORMED FUNGUS HAVING ENHANCED ERGOTHIONEINE PRODUCTIVITY AND METHOD FOR PRODUCING ERGOTHIONEINE

CROSS-REFERENCE TO RELATED APPLICATION

The present application claims the benefit of priority to Japanese Unexamined Patent Application Publication No. 2015-17328 filed on Jan. 30, 2015 and Japanese Patent Application No. 2015-157444 filed on Aug. 7, 2015, the disclosure of each of which is incorporated herein by reference in its entirety.

TECHNICAL FIELD

The present invention relates to a fungus capable of producing ergothioneine, as well as to a production method of ergothioneine utilizing such fungus.

BACKGROUND ART

Ergothioneine is a sulfur-containing amino acid represented by the following formula (II):

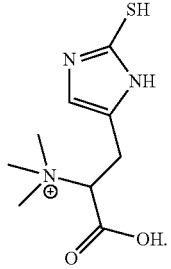

[Formula (II)]

It is a biological compound known to exist in the liver and other organs as well as in the blood of animals, including humans.

Ergothioneine is known to have antioxidative activity. For example, it is said to have an ability to scavenge hydroxyl radicals, an ability to suppress the iron- or copper-dependent generation of hydroxyl radicals from hydrogen peroxide, an ability to suppress copper-dependent oxidation of oxyhemoglobin, and an ability to suppress oxidation of arachidonic acid by myoglobin and hydrogen peroxide. Ergothioneine is also said to show inhibition of elastase activity, inhibition of tyrosinase activity, anti-inflammatory activity, enhancement of cell energy, anti-stress activity, anti-aging activity, anti-wrinkle activity, and suppression of lipid peroxide generation.

Due to its characteristics as a functional biological compound having various physiological activities and as a heat-resistant, water-soluble material, ergothioneine is expected to find applications in functional food products, supplements, cosmetic products, pharmaceutical products, quasi-pharmaceutical products, animal feed, and the like.

Known production methods of ergothioneine include, in addition to extraction from the organs or blood of animals, extraction from mycelium of mushrooms capable of producing ergothioneine (See, Patent Documents 1 and 2 below, the entire disclosure of each of which is incorporated herein by reference). Non-Patent Documents 1 and 2 below (the entire disclosure of each of which is incorporated herein by reference) state that most bacteria lack the ability to produce ergothioneine. These documents also state that certain fungi such as *Aspergillus niger* and *Neurospora crassa* are capable of producing ergothioneine whereas *Saccharomyces cerevisiae* has little ability to produce ergothioneine.

Ergothioneine biosynthesis system have been reported in some fungi capable of producing ergothioneine. For example, Non-Patent Documents 3 and 4 below (the entire disclosure of each of which is incorporated herein by reference) describe the biosynthesis system of ergothioneine in *Neurospora crassa*, while Non-Patent Document 5 below (the entire disclosure of which is incorporated herein by reference) describes the biosynthesis system of ergothioneine in *Schizosaccharomyces pombe*, a "fission yeast".

PRIOR ART DOCUMENTS

Patent Documents

Patent Document 1: Japanese Patent Laid-Open Publication No. 4865083

Patent Document 2: Japanese Patent Laid-Open Publication No. 5231025

Non-Patent Documents

Non-Patent Document 1: Donald B. Melville et al, J. Biol. Chem. 1956, 223:9-17

Non-Patent Document 2: Dorothy S. Genghof, J. Bacteriology, August 1970, p. 475-478

Non-Patent Document 3: Fungal Genet Biol 49 (2012) 160-172

Non-Patent Document 4: Org Lett. 2014 Oct. 17; 16(20): 5382-5385

Non-Patent Document 5: PLoS One 2014 May 14; 9(5): e97774

DISCLOSURE OF THE INVENTION

Problems to be Solved by the Invention

The technique described in Patent Documents 1 and 2, which involves culturing mycelium of certain mushrooms and subsequently extracting ergothioneine, is unsuitable for producing ergothioneine on an industrial scale since culturing the mycelium of mushrooms requires significant skills and takes long time.

The description of Non-Patent Documents 1 to 5 suggests that ergothioneine can be biosynthesized by some fungi other than mushrooms. Of these, Non-Patent Document 3 describes a transformed *Neurospora crassa*, which has been transformed by the deletion of a gene (NCU04343) encoding an enzyme (NcEgt-1) that catalyzes the reaction in which —$NH_2$ group of histidine is methylated to form hercynine, which in turn is used with cysteine to form hercynyl cysteine sulfoxide represented by the following formula (I):

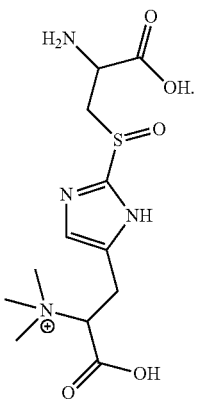

[Formula (I)]

Non-Patent Documents 3 and 4 describe enzymes NCU04636 and NCU11365 that can possibly catalyze the reaction in which ergothioneine is formed from hercynyl cysteine sulfoxide. Non-Patent Document 4 further states that ergothioneine was formed from hercynyl cysteine sulfoxide by an in vitro reaction using the NCU11365 gene extracted from a transformed *E. coli* overexpressing NCU11365.

However, Non-Patent Documents 3 and 4 mention nothing about the in vivo production of ergothioneine using transformants overexpressing the NCU04343, NCU04636 or NCU11365 gene.

Non-Patent Document 5 states that ergothioneine was synthesized in vivo by using a transformed *Schizosaccharomyces pombe* overexpressing the SPBC1604.01 gene that encodes an enzyme corresponding to the above-described NcEgt-1. However, ergothioneine was obtained only in extremely small amounts by using the transformed *Schizosaccharomyces pombe* described in Non-Patent Document 5. Also, nothing is mentioned in Non-Patent Document 5 about transformants that can overexpress a gene corresponding to the aforementioned NCU11365 gene.

Accordingly, it is an objective of the present invention to provide an organism having an ability to produce ergothioneine that can produce ergothioneine at a higher yield, yet in a simpler manner and in a shorter period of time, as compared to the mycelium of mushrooms as described in Patent Documents 1 and 2 and can thus enable the industrial-scale production of ergothioneine. It is also an objective of the present invention to provide a method for producing a high-purity-ergothioneine-containing composition by using the organism.

Means of Solving the Problems

In the course of extensive studies to find solutions to the above-described problems, the present inventors have succeeded in identifying, from a fungus *Aspergillus sojae*, the gene AsEgtA encoding an enzyme that catalyzes a reaction to produce hercynyl cysteine sulfoxide from histidine and cysteine and the genes AsEgtB and AsEgtC each encoding an enzyme that catalyzes a reaction to produce ergothioneine from hercynyl cysteine sulfoxide.

Subsequently, the present inventors prepared DNA constructs designed to overexpress each of the isolated genes and introduced the constructs into *Aspergillus sojae* to transform it, thereby succeeded in creating an *Aspergillus sojae* transformant that can overexpress AsEgtA, AsEgtB or AsEgtC; an *Aspergillus sojae* transformant that can overexpress AsEgtA and AsEgtB; and an *Aspergillus sojae* transformant that can overexpress AsEgtA and AsEgtC.

The present inventors then subjected these *Aspergillus sojae* transformants to various tests and surprisingly found that the transformant overexpressing AsEgtA tend to have an enhanced ability to produce ergothioneine as compared to the wild-type strain, whereas the transformant overexpressing AsEgtB or AsEgtC does not show such tendency.

Even surprisingly, the present inventors have found that, contrary to the above-described finding, the transformant overexpressing AsEgtA and AsEgtB and the transformant overexpressing AsEgtA and AsEgtC tend to have an increased ability to produce ergothioneine as compared to the transformant overexpressing AsEgtA alone. This suggests that the transformants overexpressing the two genes involved in the biosynthesis of ergothioneine has an enhanced ability to produce ergothioneine that has been increased multiplicatively, rather than additively.

It was also found that the transformants overexpressing one or two of the above-described genes involved in the biosynthesis of ergothioneine could be cultured according to the standard method; they were not substantially different from the wild-type strain in terms of their growth rate and other characteristics. It is these successful examples and findings that ultimately led to the completion of the present invention.

According to the present invention, there is provided a transformed filamentous fungus that has a gene encoding an enzyme described in (1) below or genes encoding enzymes described in (1) and (2) below inserted therein and can overexpress the inserted gene or genes:

(1) an enzyme that catalyzes the reaction in which hercynyl cysteine sulfoxide is produced from histidine and cysteine in the presence of S-adenosylmethionine, iron (II), and oxygen; and (2) an enzyme that catalyzes the reaction in which ergothioneine is produced from hercynyl cysteine sulfoxide using pyridoxal 5'-phosphate as a coenzyme.

In the transformed filamentous fungus of the present invention, the filamentous fungus is preferably a microorganism of the genus *Aspergillus*.

In the transformed filamentous fungus of the present invention, the filamentous fungus is preferably a fungus of the genus *Aspergillus* selected from the group consisting of *Aspergillus sojae*, *Aspergillus oryzae*, *Aspergillus niger*, *Aspergillus tamarii*, *Aspergillus awamori*, *Aspergillus usamii*, *Aspergillus kawachii*, and *Aspergillus saitoi*.

Preferably, the transformed filamentous fungus of the present invention is a transformed filamentous fungus in which the expression of the gene encoding the enzyme (1) or the genes encoding the enzymes (1) and (2) is enhanced such that the amount of ergothioneine is increased compared to a host filamentous fungus.

Preferably, the transformed filamentous fungus of the present invention is a transformed filamentous fungus in which the expression of the genes encoding the enzymes (1) and (2) is enhanced such that the amount of ergothioneine is increased compared to transformed filamentous fungi in which the expression of the gene encoding the enzyme (1) is enhanced.

Preferably, the transformed filamentous fungus of the present invention is a transformed filamentous fungus in which the expression of the gene encoding the enzyme (1) or the genes encoding the enzymes (1) and (2) is enhanced such that when the transformed filamentous fungi is cultured at 30° C. for 3 days in a culture medium suitable for the growth of the host filamentous fungus, the amount of ergothioneine is 10.0 mg or more per 1 g of dry cell mass.

In the transformed filamentous fungus of the present invention, the gene encoding the enzyme (1) is a gene selected from the group consisting of a gene having a base sequence of SEQ ID NO: 1, a gene having a base sequence of SEQ ID NO: 23, and a gene having a base sequence of SEQ ID NO: 33 in the sequence listing, or the enzyme (1) is an enzyme selected from the group consisting of an enzyme having an amino acid sequence of SEQ ID NO: 4, an enzyme having an amino acid sequence of SEQ ID NO: 26, and an enzyme having an amino acid sequence of SEQ ID NO: 34 in the sequence listing.

In the transformed filamentous fungus of the present invention, the gene encoding the enzyme (1) is a gene selected from the group consisting of a gene having a base sequence of SEQ ID NO: 1, a gene having a base sequence of SEQ ID NO: 23, and a gene having a base sequence of SEQ ID NO: 33 in the sequence listing, or the enzyme (1) is an enzyme selected from the group consisting of an enzyme having an amino acid sequence of SEQ ID NO: 4, an enzyme having an amino acid sequence of SEQ ID NO: 26, and an enzyme having an amino acid sequence of SEQ ID NO: 34 in the sequence listing.

According to another aspect of the present invention, there is provided a method for producing a high-purity-ergothioneine-containing composition, comprising the step of culturing a transformed filamentous fungus in a culture medium suitable for the growth of the host filamentous fungus to obtain a culture, from which an ergothioneine-containing composition having purity of 5% or higher is obtained.

According to another aspect of the present invention, there is provided a recombinant vector comprising at least one gene selected from the group consisting of a gene encoding the enzyme (1) and a gene encoding the enzyme (2), and a heterologous gene.

According to another aspect of the present invention, there is provided a composition comprising a recombinant vector containing a gene encoding the enzyme (1) and a heterologous gene, and a recombinant vector containing a gene encoding the enzyme (2) and a heterologous gene.

In the recombinant vector and the composition of the present invention, the gene encoding the enzyme (1) and the gene encoding the enzyme (2) are each a gene either originating from a host organism to insert the recombinant vector therein or optimized to be expressed in the host organism.

According to another aspect of the present invention, there is provided a transformed *Escherichia coli* having a gene encoding the enzyme (1) or genes encoding the enzymes (1) and (2) inserted therein and overexpressing the inserted gene or genes.

Advantageous Effects of Invention

According to the transformed filamentous fungus or the production method of the present invention, ergothioneine can be produced at high amounts and at high purities using conditions used to culture common filamentous fungi. As a result, the present invention enables the production of ergothioneine in a simpler manner and in a shorter period of time as compared to the conventional mushrooms having an ability to produce ergothioneine or the conventional production method of ergothioneine using such mushrooms. Thus, according to the present invention, industrial-scale production of ergothioneine can be achieved.

BRIEF DESCRIPTION OF DRAWINGS

FIG. 1 is a diagram showing the results of deteuaining the amounts of ergothioneine produced by the transformed *Aspergillus sojae* and the control strain as described in Examples. In the figure, EGT stands for ergothioneine.

FIG. 2 shows HPLC charts of ergothioneine extracts obtained from the control strain and the AsEgtA transformant as described in Examples.

FIG. 3 is a photographic representation of SDS-PAGE performed with the total protein extracted from the transformants and the control strain as described in Examples. Lane 1 corresponds to the total protein derived from the control strain, Lane 2 corresponds to the total protein derived from the AsEgtA transformant, Lane 3 corresponds to the total protein derived from the AsEgtB transformant, Lane 4 corresponds to the total protein derived from the AsEgtC transformant, Lane 5 corresponds to the total protein derived from the (AsEgtA+AsEgtB) transformant, and Lane 6 corresponds to the total protein derived from the (AsEgtA+AsEgtC) transformant.

FIG. 4 is a schematic diagram showing the ergothioneine biosynthesis system of fungi. In the figure, SAM stands for S-adenosylmethionine and PLP stands for pyridoxal 5'-phosphate.

FIG. 5 is a diagram showing the results of determining the amounts of ergothioneine produced by the transformed *Aspergillus oryzae* and the control strain as described in Examples. In the figure, EGT stands for ergothioneine.

FIG. 6 is a diagram showing the results of determining the amounts of ergothioneine produced by the transformed *E. coli* and the control strain as described in Examples.

FIG. 7 is a diagram showing the results of culturing the transformed *E. coli* and the results of determining the amounts of ergothioneine produced by the transformed *E. coli* as described in Examples. In the figure, "intracellular" indicates the results of quantification of ergothioneine in the ergothioneine extract and "extracellular" indicates the results of quantification of ergothioneine in the culture supernatant.

DESCRIPTION OF EMBODIMENTS

The present invention will now be described in details.
(Overview of Transformed Filamentous Fungus of the Present Invention)

The transformed fungus of the present invention has a gene encoding an enzyme described in (1) below or genes encoding enzymes (1) and (2) described below inserted therein and can overexpress the inserted gene or genes:

(1) an enzyme that catalyzes the reaction in which hercynyl cysteine sulfoxide is produced from histidine and cysteine in the presence of S-adenosylmethionine, iron (II), and oxygen; and (2) an enzyme that catalyzes the reaction in which ergothioneine is produced from hercynyl cysteine sulfoxide using pyridoxal 5'-phosphate as a coenzyme.

The transformed filamentous fungus of the present invention can ultimately produce ergothioneine from histidine and cysteine by overexpressing a gene that is inserted as a foreign gene and encodes the enzymes described in (1) and (2) above (hereinafter, referred to as enzyme (1) and enzyme (2), respectively). The transformed filamentous fungi of the present invention are generally divided into two categories:

those that overexpress the gene encoding the enzyme (1) but not the gene encoding the enzyme (2) and those that overexpress both the gene encoding the enzyme (1) and the gene encoding the enzyme (2). It should be understood that the gene encoding the enzyme (1) to be overexpressed and the gene encoding the enzyme (2) to be overexpressed may individually include one or more genes.

FIG. 4 shows a schematic diagram of the supposed biosynthesis system of fungi. The enzyme (1) corresponds to egtA and the enzyme (2) corresponds to egtB or egtC in FIG. 4.

(Enzymological Properties of Enzymes (1) and (2))

As shown in FIG. 4, the enzyme (1) has SAM-dependent methyltransferase activity; that is, it can catalyzes the reaction in which histidine is converted to hercynine with a trimethylated $NH_2$ group in an S-adenosylmethionine (SAM)-dependent manner. The enzyme (1) also has sulfatase activity; that is, it can catalyze the reaction in which hercynyl cysteine sulfoxide as shown in the following formula (I) is produced from hercynine and cysteine in the presence of iron (II) and oxygen:

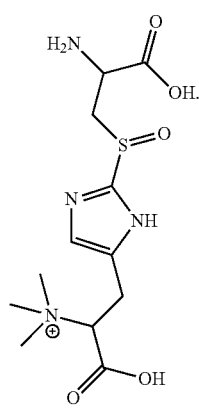

[Formula (I)]

As a result of these activities, the enzyme (1) can produce hercynyl cysteine sulfoxide from histidine and cysteine in the presence of S-adenosylmethionine, iron (II) and oxygen.

The enzyme (2) has PLP-binding cysteine desulfurase activity; that is, it can catalyze the reaction in which ergothioneine is produced from hercynyl cysteine sulfoxide using pyridoxal 5'-phosphate (PLP) as a coenzyme.

Capable of expressing the genes encoding the enzyme (1) or the enzymes (1) and (2), the transformed filamentous fungus of the present invention can produce ergothioneine from histidine and cysteine under the conditions that the individual enzymes are activated.

(The Structural Properties of Enzymes (1) and (2))

The enzyme (1) may be any enzyme that has the above-described enzymological properties; that is, any enzyme that has the SAM-dependent methyltransferase activity and the sulfatase activity such that it can catalyze the reaction in which hercynyl cysteine sulfoxide is produced from histidine and cysteine in the presence of S-adenosylmethionine, iron (II) and oxygen, and is not particularly limited by its structural properties, such as amino acid sequence, entire or partial three-dimensional structure, and molecular weight; biochemical properties, such as optimum pH, optimum temperature, and denaturing conditions; type of the organism from which it originates; or other conditions. However, since the enzyme (1) has both the SAM-dependent methyl-transferase activity and the sulfatase activity, it is preferred that the enzyme contains well-conserved domains of both SAM-dependent methyltransferases and sulfatases.

An example of the conserved domain of SAM-dependent methyltransferases is a SAM-dependent methyltransferase domain containing a DUF2260 domain. An example of the conserved domain of sulfatases is a formylglycine-generating enzyme (FGE)-sulfatase domain. The above-described domains may not necessarily be connected in tandem; for example, a nonconserved domain may be present between the two domains. The enzyme (1) preferably contains a DinB_2 domain between the conserved domain of SAM-dependent methyltransferase and the conserved domain of sulfatase. If present, the DinB_2 domain preferably contains $HX_3HXE$, an iron-binding motif.

For example, one embodiment of the enzyme (1) has a structure that contains a conserved domain of SAM-dependent methyltransferase, a DinB_2 domain, and a conserved domain of sulfatase. Another embodiment of the enzyme (1) has a structure that contains a SAM-dependent methyltransferase domain containing a DUF2260 domain, a DinB_2 domain containing $HX_3HXE$, and an FGE-sulfatase domain.

One preferred embodiment of the enzyme (1) is one that has 30% or higher, preferably 40% or higher, more preferably 45% or higher sequence identity to NcEgt-1 (NCU04343) described in Non-Patent Document 3. As used herein, the term "sequence identity" refers to the identity between the two sequences aligned to each other and does not refer to the similarity between the two sequences.

Specific examples of the enzyme (1) include, but are not limited to, proteins assigned the following accession numbers (the numbers in the parentheses indicate sequence identities obtained by Blastp using a AsEgtA protein of SEQ ID NO: 4 as a query sequence): XP_001727309.1 (97%), XP_002375556.1 (97%), XP_001211614.1 (74%), GAA90479.1 (75%), XP_001261027.1 (72%), XP_001275843.1 (72%), EDP55069.1 (72%), XP_755900.1 (72%), EHA24811.1 (74%), XP_001397117.2 (73%), EYE96655.1 (72%), CAK42541.1 (71%), XP_680889.1 (69%), EPS32723.1 (66%), GAD91762.1 (63%), EKV06018.1 (63%), XP_002487159.1 (61%), XP_002145387.1 (61%), CDM31097.1 (62%), XP_002623045.1 (57%), EQL36096.1 (57%), EEQ91012.1 (57%), XP_002794316.1 (57%), XP_002540839.1 (57%), XP_001246505.1 (57%), XP_003066681.1 (56%), EFW18329.1 (56%), EEH06820.1 (56%), XP_003172803.1 (55%), EGE82230.1 (56%), EGD95426.1 (54%), EZF30391.1 (54%), EHY53149.1 (53%), XP_002844140.1 (54%), XP_003237555.1 (54%), EXJ78765.1 (52%), XP_001543980.1 (53%), EXJ84167.1 (53%), EXJ76804.1 (51%), ETI21425.1 (52%), EXJ55868.1 (52%), EKG13377.1 (51%), XP_003836988.1 (51%), EON60831.1 (50%), EGE08446.1 (52%), EMD86163.1 (51%), EUN21814.1 (51%), EMD69895.1 (50%), EME40669.1 (52%), EUC45427.1 (51%), EEH18365.1 (52%), XP_001939537.1 (51%), EUC28327.1 (50%), XP_003296645.1 (50%), EER38486.1 (54%), XP_007587632.1 (50%), E0A87110.1 (50%), EEH47303.1 (54%), EMC91772.1 (51%), EJT79063.1 (50%), XP_007289878.1 (51%), EMF09308.1 (50%), XP_007274188.1 (49%), XP_003849540.1 (51%), ENH83409.1 (50%), EQB47754.1 (48%), XP_006693510.1 (51%), ETN41916.1 (50%), XP_003711933.1 (49%), EWG46299.1 (50%), EGU87412.1 (49%), ESZ95365.1 (48%), EGC47631.1 (52%), EXM31381.1 (49%), EXL83373.1 (49%), XP_385823.1 (50%), EMT70054.1 (50%), EXK95313.1 (49%), CCT71860.1 (50%), EXM04867.1 (49%), EXA38531.1 (49%), EWZ34577.1 (49%), EWY87102.1 (49%), ENH70585.1 (49%), EYB29661.1 (50%), EXK37219.1 (49%), EWZ95323.1 (49%), EGY20613.1 (49%), EME78671.1 (50%), EKJ73623.1 (50%), EFQ30701.1 (48%), EPE09977.1 (48%), EXV06624.1 (49%), ERS99852.1 (49%), EG059462.1 (49%), XP_003348780.1 (48%), EFY99927.1 (49%), XP_007594915.1 (47%), XP_003660752.1 (49%), EAA27088.3 (49%), ERF68279.1 (49%), EFX04429.1 (50%), ETR98676.1 (49%), EFY84340.1 (48%), XP_006968620.1 (48%), XP_003048884.1 (49%), EHK20832.1 (49%), EPE24413.1 (49%), EJP62962.1 (49%), ETS83740.1 (48%), EHK45989.1 (49%), ELQ64904.1 (47%), XP_006672555.1 (48%), ELQ40007.1 (46%), EXL83375.1 (50%), EXK95315.1 (50%), CCE33591.1 (48%), EXM04869.1 (51%), EXA38533.1 (50%), EWZ95325.1 (50%), EXK37221.1 (50%), EWZ34579.1 (50%), EWY87104.1 (50%), CCX31754.1 (47%), XP_956324.2 (46%), and XP_956324.2 (46%).

Of the above-listed proteins, the protein with accession number XP_001727309.1 (97%) is a protein having an amino acid sequence of SEQ ID NO: 26. Also, the protein with accession number XP_001397117.2 (73%) is a protein having an amino acid sequence of SEQ ID NO: 34. These results suggest that methyltransferases (or putative methyltransferases or hypothetical proteins) having an amino acid sequence with 40% or higher, preferably 50% or higher, more preferably 70% or higher sequence identity to the amino acid sequence of the AsEgtA protein may be used as the enzyme (1).

The enzyme (2) may also be any enzyme that has the above-described enzymological properties; that is, any enzyme that has the PLP-binding cysteine desulfurase activity such that it can catalyze the reaction in which ergothioneine is produced from hercynyl cysteine sulfoxide using pyridoxal 5'-phosphate (PLP) as a coenzyme, and is not particularly limited by its structural properties, biochemical properties, type of the organism from which it originates, or other conditions. However, since the enzyme (2) has the PLP-binding cysteine desulfurase activity, it is preferred that the enzyme contain conserved domains of PLP-binding cysteine desulfurases.

The enzyme (2) may include at least two types of structurally different enzymes: those containing a PLP-binding cysteine desulfurase domain with approximately 75% sequence identity to NCU04636 described in Non-Patent Document 3 and those containing a PLP-binding cysteine desulfurase domain with approximately 44% sequence identity to NCU11365 described in Non-Patent Document 4. The enzyme (2) may comprise one of the two types or both.

(Amino Acid Sequences of Enzymes (1) and (2))

The enzymes (1) and (2) may have any amino acid sequence as long as the resulting enzyme has the above-described enzymological properties, or preferably, the above-described enzymological properties and structural properties. For example, one embodiment of the enzyme (1) having the above-described enzymological and structural properties includes the amino acid sequence of SEQ ID NO: 4, and one embodiment of the enzyme (2) having the above-described enzymological and structural properties includes the amino acid sequences of SEQ ID NOs: 5 and 6. The enzymes having an amino acid sequence of SEQ ID NOs: 4 to 6 each originate from *Aspergillus sojae* and are named by the present inventors as AsEgtA, AsEgtB, and AsEgtC proteins, respectively. The base sequences of the genes encoding these enzymes are given in SEQ ID NOs: 1 to 3.

Likewise, one embodiment of the enzyme (1) having the above-described enzymological and structural properties includes the amino acid sequences of SEQ ID NOs: 26 and 34. The enzymes having an amino acid sequence of SEQ ID NOs: 26 and 34 originate from *Aspergillus oryzae* and *Aspergillus niger*, respectively, and are named by the present inventors as AoEgtA protein and AnEgtA protein, respectively. The base sequences of the genes encoding these enzymes are given in SEQ ID NOs: 23 and 33, respectively. One embodiment of the enzyme (2) having the above-described enzymological and structural properties includes the amino acid sequences of SEQ ID NOs: 27 and 28. The enzymes having an amino acid sequence of SEQ ID NOs: 27 and 28 each originate from *Aspergillus oryzae* and are named by the present inventors as AoEgtB protein and AoEgtC protein, respectively. The base sequences of the genes encoding these enzymes are given in SEQ ID NOs: 24 and 25, respectively.

AsEgtA, AsEgtB and AsEgtC are encoded by genes encoding these enzymes present on the chromosomal DNA of *Aspergillus sojae*. The AoEgtA, AoEgtB and AoEgtC proteins are encoded by genes encoding these enzymes present on the chromosomal DNA of *Aspergillus oryzae*. The AnEgtA protein is encoded by a gene encoding the enzyme present on the chromosomal DNA of *Aspergillus niger*. The genes present on the chromosomal DNA of the organisms of origin and the proteins and the enzymes encoded by such genes may be referred to as "wild-type genes," "wild-type proteins" and "wild-type enzymes," herein.

The amino acid sequence of the enzymes (1) and (2) may be any amino acid sequence resulting from deletion, substitution, addition or other modification of one to several amino acids in the amino acid sequence of the wild type enzyme as long as the resulting enzyme has the above-described enzymological properties. As used herein, the range specified by the phrase "one to several" as in "deletion, substitution or addition of one to several amino acids" in the amino acid sequence is not particularly limited but specifically refers to 1, 2, 3, 4, 5, 6, 7, 8, 9, 10, 11, 12, 13, 14, 15, 16, 17, 18, 19, or 20 amino acids, preferably 1, 2, 3, 4, 5, 6, 7, 8, 9, or 10 or so amino acids, more preferably 1, 2, 3, 4, or 5 or so amino acids. As used herein, the term "deletion of amino acids" means that amino acid residues are lost or eliminated from the sequence. The term "substitution of amino acids" means that amino acid residues are replaced with other amino acid residues. The term "addition of amino acids" means that new amino acid residues are added to the sequence by inserting them into the sequence.

Specific embodiments of "deletion, substitution or addition of one to several amino acids" include embodiments in which one to several amino acids are replaced with other chemically similar amino acids. For example, a hydrophobic amino acid may be substituted with another hydrophobic amino acid, or a polar amino acid may be substituted with another polar amino acid having the same charge. Such chemically similar amino acids are known in the art for each amino acid. Specific examples of non-polar (hydrophobic) amino acids include alanine, valine, isoleucine, leucine, proline, tryptophan, phenylalanine, and methionine. Examples of polar (neutral) amino acids include glycine, serine, threonine, tyrosine, glutamine, aspargine, and cysteine. Examples of positively charged basic amino acids include arginine, histidine, and lysine. Examples of negatively charged acidic amino acids include aspartic acid, and glutamic acid.

Examples of the amino acid sequences resulting from deletion, substitution, addition or other modification of one to several amino acids in the amino acid sequence of the wild-type enzyme include amino acid sequences having a particular percentage or higher sequence identity to the amino acid sequence of the wild-type enzyme, such as amino acid sequences having 80% or higher, preferably 85% or higher, more preferably 90% or higher, 91% or higher, 92% or higher, 93% or higher, 94% or higher, 95% or higher, 96% or higher, 97% or higher, 98% or higher, or 99% or higher, still more preferably 99.5% or higher sequence identity to the amino acid sequence of the wild-type enzyme.

(Genes Encoding Enzymes (1) and (2))

The genes encoding the enzymes (1) and (2) may have any base sequence as long as such a base sequence encodes an amino acid sequence of an enzyme that has the above-described enzymological properties, or preferably, the above-described enzymological properties and structural properties. The genes encoding the enzymes (1) and (2) are overexpressed in the transformed filamentous fungus to produce the enzyme (1) and (2). As used herein, the term "expression of a gene" means that the enzyme encoded by a gene is produced via transcription and translation in a form that exhibits its inherent catalytic activities. As used herein, the term "overexpression of a gene" means that the protein (enzyme) encoded by an inserted gene is produced at a level exceeding the normal expression level of the protein in the host organism.

The genes encoding the enzymes (1) and (2) may be a gene that can produce the enzymes (1) and (2) via splicing after the gene introduced into the host organism is transcribed, or alternatively, it may be a gene that can produce enzymes (1) and (2) without requiring splicing after the transcription of the gene.

The genes encoding the enzymes (1) and (2) may not be completely identical to the inherent gene (i.e., wild-type gene) of the organism of origin: it may be any DNA fragment with a base sequence that hybridizes to the base sequence complementary to the base sequence of the wild-type gene under stringent conditions as long as the gene encodes an enzyme having at least the above-described enzymological properties.

As used herein, "the base sequence that hybridizes under stringent conditions" refers to a DNA base sequence obtained by colony hybridization, plaque hybridization, southern blot hybridization and other suitable hybridization techniques using a DNA fragment having the base sequence of the wild-type gene as a probe.

As used herein, the term "stringent condition" refers to a condition under which the signals from specific hybrids can be clearly distinguished from the signals from non-specific hybrids and may vary depending on the hybridization system used, type of the probe, and the sequence and its length. Such conditions may be determined by varying the hybridization temperature or by varying the washing temperature and the salt concentration. For example, if even the signals from non-specific hybrids are strongly detected, the specificity can be increased by increasing the temperature for the hybridization and the washing temperature and if necessary, by decreasing the salt concentration for the washing. In contrast, if even the signals from specific hybrids are not detected, the hybrids may be stabilized by decreasing the temperature for the hybridization and the washing and if necessary, by increasing the salt concentration for the washing.

A specific example of the stringent condition involves using a DNA probe as a probe and carrying out the hybridization overnight (approximately 8 to 16 hours) using 5×SSC, 1.0 (w/v) % blocking reagent for nucleic acid hybridization (Boehringer Mannheim), 0.1 (w/v) % N-lauroylsarcosine, and 0.02 (w/v) % SDS. The washing may be performed twice for 15 min each, using 0.1 to 0.5×SSC and 0.1 (w/v) % SDS, preferably 0.1×SSC and 0.1 (w/v) % SDS. The temperature to carry out the hybridization and the washing is 65° C. or higher, preferably 68° C. or higher.

Examples of the DNA having a base sequence that hybridizes under stringent conditions include DNA having the base sequence of the wild-type gene originating from a colony or plaque; DNA obtained by carrying out hybridization under stringent conditions using a filter on which fragments of the DNA are immobilized; and DNA identified by carrying out hybridization at 40 to 75° C. in the presence of 0.5 to 2.0 M NaCl, preferably at 65° C. in the presence of 0.7 to 1.0 M NaCl, and subsequently washing the filter at 65° C. using 0.1 to 1×SSC solution (a 1×SSC solution contains 150 mM sodium chloride and 15 mM sodium citrate). The preparation of the probe and the hybridization can be performed according to the procedures described in textbooks such as Molecular Cloning: A laboratory Manual, 2nd-Ed., Cold Spring Harbor Laboratory, Cold Spring Harbor, N.Y., 1989, Current Protocols in Molecular Biology, Supplement 1-38, John Wiley & Sons, 1987-1997 (These literature will be referred to as reference literature, hereinafter. The entire disclosure of reference literature is incorporated herein by reference). Those skilled in the art would adequately determine the conditions for obtaining DNA having a base sequence that hybridizes to the base sequence complementary to the base sequence of the wild-type gene under stringent conditions by considering, in addition to the above-mentioned conditions such as the salt concentration of buffers and the temperature, other conditions such as the probe concentrations, probe lengths, and the reaction time.

Examples of the DNA having a base sequence that hybridizes under stringent conditions include a DNA having a particular percentage or higher sequence identity to the base sequence of the DNA used as a probe having the base sequence of the wild-type gene, such as DNA having 80% or higher, preferably 85% or higher, more preferably 90% or higher, 91% or higher, 92% or higher, 93% or higher, 94% or higher, 95% or higher, 96% or higher, 97% or higher, 98% or higher, or 99% or higher, still more preferably 99.5% or higher sequence identity to the base sequence of the wild-type gene.

Examples of the base sequence that hybridizes to a base sequence complimentary to the base sequence of the wild-type gene under stringent conditions include base sequences resulting from deletion, substitution, addition or other modification of from 1 to several, preferably from 1 to 50, more preferably from 1 to 30, even more preferably from 1 to 20, still even more preferably 1, 2, 3, 4, 5, 6, 7, 8, 9 or 10 bases in the base sequence of the wild-type gene. As used herein, the term "deletion of a base" means that a base is lost or eliminated from the sequence. The term "substitution of a base" means that abase is replaced with another base. The term "addition of a base" means that a new base is added to the sequence by inserting it into the sequence.

While the enzyme encoded by a base sequence that hybridizes to abase sequence complementary to the base sequence of the wild-type gene under stringent conditions should be an enzyme having an amino acid sequence resulting from deletion, substitution, addition or other modification of 1 to several amino acids in the amino acid sequence of the enzyme encoded by the base sequence of the wild-type gene, it has the same enzymatic activities as the enzyme encoded by the base sequence of the wild-type gene.

(Means for Calculating Sequence Identity)

While the sequence identity between base sequences or amino acid sequences may be determined by any method, it can be determined by using a commonly known method, whereby a wild-type gene or an amino acid sequence of an enzyme encoded by the wild-type gene is aligned with a base sequence or amino acid sequence of interest and the percent match between the two sequences is calculated using a program.

The algorithm of Karlin and Altschul is a known program for calculating the percent match between two amino acid sequences or base sequences (Proc. Natl. Acad. Sci. USA 87: 2264-2268, 1990; Proc. Natl. Acad. Sci. USA 90: 5873-5877, 1993). Using this algorithm, Altschul et al. developed the BLAST program (J. Mol. Biol. 215: 403-410, 1990). The Gapped BLAST program, which can determine the sequence identity in a more sensitive way than the BLAST, is also known (Nucleic Acids Res. 25: 3389-3402, 1997). Using the above-described programs, one skilled in the art can search in a database for a sequence with a high sequence identity to a given sequence. These programs are available on the website of U.S. National Center for Biotechnology Information (http://blast.ncbi.nlm.nih.gov/Blast.cgi).

While the above-described methods are commonly used in the search of sequences with certain sequence identities from a database, Genetyx network model, version 12.0.1 (Genetyx corporation) may also be used in a homology analysis to determine the sequence identity of individual sequences. This method is based on the Lipman-Pearson method (Science 227:1435-1441, 1985). When analyzing the sequence identity of base sequences, regions encoding proteins (CDS or ORF) are used when possible.

(Origins of Genes Encoding Enzymes (1) and (2))

The genes encoding the enzymes (1) and (2) are derived from species having the ability to produce ergothioneine or species expressing the enzymes (1) and (2). Examples of the organisms of origin from which the genes encoding the enzymes (1) and (2) are derived include microorganisms. Of various microorganisms, filamentous fungi are preferred since many of their species are known to have the ability to produce ergothioneine. Examples of the filamentous fungi include fungi of the genus *Aspergillus*. Specific examples include *Aspergillus sojae*, *Aspergillus oryzae*, *Aspergillus niger*, *Aspergillus tamarii*, *Aspergillus awamori*, *Aspergillus usamii*, *Aspergillus kawachii*, and *Aspergillus saitoi*.

*Aspergillus sojae*, *Aspergillus oryzae*, *Aspergillus niger*, *Aspergillus tamarii*, *Aspergillus awamori*, *Aspergillus usamii*, *Aspergillus kawachii*, and *Aspergillus saitoi* listed above as specific examples of the filamentous fungi of the genus *Aspergillus* have long been used in the production of miso paste, soy sauce, Japanese sake, shochu liquor and other fermented products, as well as in the production of citric acid and enzymes such as amylases. Their high enzyme productivity and high reliability for the safety, backed by a long history of use, make these microorganisms highly useful in industrial applications.

As described above, while the organisms of origin from which the enzymes (1) and (2) are derived are not particularly limited, the enzymes (1) and (2) expressed in the transformed filamentous fungus might not be deactivated by the growth conditions of the host filamentous fungus or the enzymes might show their respective activities. For this reason, it is preferred that the organism of origin from which the genes encoding the enzymes (1) and (2) are derived be a host filamentous fungus to be transformed by the insertion of the genes encoding the enzymes (1) and (2) or a filamentous fungus that grows under conditions similar to the growth conditions of the host filamentous fungus.

(Cloning of Genes Encoding Enzymes (1) and (2) Using Genetic Engineering Technique)

The genes encoding the enzymes (1) and (2) can be inserted into various suitable known vectors. The resulting vector can then be introduced into a suitable known host organism to create a transformant in which the recombinant vector (recombinant DNA) containing the genes encoding enzymes (1) and (2) has been introduced. A person skilled in the art can appropriately select a suitable method for obtaining the genes encoding the enzymes (1) and (2), a method for obtaining the gene sequence encoding the enzymes (1) and (2) and the amino acid sequence information of the enzymes (1) and (2), as well as a method for preparing different vectors and a method for creating transformants. The terms "transformation" and "transformant" as used herein encompass transduction and transductants, respectively. One non-limiting example of cloning of the genes encoding the enzymes (1) and (2) will be described below.

Cloning of the genes encoding the enzymes (1) and (2) may suitably use commonly used gene cloning techniques. For example, using a standard technique such as the technique described in the reference literature, the chromosomal DNA and mRNA can be extracted from microorganisms and various cells capable of producing the enzymes (1) and (2). The extracted mRNA can be used as a template to synthesize cDNA. The resulting chromosomal DNA and cDNA may be used to construct a library of chromosomal DNA or cDNA.

For example, genes encoding the enzymes (1) and (2) can be obtained by cloning from the chromosomal DNA or cDNA derived from microorganisms having the genes, which serves as a template. The organisms of origin from which the genes encoding the enzymes (1) and (2) are derived are as described above; specific examples include, but are not limited to, *Aspergillus sojae* NBRC4239 strain, *Aspergillus oryzae* RIB40 strain, and *Aspergillus niger* IAM2533 strain. For example, the *Aspergillus sojae* NBRC4239 strain is cultured and the resulting cells are dehydrated and physically triturated using a mortar while chilled in liquid nitrogen to form fine powder-like cell debris, from which a fraction containing chromosomal DNA is extracted using a standard technique. A commercially available DNA extraction kit such as DNeasy Plant Mini Kit (Qiagen) can be used to extract the chromosomal DNA.

Subsequently, a polymerase chain reaction (referred to as PCR, hereinafter) was conducted using the chromosomal DNA as a template along with synthetic primers complementary to the sequences at the 5' and 3' ends. The primers are not particularly limited as long as they can amplify DNA fragments containing the gene. Examples of the primers include primers shown in SEQ ID NOs: 17 to 22 designed based on the genome sequence of *Aspergillus sojae*. These primers can amplify the full length of the target gene and can therefore eliminate the need for RACE. Alternatively, DNA sequences containing fragments of the target gene may be amplified using suitable PCR techniques such as 5' RACE and 3' RACE and these sequences are subsequently ligated to obtain a DNA segment containing the full length target gene.

The method for obtaining the genes encoding the enzymes (1) and (2) is not particularly limited; for example, rather than using genetic engineering techniques, the genes encoding the enzymes (1) and (2) may be constructed by chemical synthesis.

For example, the base sequences of the amplification products amplified by PCR and the chemically synthesized genes may be determined as follows. First, the DNA segment to be sequenced is inserted into a suitable vector according to the standard technique to prepare a recombinant DNA. For cloning into a vector, a commercially available kit, such as TA Cloning Kit (Invitrogen); commercially available plasmid vector DNA, such as pUC119 (Takara Bio), pUC18 (Takara Bio), pBR322 (Takara Bio), pBluescript SK+ (Stratagene), and pYES2/CT (Invitrogen); and commercially available bacteriophage vector DNA, such as AEMBL3 (Stratagene), may be used. The recombinant DNA is then used to transform host organisms, such as *Escherichia coli*, preferably *E. coli* JM109 strain (Takara Bio) and *E. coli* DH5a strain (Takara Bio). The recombinant DNA present in the transformant is then purified using a purification kit such as QIAGEN Plasmid Mini Kit (Qiagen).

The base sequences of genes inserted in the recombinant DNA are then determined by the dideoxy sequencing technique (Methods in Enzymology, 101, 20-78, 1983). The sequence analyzer used to determine the base sequence is not particularly limited; for example, Li-COR MODEL 4200L sequencer (Aloka), 370DNA sequencing system (Perkin Elmer), CEQ2000XL DNA analysis system (Beckman) may be used. The determined base sequences may then be used to estimate the amino acid sequence of the translated proteins, thus, the enzymes (1) and (2).

(Construction of a Recombinant Vector Containing Genes Encoding Enzymes (1) and (2))

Recombinant vectors containing the genes encoding the enzymes (1) and (2) (recombinant DNA) can be constructed by connecting a PCR amplification product containing any of the genes encoding the enzymes (1) and (2) with any of various vectors in such a manner that the recombinant vector can express the genes encoding the enzymes (1) and (2). For example, such a recombinant vector may be constructed by excising a DNA fragment containing any of the genes encoding the enzymes (1) and (2) with appropriate restriction enzyme and ligating the DNA fragment into a plasmid cut with appropriate restriction enzyme. The recombinant vector may also be obtained by connecting a DNA fragment containing the gene and having sequences homologous to a plasmid attached to the both ends with a DNA fragment derived from the plasmid amplified by inverse PCR using a commercially available recombinant vector preparation kit such as In-Fusion HD Cloning Kit (Clontech).

Another embodiment of the present invention includes a recombinant vector containing a gene encoding the enzyme (1), a recombinant vector containing a gene encoding the enzyme (2), and a recombinant vector containing both a gene encoding the enzyme (1) and a gene encoding the enzyme (2). The recombinant vector of the present invention may be used to create a transformed filamentous fungus of the present invention.

The recombinant vector of the present invention preferably includes a heterologous gene or a heterologous nucleic acid sequence. The heterologous gene may be any gene not naturally occurring in the host organism, including, for example, synthetic genes not based on the nucleic acid sequence derived from the host organism, genes derived from an organism different from the organism of origin from which the gene encoding the enzyme (1) is derived, genes derived from filamentous fungi or microorganisms other than the host organism, and genes derived from plants, animals or viruses. Specific examples of the heterologous genes when the host organism is a filamentous fungus includes, but are not limited to, DNA fragments derived from pUC19.

Specific examples of the recombinant vectors of the present invention include, but are not limited to, a recombinant vector containing a DNA fragment derived from pUC19, a DNA fragment derived from Ptef, a DNA fragment derived from AsEgtA and/or AsEgtC, a DNA fragment derived from Talp, and a DNA fragment derived from pyrG that are connected to one another.

(Method for Creating a Transformed Filamentous Fungus)

The method for creating a transformed filamentous fungus is not particularly limited; for example, a gene(s) encoding the enzyme (1) or the enzymes (1) and (2) may be inserted in the host filamentous fungus according to a standard method in such a manner that the enzymes are expressed in the host filamentous fungus. Specifically, a DNA construct in which any of the genes encoding the enzymes (1) and (2) has been inserted between an expression-inducing promoter and a terminator is constructed. Subsequently, a host filamentous fungus is transformed with only the DNA construct containing the gene encoding the enzyme (1) or with both the DNA construct containing the gene encoding the enzyme (1) and the DNA construct containing the gene encoding the enzyme (2) to obtain a transformed filamentous fungus that overexpresses only the gene encoding the enzyme (1) or both the gene encoding the enzyme (1) and the gene encoding the enzyme (2). In the present specification, DNA fragments comprising an expression-inducing promoter—a gene encoding the enzyme (1) or (2)—a terminator and recombinant vectors containing the DNA fragment that are prepared to transform the host filamentous fungus are collectively referred to as "DNA constructs."

The method for inserting the gene(s) encoding the enzyme (1) or the enzymes (1) and (2) in a host filamentous fungus in such a manner that the enzymes are expressed in the host filamentous fungus is not particularly limited; for example, the gene may be directly inserted into the chromosome of the host organism by making use of homologous recombination, or the gene may be connected to a plasmid vector, which is then introduced into the host filamentous fungus.

In the method that makes use of homologous recombination, a DNA construct may be connected between sequences homologous to the upstream region and the downstream region of a recombination site on a chromosome and inserted into the genome of the host filamentous fungus. As a result of this self-cloning, a transformant can be obtained in which the gene is overexpressed under control of a high expression promoter in the DNA construct. The high expression promoter may be any high expression promoter, including, for example, a promoter region of translation elongation factor TEF1 gene (tef1), a promoter region of α-amylase gene (amy), a promoter region of alkaline protease gene (alp), and other suitable promoters.

In the method that makes use of a vector, a DNA construct is integrated into a plasmid vector used to transform filamentous fungi using a standard method and a corresponding host filamentous fungus can be transformed with the plasmid vector according to a standard method.

A suitable vector-host system may be any system that allows the production of the enzyme (1) or the enzymes (1) and (2) in the host filamentous fungus, including, for example, a system based on pUC19 and a filamentous fungus, and a system based on pSTA14 (Mol. Gen. Genet. 218, 99-104, 1989) and a filamentous fungus.

While the DNA construct is preferably introduced into the chromosome of the host filamentous fungus, it may be used without introducing into the chromosome by integrating into a self-replicating vector (Ozeki et al. Biosci. Biotechnol. Biochem. 59, 1133 (1995)).

The DNA construct may contain a marker gene that allows the selection of transformed cells. Examples of the marker gene include, but are not limited to, genes compensating for the nutritional requirements of the host, such as pyrG, niaD and adeA; and drug-resistant genes such as those against pyrithiamine, hygromycin B and oligomycin. Also, the DNA construct preferably contains a promoter, a terminator and other regulatory sequences (such as enhancer and polyadenylated sequences) that enable the overexpression of the genes encoding the enzyme (1) or the enzymes (1) and (2) in the host cells. The promoter may be any suitable expression-inducing promoter or constitutive promoter, including, for example, tef1 promoter, alp promoter, and amy promoter. The terminator may also be any terminator, including, for example, alp terminator, amy terminator, and tef1 terminator.

The regulatory sequences for the genes encoding the enzymes (1) and (2) in the DNA construct are not necessarily required if the DNA fragments containing the genes encoding the enzymes (1) and (2) contain sequences having expression regulatory functions. Also, when transformation is performed by the cotransformation method, the DNA construct may not contain any marker genes.

Purification tags may be added to the DNA construct. For example, a suitable linker sequence may be added to the upstream or downstream of the gene encoding the enzymes (1) or (2) and six or more codons of histidine-encoding base sequences may be added to the linker to enable the purification on a nickel column.

One embodiment of the DNA construct is a DNA construct in which a tef1 gene promoter, a gene encoding the enzymes (1) or (2), an alp gene terminator and a pyrG marker gene are connected to the In-Fusion cloning Site located in the multiple cloning site of pUC19.

Any properly selected method known to those skilled in the art may be used for transformation into filamentous fungi; for example, the protoplast PEG technique in which protoplasts of a filamentous fungus are prepared and polyethylene glycol and calcium chloride are added may be used (See, for example, Mol. Gen. Genet. 218, 99-104, 1989, Japanese Unexamined Patent Application Publication No. 2007-222055). The culture medium to regenerate the transformed filamentous fungus is properly selected depending on the host filamentous fungi and the transformation marker gene used. For example, when *Aspergillus sojae* is used as the host filamentous fungus and pyrG gene is used as the transformation marker gene, the transformed filamentous fungus can be regenerated in a Czapek-Dox minimal medium (Difco) containing 0.5% agar and 1.2M sorbitol.

Alternatively, in order to obtain the transformed filamentous fungus of the present invention, the endogenous promoter for the gene(s) encoding the enzyme (1) or the enzymes (1) and (2) present on the chromosome of the host filamentous fungus may be substituted with a high expression promoter such as tef1 by homologous recombination. Again, a transformation marker gene such as pyrG is preferably inserted in addition to the high expression promoter. For example, a transformation cassette consisting of the upstream region of the gene encoding the enzyme (1) or (2)—a transformation marker gene—a high expression promoter—all or a part of the gene encoding the enzyme (1) or (2) described in Example 1 and FIG. 1 of Japanese Unexamined Patent Application Publication No. 2011-239681 may be used for this purpose. In this case, the upstream region of the gene encoding the enzyme (1) or (2) and all or a part of the gene encoding the enzyme (1) or (2) are used in homologous recombination. The all or a part of the gene encoding the enzyme (1) or (2) may include a region of the gene extending from the start codon to somewhere down the length of the gene. A suitable length of the region is preferably 0.5 kb or longer for homologous recombination.

In order to confirm that the transformed filamentous fungus of the present invention has successfully been created, the transformed filamentous fungus may be cultured under a condition that allows the detection of the enzymatic activity of the enzyme (1) or the enzymes (1) and (2) and subsequently a comparison is made to determine if the amount of ergothioneine produced in the culture after a culture period is greater than the amount of ergothioneine produced in the culture of the host filamentous fungi cultured under the same condition.

Alternatively, the confirmation of successful creation of the transformed filamentous fungus of the present invention may be made by extracting the chromosomal DNA from the transformed filamentous fungus, and performing a PCR using the chromosomal DNA as a template DNA to detect the presence of a PCR product that can be amplified if the transformation has occurred.

For example, a PCR can be performed using a combination of a forward primer for the base sequence of the promoter used and a reverse primer for the base sequence of the transformation marker gene and whether the product having an expected length is produced is determined.

When the transformation is carried out by homologous recombination, it is preferred to perfoLuu a PCR using a forward primer located upstream of the upstream homologous region used and a reverse primer located downstream of the downstream homologous region used and then determine whether the product having a length expected when the homologous recombination has occurred is produced.

(Host Filamentous Fungus)

The host filamentous fungus may be any filamentous fungus that can produce the enzyme (1) or the enzymes (1) and (2) when transformed by a DNA construct containing the gene encoding the enzyme (1) or DNA constructs containing the genes encoding the enzymes (1) and (2), respectively. Examples include, but are not limited to, filamentous fungi in which the production of ergothioneine is detected and filamentous fungi that have genes encoding the enzymes (1) and (2) on their genomic DNA. Specific examples of the host filamentous fungi include filamentous fungi described in Non-Patent Documents 1 and 2, such as filamentous fungi belonging to the genus *Aspergillus*, the genus *Neurospora*, the genus *Penicillium*, the genus *Fusarium*, the genus *Trichoderma*, the genus *Mucor*, the genus *Rhizopus*, and the genus *Neuspora*. Examples of the filamentous fungi that have genes encoding the enzymes (1) and (2) on their genomic DNA include filamentous fungi belonging to the genus *Neosartorya*, the genus *Byssochlamys*, the genus *Talaromyces*, the genus *Ajellomyces*, the genus *Paracoccidioides*, the genus *Uncinocarpus*, the genus *Coccidioides*, the genus *Arthroderma*, the genus *Trichophyton*, the genus *Exophiala*, the genus *Capronia*, the genus *Cladophialophora*, the genus *Macrophomina*, the genus *Leptosphaeria*, the genus *Bipolaris*, the genus *Dothistroma*, the genus *Pyrenophora*, the genus *Neofusicoccum*, the genus *Setosphaeria*, the genus *Baudoinia*, the genus *Gaeumannomyces*, the genus *Marssonina*, the genus *Sphaerulina*, the genus *Sclerotinia*, the genus *Magnaporthe*, the genus *Verticillium*, the genus *Pseudocercospora*, the genus *Colletotrichum*, the genus *Ophiostoma*, the genus *Metarhizium*, the genus *Sporothrix*, and the genus *Sordaria*.

Of these filamentous fungi, in terms of the safety and easy culturing, the host filamentous fungus is preferably any of the microorganisms of the genus *Aspergillus* listed above as the organisms of origin from which the genes encoding the enzymes (1) and (2) are derived, including *Aspergillus sojae, Aspergillus oryzae, Aspergillus niger, Aspergillus tamarii, Aspergillus awamori, Aspergillus usamii, Aspergillus kawachii*, and *Aspergillus saitoi*.

(Specific Examples of Genes Encoding Enzymes (1) and (2))

Examples of the gene encoding the enzyme (1) derived from the *Aspergillus sojae* NBRC4239 strain include a gene AsEgtA, which will be described in Examples below. Examples of the gene encoding the enzyme (2) derived from the *Aspergillus sojae* NBRC4239 strain include genes AsEgtB and AsEgtC, which will be also described in Examples below. The base sequences of the genes AsEgtA, AsEgtB and AsEgtC are shown in SEQ ID NOs: 1 to 3 in the sequence listing, respectively. Further, the amino acid sequences of the AsEgtA, AsEgtB and AsEgtC proteins are shown in SEQ ID NOs: 4 to 6 in the sequence listing, respectively.

Examples of the gene encoding the enzyme (1) derived from the *Aspergillus oryzae* RIB40 strain include a gene AoEgtA, which will be described in Examples below. Examples of the gene encoding the enzyme (2) derived from the *Aspergillus oryzae* RIB40 strain include genes AoEgtB and AoEgtC, which will be described in Examples below. The base sequences of the genes AoEgtA, AoEgtB and AoEgtC are shown in SEQ ID NOs: 23 to 25 in the sequence listing, respectively. Further, the amino acid sequences of the AoEgtA, AoEgtB and AoEgtC proteins are shown in SEQ ID NOs: 26 to 28 in the sequence listing, respectively.

Examples of the gene encoding the enzyme (1) derived from the *Aspergillus niger* IAM2533 strain include a gene AnEgtA, which will be described in Examples below. The base sequences of the gene AnEgtA is shown in SEQ ID NO: 33 in the sequence listing, respectively. Further, the amino acid sequence of the AnEgtA protein is shown in SEQ ID NO: 34 in the sequence listing.

Genes encoding the enzymes (1) and (2) may be obtained from filamentous fungi other than those of *Aspergillus sojae, Aspergillus oryzae* and *Aspergillus niger* by any suitable method. For example, a homology search by BLAST may be conducted on the genomic DNA of other filamentous fungi based on the base sequences of the genes AsEgtA, AsEgtB and AsEgtC (SEQ ID NOs: 1 to 3) and the amino acid sequences of the AsEgtA, AsEgtB and AsEgtC proteins (SEQ ID NOs: 4 to 6), to identify genes having a base sequence with a high sequence identity to the base sequences of the genes AsEgtA, AsEgtB and AsEgtC. Alternatively, genes encoding the enzymes (1) and (2) may be obtained by identifying proteins having a high sequence identity to the AsEgtA, AsEgtB and AsEgtC proteins from the total protein of filamentous fungi and identifying the genes encoding these proteins. Whether the resulting genes are equivalent to the genes encoding the enzymes (1) and (2) can be determined by transforming the organism of origin (as the host filamentous fungus) with the obtained gene and determining if the production of ergothioneine is enhanced compared to the host filamentous fungi.

Since *Aspergillus sojae, Aspergillus oryzae* and *Aspergillus niger* grow under similar conditions, it may be possible to insert the genes of the respective fungi into one another to mutually transform the respective fungi. For example, a gene (s) encoding the enzyme (1) or the enzymes (1) and (2) derived from *Aspergillus sojae* may be introduced into the host filamentous fungus of *Aspergillus oryzae* or *Aspergillus niger* to transform them. In order to ensure that the enzyme (1) or the enzymes (1) and (2) have the desired enzymatic activity, it is preferred that the filamentous fungus of origin from which the genes encoding the enzyme (1) or the enzymes (1) and (2) are derived and the host filamentous fungus are identical. For example, a gene(s) encoding the enzyme (1) or the enzymes (1) and (2) derived from *Aspergillus sojae* may be introduced into the same *Aspergillus sojae*.

The genes encoding the enzymes (1) and (2) may be genes optimized for their codons, secondary structures, and GC contents based on the amino acid sequence of the genes encoding the enzymes (1) and (2) derived from *Aspergillus sojae*. Specific examples of such genes include EcEgtA (SEQ ID NO: 37) and EcEgtC (SEQ ID NO: 38) synthesized for expression in *E. coli*.

One Embodiment of Transformed Filamentous Fungi of the Present Invention

One embodiment of the present invention is a transformed filamentous fungus obtained by inserting the genes AsEgtA, AoEgtA and/or AnEgtA into *Aspergillus sojae, Aspergillus oryzae, Aspergillus niger* or other filamentous fungi so that the proteins encoded by the inserted genes are overexpressed in the fungus. One embodiment of the present invention is a transformed filamentous fungus transformed by inserting the genes AsEgtA, AoEgtA and/or AnEgtA, and the genes AsEgtB, AsEgtC, AoEgtB and/or AoEgtC into *Aspergillus sojae, Aspergillus oryzae, Aspergillus niger* or other filamentous fungi so that the proteins encoded by the inserted genes are overexpressed in the fungus. Such transformed filamentous fungi show a higher production of ergothioneine than the host filamentous fungus since they overexpress the enzyme (1) or the enzymes (1) and (2) encoded by the inserted genes. Furthermore, as described in Examples below, the transformed *Aspergillus sojae* transformed to overexpress the AsEgtA protein and the AsEgtB or AsEgtC protein, for example, shows a higher production of ergothioneine than the transformed *Aspergillus sojae* transformed to overexpress the AsEgtA protein alone. Accordingly, the transformed filamentous fungus of the present invention is preferably a transformed filamentous fungus in which the expression of the gene(s) encoding the enzyme (1) or the enzymes (1) and (2) is enhanced such that the amount of ergothioneine is increased compared to the host filamentous fungus. Also, the transformed filamentous fungus of the present invention is more preferably a transformed filamentous fungus in which the expression of the genes encoding the enzymes (1) and (2) is enhanced such that the amount of ergothioneine is increased compared to a transformed filamentous fungi in which the expression of the gene encoding the enzyme (1) is enhanced.

Also, as described in Examples below, when the transformed *Aspergillus sojae* transformed to overexpress the AsEgtA protein or the transformed *Aspergillus sojae* transformed to overexpress the AsEgtA protein and the AsEgtB or AsEgtC protein was cultured at 30° C. for 3 days in a DPY medium suitable for the growth of the host filamentous fungi *Aspergillus sojae*, ergothioneine was obtained in an amount of 26.6 to 37.3 mg per 1 g of dry cell mass. In contrast, when the transformed *Aspergillus sojae* transformed to overexpress the AsEgtB or AsEgtC protein is cultured under the same condition, ergothioneine was obtained only in an amount of 0.9 to 1.2 mg per 1 g of dry cell mass. Accordingly, one embodiment of the transformed filamentous fungus of the present invention is a transformed filamentous fungus in which the expression of the gene(s) encoding the enzyme (1) or the enzymes (1) and (2) is enhanced such that when the transformed filamentous fungus of the present invention is cultured at 30° C. for 3 days in a culture medium suitable for the growth of the host filamentous fungi, the amount of ergothioneine is 5.0 mg or more, preferably 10.0 mg or more, more preferably 20.0 mg or more, still more preferably 25.0 mg or more per 1 g of dry cell mass. Furthermore, another embodiment of the transformed filamentous fungus of the present invention is a transformed filamentous fungus in which the expression of the genes encoding the enzymes (1) and (2) is enhanced such that when the transformed filamentous fungus of the present invention is cultured at 30° C. for 3 days in a culture medium suitable for the growth of the host filamentous fungi, the amount of ergothioneine is 27.0 mg or more, preferably 28.0 mg or more, more preferably 29.0 mg or more, still more preferably 30.0 mg or more per 1 g of dry cell mass.

In some cases, the transformed filamentous fungus of the present invention may express, along with the enzymes (1) and (2) produced from the inserted genes encoding the enzymes (1) and (2), wild-type enzymes (1) and (2) that have the same or different structural properties as/from the enzymes (1) and (2), the wild-type enzymes (1) and (2) being expressed by the genes encoding the endogenous enzymes (1) and (2) of the host filamentous fungi.

Another aspect of the present invention includes a transformed archaebacterium or a transformed bacterium that has genes encoding the enzymes (1) and (2) inserted therein and that overexpresses the inserted genes. Non-limiting examples of the transfoiined bacteria include transformed *E. coli* transformed with a plasmid vector containing EcEgtA or EcEgtA and EcEgtC.

(Production Method of Ergothioneine of the Present Invention)

One production method of ergothioneine of the present invention includes at least the step of applying histidine and cysteine to the transformed filamentous fungus of the present invention to obtain ergothioneine. The method for applying histidine and cysteine to the transformed filamentous fungus is not particularly limited and may be any method that can expose the transformed filamentous fungus to histidine and cysteine to allow the enzymes of the transformed filamentous fungus to produce ergothioneine. For example, the transformed filamentous fungus may be cultured in a culture medium containing histidine and cysteine and optimized for the growth of the transformed filamentous fungus under various culture conditions suitable for the transformed filamentous fungus, to produce ergothioneine. The culture method is not particularly limited; for example, the solid culture or liquid culture technique performed under aeration condition may be employed.

The culture medium may be any standard culture medium designed for culturing filamentous fungi, that is, either synthetic or natural culture medium that contains a carbon source, a nitrogen source, inorganic materials, and other nutrients in suitable proportions. When the filamentous fungus is a microorganism of the genus *Aspergillus*, the DPY medium as described in Examples below may be used while not particularly limited. It is preferred, however, that the medium contain, as a component, iron (II) required for the activation of the enzyme (1). While iron (II) may be added to the medium in the form of a compound, it may also be added as a mineral-containing material.

Histidine and cysteine are not particularly limited; for example, histidine and cysteine themselves, derivatives containing histidine and cysteine as constituents (for example, cystine), and histidine- and cysteine-containing materials may be used.

The culture condition may be any culture condition commonly known to those skilled in the art; for example, the initial pH of the culture medium may be conditioned to 5 to 10 and the culture temperature to 20 to 40° C., and the culture time may be properly selected and may vary from several hours to several days, preferably from 1 to 7 days, and more preferably from 2 to 5 days. The culture means is not particularly limited; for example, an aerated, agitated, submerged culture, a shake culture, a static culture or other suitable culture techniques may be employed with the culture condition preferably adjusted so that sufficient amounts of dissolved oxygen are present. One example of the culture medium and culture condition for culturing microorganisms of the genus *Aspergillus* includes a shake culture in which the fungus is cultured at 30° C. under shaking at 160 rpm over 3 to 5 days in a DPY medium as described in Examples below.

The method for extracting ergothioneine from the culture after completion of the culture is not particularly limited. For extraction purposes, the fungal cells collected from the culture by filtration, centrifugation or other manipulation may be used without further processing, or alternatively, the fungal cells dried or, if desired, triturated after collection may be used. The method for drying fungal cells is not particularly limited; for example, lyophilization, drying in the sun, hot-air drying, vacuum drying, aeration drying, drying under reduced pressure or other suitable drying techniques may be used.

The solvent used for extraction may be any solvent that can dissolve ergothioneine, including, for example, organic solvents, such as methanol, ethanol, isopropanol and acetone; water-containing organic solvents composed of these organic solvents and water mixed together; and water, warm water and hot water. After addition of the solvent, ergothioneine is extracted while the cells are triturated as necessary. The temperature of the extraction solvent may be set to from room temperature to 100° C.

In one embodiment of the extraction method of ergothioneine, the fungal cells collected from the culture are washed with water and added to water to prepare a suspension. The resulting suspension is then subjected to a heat treatment such as at 98 to 100° C. for 15 minutes and then centrifuged to collect the supernatant. Subsequently, the collected supernatant is filtered to remove impurities. Alternatively, the heated suspension may be directly filtered without centrifugation.

Instead of the heat treatment described above, the cells may be subjected to cell destruction processes that break cells using cell destruction means such as an ultrasonicator, a French press, a DYNO-MILL, and a mortar; processes for lysing the fungal cell walls with Yatalase and other cell wall-lysing enzymes; or processes for lysing the fungal cells with a surfactant such as SDS and Triton X-100. These processes may be used either individually or in combination.

In order to purify ergothioneine, the resulting extract can be subjected to various purification processes including centrifugation, filtration, ultrafiltration, gel filtration, separation by solubility difference, solvent extraction, chromatography (adsorption chromatography, hydrophobic interaction chromatography, cation exchange chromatography, anion exchange chromatography, and reversed-phase chromatography), crystallization, active carbon treatment, membrane treatment, and other purification processes.

The qualitative or quantitative analysis technique of ergothioneine is not particularly limited; the analysis may be conducted by, for example, HPLC. A person skilled in the art would properly select the conditions for the HPLC separation; for example, HPLC may be performed using the conditions described in Examples below.

The transformed filamentous fungus of the present invention can be used to obtain ergothioneine in high yields. For example, the yield of ergothioneine shown in FIG. S6 of Non-Patent Document 5 is an extremely low amount of at most about 10 μg per 40 mL of the culture. In contrast, as much as 3 mg or more ergothioneine per 10 ml of the culture can be produced by using the transformed filamentous fungus of the present invention.

(Production Method of High-Purity-Ergothioneine-Containing Compositions of the Present Invention)

The method for producing a high-purity-ergothioneine-containing composition according to the present invention includes the step of culturing a transformed filamentous fungus in a culture medium containing histidine and cysteine and suitable for the growth of the host filamentous fungus to obtain a culture, from which an ergothioneine-containing composition having a purity of 5% or higher is obtained.

The purity of the ergothioneine-containing composition obtained by the production method of a high-purity-ergothioneine-containing composition of the present invention may be any concentration higher than or equal to 5%. Preferably, the purity is higher than or equal to 6%, more preferably higher than or equal to 8%, and still more preferably higher than or equal to 9%. In order to measure the purity of the ergothioneine-containing composition, for example, an ergothioneine extract is obtained from the culture obtained by culturing the transformed filamentous fungus of the present invention. The resulting ergothioneine extract is then dried by, for example, lyophilization, to obtain a dry powder. The resulting dry powder is then dissolved in distilled water to a proper concentration to give a sample for purity measurement. The sample is then measured by HPLC or other techniques for quantify ergothioneine and the purity is calculated from the results of the measurement and the sample for purity measurement.

Another embodiment of the production method of the present invention is a production method that uses, rather than the transformant, a microorganism that has the gene(s) encoding the enzyme (1) or the enzymes (1) and (2) on its genomic DNA. Another embodiment of the production method of the present invention, for example, is a production method of ergothioneine or a high-purity-ergothioneine-containing composition, comprising the step of applying histidine and cysteine to a filamentous fungus, such as a microorganism of the genus *Aspergillus*, such as *Aspergillus oryzae* and *Aspergillus sojae*, having a gene(s) encoding the enzyme (1) or the enzymes (1) and (2) on its genomic DNA to obtain ergothioneine or a high-purity-ergothioneine-containing composition.

Ergothioneine, which is the product of the production method of the present invention, can cause growth inhibition or production inhibition in the microorganism used. Accordingly, an oxidizing agent such as copper ions may be added to the culture medium to dimerize (by formation of S—S linkage) the ergothioneine product and to thereby avoid the grow inhibition or the production inhibition in the microorganism. Thus, in the production method of the present invention, it is preferred that oxidizing agents such as copper ions is present upon application of histidine and cysteine to the microorganism.

In the production method of the present invention, various other steps or manipulations may be performed before, after, or during the above-described step as long as the objectives of the present invention can be achieved.

(Application of Ergothioneine)

Having advantageous characteristics of being a functional biological material having various physiological activities, as well as being a heat-resistant, water-soluble material, the ergothioneine obtained by the transformed filamentous fungus or the production method of the present invention are useful as functional food products, food and beverage products for specified health use, food and beverage products with nutrient function claims, food and beverage products with health function claims, food and beverage products for special uses, nutritional supplement food and beverage products, health-promoting food and beverage products, supplements, beauty food and beverage products, cosmetic products, pharmaceutical products, quasi-pharmaceutical products, animal feeds, and raw-materials for producing these products.

The present invention will now be described in further detail with reference to the following Examples, which are not intended to limit the present invention. The present invention may take various forms to the extent that the objectives of the present invention are achieved.

EXAMPLES

Example 1: Preparation of DNA Constructs with an Inserted Gene AsEgtA, AsEgtB or AsEgtC (1) Searching of Genes of Interest NCU04343 and NCU11365 are among the enzymes known to be involved in the biosynthesis of ergothioneine in *Neurospora crassa* (See, Non-Patent Documents 3 and 4). Non-Patent Document 3 also suggests the possible involvement of NCU04636 in the biosynthesis of ergothioneine. Given that, using genes encoding the three enzymes of *Neurospora crassa* as query sequences, domains with a relatively high sequence identity to the genes encoding each of NCU04343, NCU04636 and NCU11365 were searched based on the genome sequence of the NBRC4239 strain of *Aspergillus sojae*. The search was conducted using a BLAST program (tblastn) and the genome sequence of the NBRC4239 strain of *Aspergillus sojae* (DDBJ/EMBL/GenBank DNA databases, Accession numbers for the 65 scaffold sequences; DF093557-DF093585, DNA RESEARCH 18, 165-176, 2011).

As a result, a gene shown in SEQ ID NO: 1 was found as a sequence domain with a relatively high sequence identity to NCU04343. This gene was named as AsEgtA gene (SEQ ID NO: 1), indicating an egtA gene originating from *Aspergillus sojae*. Also, a gene shown in SEQ ID NO: 2 was found as a sequence domain with a relatively high sequence identity to NCU04636 and was named as AsEgtB gene (SEQ ID NO: 2). Further, a gene shown in SEQ ID NO: 3 was found as a sequence domain with a relatively high sequence identity to NCU11365 and was named as AsEgtC gene (SEQ ID NO: 3).

A comparison of the sequence identity on the amino acid level was performed using a gene information processing software Genetyx network model, version 12.0.1 (Genetyx) and indicated the sequence identities of the AsEgtA protein (SEQ ID NO: 4), the AsEgtB protein (SEQ ID NO: 5) and the AsEgtC protein (SEQ ID NO: 6) to NCU04343, NCU04636 and NCU11365 were 46%, 75% and 44%, respectively. Also, the sequence identity of AsEgtC protein to SPBC660.12c, an ortholog of NCU11365 in *Schizosaccharomyces pombe*, was found to be 27%. These results suggest that the base sequences and the amino acid sequences of AsEgtA, AsEgtB and AsEgtC may be used to search for the egtA, egtB and egtC genes of other microorganisms of the genus *Aspergillus*.

(2) Extraction of Chromosomal DNA of *Aspergillus sojae* NBRC4239 Strain

In a 150 ml Erlenmeyer flask, 30 mL of a polypeptone-dextrin medium (1 (w/v) % polypeptone, 2 (w/v) % dextrin, 0.5 (w/v) % $KH_2PO_4$, 0.1 (w/v) % $NaNO_3$, 0.05 (w/v) % $MgSO_4.7H_2O$, 0.1 (w/v) % casamino acid; pH 6.0) was prepared with distilled water. The medium was inoculated with the conidia of *Aspergillus sojae* NBRC4239 strain and was subjected to shake culture overnight at 30° C. The cells were collected from the resulting culture broth by filtration and were placed between sheets of paper towel to remove moisture. The cells were then triturated using a liquid nitrogen-chilled mortar and pestle while being chilled in liquid nitrogen. Using DNeasy Plant Mini Kit (Qiagen), the chromosomal DNA was extracted from the resulting triturated cells.

(3) Preparation of a Construct Plasmid

The following elements were integrated into plasmid pUC19 to make a plasmid for making a construct (construct plasmid): Ptef, a promoter sequence of translation elongation factor gene tef1 (a 748 bp upstream region of tef1 gene; SEQ ID NO: 7); Talp, a terminator sequence of alkaline protease gene alp (a 800 bp downstream region of alp gene; SEQ ID NO: 8); and pyrG, a transformation marker gene that compensates for the requirement for uridine (1838 bp including a 407 bp upstream region, a 896 bp coding region and a 535 bp downstream region; SEQ ID NO: 9). Specifically, the plasmid was prepared in the following manner.

Ptef, Talp and pyrG were amplified by PCR using chromosomal DNA of *Aspergillus sojae* NBRC4239 strain obtained above to serve as a template DNA, KOD-Plus-DNA Polymerase (Toyobo) to serve as PCR enzyme, the reagents provided with the enzyme to serve as reaction reagents, and Mastercycler gradient (Eppendolf) to serve as a PCR device. The PCR was performed according to the protocol provided with the enzyme. Primers used to amplify Ptef, Talp and pyrG and the PCR conditions are shown in Tables 1 to 3 below. Of the sequences shown in the tables, the sequences shown in lower case are added sequences that serve to connect the amplified fragments of Ptef, Talp and pyrG in this order and further connect them to pUC19. The amplified DNA fragments were separated in 1 (w/v) % agarose gel and purified using QIAquick Gel Extraction Kit (Qiagen).

TABLE 1

| Amplified target region | Pref |
|---|---|
| Forward primer SEQ ID NO: 10 | Ptef1_-748R_pUC cggtacccggggatcTGTGGACCAGACAGGCGC CACTC |
| Reverse primer SEQ ID NO: 11 | Ptef1_-1R_Talp atgtactcctggtacTTTGAAGGTGGTGCGAAC TTTGTAG |

TABLE 1-continued

| PCR condition | 2 min. at 94° C. (15 sec. at 94° C., 30 sec. at 62° C., 1 min. at 68° C.) x 25 cycles |
|---|---|

TABLE 2

| Amplified target region | Talp |
|---|---|
| Forward primer SEQ ID NO: 12 | Talp_1F GTACCAGGAGTACATTGGAGAGTTCTAC |
| Reverse primer SEQ ID NO: 13 | Talp_800R CCGATCCAACCACCCGGCTATCG |
| PCR condition | 2 min. at 94° C. (15 sec. at 94° C., 30 sec. at 62° C., 1 min. at 68° C.) x 25 cycles |

TABLE 3

| Amplified target region | pyrG |
|---|---|
| Forward primer SEQ ID NO: 14 | PyrG_407_F_Talp gggtggttggatcggTTGGGCTTATTGCTATGT CCCTGAAAGG |
| Reverse primer SEQ ID NO: 15 | PyrG_1431R_pUC cgactctagaggatcCCGCACCTCAGAAGAAAA GGATGA |
| PCR condition | 2 min. at 94° C. (15 sec. at 94° C., 30 sec. at 62° C., 2 min. at 68° C.) x 25 cycles | pUC19 used was pUC19 linearized Vector provided with In-Fusion HD Cloning Kit (Clontech). Using In-Fusion HD Cloning Kit described above, the amplified Ptef, Talp and pyrG were ligated into pUC19 at In-Fusion Cloning Site located in the multiple cloning site according to the protocols provided with the kit, to obtain a construct plasmid.

The resulting construct plasmid was used to transform competent cells ECOS Competent *E. coli* JM109 (Nippon Gene) in accordance with the manufacturer's instructions to obtain transformed *E. coli*.

The resulting transformed *E. coli* was then subjected to shake culture overnight at 37° C. in an LB liquid medium containing 50 μg/ml ampicillin. After the culture period, the culture solution was centrifuged to collect cells. Using FastGene Plasmid Mini Kit (Nippon Genetics), plasmid DNA was extracted from the collected cells according to the protocols provided with the kit.

(4) Preparation of a Construct for Inserting a Gene of Interest

A DNA construct consisting of genes of interest AsEgtA, AsEgtB or AsEgtC connected between Ptef and Talp of a construct plasmid was prepared as follows.

An inverse PCR was performed using the construct plasmid obtained above to serve as a template DNA, KOD-Plus-DNA Polymerase (Toyobo) to serve as PCR enzyme, the reagents provided with the enzyme to serve as reaction reagents, and Mastercycler gradient (Eppendolf) to serve as a PCR device. The inverse PCR was performed according to the protocol provided with the enzyme to obtain a vector fragment of the construct plasmid. Primers and the PCR conditions used are shown in Table 4 below. The amplified vector fragments were separated in 1 (w/v) % agarose gel and purified using QIAquick Gel Extraction Kit (Qiagen).

TABLE 4

| | |
|---|---|
| Amplified target region | Construct plasmid |
| Forward primer SEQ ID NO: 16 | Ptef_-1R<br>TTTGAAGGTGGTGCGAACTTTGTAG |
| Reverse primer SEQ ID NO: 12 | Talp_1F (above described)<br>GTACCAGGAGTACATTGGAGAGTTCTAC |
| PCR condition | 2 min. at 94° C. (10 sec. at 98° C., 30 sec. at 65° C., 6 min. at 68° C.) x 20 cycles |

To amplify the genes AsEgtA (SEQ ID NO: 1), AsEgtB (SEQ ID NO: 2), and AsEgtC (SEQ ID NO: 3) derived from *Aspergillus sojae*, a PCR was performed using the chromosomal DNA of *Aspergillus sojae* NBRC4239 strain obtained above to serve as template DNA, KOD-Plus-DNA Polymerase (Toyobo) to serve as PCR enzyme, the reagents provided with the enzyme to serve as reaction reagents, and Mastercycler gradient (Eppendolf) to serve as a PCR device. The PCR was performed according to the protocol provided with the enzyme. Primers used to amplify AsEgtA, AsEgtB and AsEgtC and the PCR conditions are shown in Tables 5 to 7 below. Of the sequences shown in the tables, the sequences shown in lower case are added sequences that serve to connect the amplified fragments to the construct plasmid (between Ptef and Talp). The amplified DNA fragments were separated in 1 (w/v) % agarose gel and purified using QIAquick Gel Extraction Kit (Qiagen).

TABLE 5

| | |
|---|---|
| Amplified target region | AsEgtA |
| Forward primer SEQ ID NO: 17 | EgtA_1F_Ptef<br>cgcaccaccttcaaaATGTCACCTTTGGCTCTCTCTCC |
| Reverse primer SEQ ID NO: 18 | EgtA_2925R_Talp<br>atgtactcctggtacCTAAAGATCCCGCACCAGGCGT |
| PCR condition | 2 min. at 94° C. (15 sec. at 94° C., 30 sec. at 62° C., 3 min. at 68° C.) x 25 cycles |

TABLE 6

| | |
|---|---|
| Amplified target region | AsEgtB |
| Forward primer SEQ ID NO: 19 | EgtB_1F_Ptef<br>cgcaccaccttcaaaATGTCTAATGTTACCCAATCAGCCTTGAG |
| Reverse primer SEQ ID NO: 20 | EgtB_1770R_Talp<br>atgtactcctggtacTTAATGTTGACTCCATTCGATCGTGTTCAG |
| PCR condition | 2 min. at 94° C. (15 sec. at 94° C., 30 sec. at 62° C., 2 min. at 68° C.) x 25 cycles |

TABLE 7

| | |
|---|---|
| Amplified target region | AsEgtC |
| Forward primer SEQ ID NO: 21 | EgtC_1F_Ptef<br>cgcaccaccttcaaaATGACCACTCCCTTCGGAGCT |

TABLE 7-continued

| | |
|---|---|
| Reverse primer SEQ ID NO: 22 | EgtC_1529R_Talp<br>atgtactcctggtacTCAAAGCTTCGCAGAAGAAACCCCAACC |
| PCR condition | 2 min. at 94° C. (15 sec. at 94° C., 30 sec. at 62° C., 2 min. at 68° C.) x 25 cycles |

The vector fragments amplified as described above and AsEgtA, AsEgtB or AsEgtC were connected using In-Fusion HD Cloning Kit according to the protocol provided with the kit to obtain a DNA construct for inserting a gene of interest in which AsEgtA, AsEgtB or AsEgtC has been inserted. The so-obtained DNA construct consists of a DNA fragment derived from pUC19, a DNA fragment of Ptef, a DNA fragment of AsEgtA, AsEgtB or AsEgtC, a DNA fragment of Talp, a DNA fragment of pyrG, and a DNA fragment derived from pUC19 that are connected in series in the direction from the 5' end to the 3' end. In other words, three different DNA constructs in which the sequence Ptef-AsEgtA, AsEgtB or AsEgtC-Talp-pyrG was connected sequentially into the MCS of pUC19 were obtained.

The resulting DNA constructs were used to transform competent cells ECOS Competent *E. coli* JM109 (Nippon Gene) in accordance with the manufacturer's instructions to obtain transformed *E. coli*.

The resulting transformed *E. coli* was then subjected to shake culture overnight at 37° C. in an LB liquid medium containing 50 μg/ml ampicillin. After the culture period, the culture solution was centrifuged to collect cells. Using FastGene Plasmid Mini Kit (Nippon Genetics), the plasmid DNA was extracted from the collected cells according to the protocols provided with the kit.

The base sequence of each DNA inserted in the extracted plasmid DNA was determined to confirm that a DNA construct in which AsEgtA, AsEgtB or AsEgtC had been inserted was obtained.

Example 2: Preparation of Transformed *Aspergillus sojae* (1)

(1) pyrG-Disrupted Strain Derived from *Aspergillus sojae* NBRC4239 Strain.

Each DNA construct was precipitated with ethanol and dissolved in TE to form a DNA solution with a desired concentration. The DNA solution was then used to transform a pyrG-disrupted strain derived from the *Aspergillus sojae* NBRC4239 strain (i.e., the strain from which a 48 bp upstream region of the pyrG gene, a 896 bp coding region, and a 240 bp downstream region of the pyrG gene have been deleted).

(2) Transformation of pyrG-Disrupted Strain Derived from the *Aspergillus sojae* NBRC4239 Strain In a 500 ml Erlenmeyer flask, mycelium of the pyrG-disrupted strain derived from the *Aspergillus sojae* NBRC4239 strain was inoculated into 100 ml of a polypeptone dextrin liquid medium containing 20 mM uridine and the inoculated medium was subjected to shake culture at 30° C. for about 20 hours. Subsequently, the cells were collected. Protoplasts were prepared from the collected cells. The resulting protoplasts were then transformed with 20 μg of the DNA construct for inserting a gene of interest using the protoplast PEG technique and the protoplasts were incubated at 30° C. for 5 days or more in a Czapek-Dox minimal medium (Difco; pH 6) containing 0.5 (w/v) % agar and 1.2

M sorbitol to obtain transformed *Aspergillus sojae* as the cells having the ability to form colonies.

Since pyrG, a gene that compensates for the requirement for uridine, had been introduced into the transformed *Aspergillus sojae*, the transformants were able to grow in the uridine-free medium and were selected as strains having the introduced target gene.

Example 3: Production of Ergothioneine by Transformed *Aspergillus sojae* (1)

As shown in Table 8 below, the *Aspergillus sojae* NBRC4239 strain to serve as control; the transformed *Aspergillus sojae* transformed with one of the genes AsEgtA, AsEgtB and AsEgtC; and the transfo med *Aspergillus sojae* transformed with the gene AsEgtA and the gene AsEgtB or AsEgtC were compared for their ability to produce ergothioneine in the following manner.

TABLE 8

| Introduced gene | Strain |
| --- | --- |
| — | Control strain |
| AsEgtA, AsEgtB | (AsEgtA + AsEgtB) Transformant |
| AsEgtA, AsEgtC | (AsEgtA + AsEgtC) Transformant |
| AsEgtA | AsEgtA Transformant |
| AsEgtB | AsEgtB Transformant |
| AsEgtC | AsEgtC Transformant |

In a 50 mL Erlenmeyer flask, conidia of the fungal strains shown in Table 8 were inoculated into 10 mL of a DPY medium (1 (w/v) % polypeptone, 2 (w/v) % dextrin, 0.5 (w/v) % yeast extract, 0.5 (w/v) % $KH_2PO_4$, 0.05 (w/v) % $MgSO_4 \cdot 7H_2O$; pH not adjusted) and the inoculated medium was subjected to shake culture at 160 rpm at 30° C. for 3 days. After the culture period, the cells were collected from the culture on Miracloth (Calbiochem). The collected cells were washed with 40 ml distilled water and the cells were pressed between sheets of paper towel to squeeze out the moisture and to thus obtain wet cells. The mass of the wet cells was weighed and twice as much water as the mass of the wet cells was added and the mixture was stirred to obtain a cell suspension. The resulting cell suspension was subjected to a heat treatment at 98° C. for 15 min. Following the heat treatment, the suspension was centrifuged to collect the extracellular fluid as the supernatant, which in turn was filtered through a 0.45 µm filter to obtain an ergothioneine extract.

The resulting ergothioneine extract was analyzed by HPLC using the following conditions:
column; COSMOSIL HILIC (4.6×250 mm)
eluent; acetonitrile: 10 mM ammonium acetate=8:2 flow rate; 1 ml/min
detection wavelength; 220 nm
temperature; room temperature
quantification method; calibration curve method using ergothioneine sample (Enzo Life Sciences; Cat. No. BML-FR111)

From each of the fungal strains shown in Table 8, the specimens that contained the largest amounts of ergothioneine were selected and were compared for the ergothioneine (EGT) production. The results of the comparison are shown in Table 9 and FIG. 1. Meanwhile, the moisture content of some of the wet cells of the AsEgtA transformant (dehydrated with paper towel) was measured by a moisture analyzer (MX-50; A & D) and determined to be 77.7%. Based on this, the moisture content used to estimate the produced amounts of ergothioneine per one gram of dry cell in Table 9 was assumed to be 780.

Also, the results of HPLC performed on the ergothioneine extracts of the control strain (Control) and the AsEgtA transformant are shown in the charts of FIG. 2. Further, the purity of ergothioneine in the ergothioneine extracts was measured by the following procedure.

Specifically, in a 500 mL Erlenmeyer flask, conidia of the AsEgtA transformant were inoculated into 100 ml of a DPY medium and the inoculated medium was subjected to shake culture at 160 rpm at 30° C. for 3 days. After the culture period, the cells were collected from the culture on Miracloth. The collected cells were washed with 200 ml distilled water and the cells were pressed between sheets of paper towel to squeeze out the moisture and to thus obtain wet cells. The mass of the wet cells was weighed and twice as much water as the mass of the wet cells was added and the mixture was stirred to obtain a cell suspension. The resulting cell suspension was heated in a boiled water bath for 15 min. Following the heating, the suspension was centrifuged to collect the extracellular fluid as the supernatant, which in turn was filtered through a 0.45 µm filter to obtain an ergothioneine extract. The resulting ergothioneine extract was lyophilized to obtain a lyophilized powder. The resulting lyophilized powder was dissolved in distilled water to 25 mg/ml to give a sample for purity measurement. The amount of ergothioneine in the sample for purity measurement was measured and determined to be 2.3 mg/ml. Thus, the purity of EGT in the extract was calculated to be 9.2%.

TABLE 9

| Strain | EGT concentration (mg/ml extract) | Wet cell weight (mg) | Total extract volume (µl) | EGT total amount | | Estimated with 78% moisture mg/g dry cell |
| --- | --- | --- | --- | --- | --- | --- |
| | | | | mg/10 ml cell culture | mg/g wet cell | |
| control strain | 0.10 | 611.7 | 1451 | 0.15 | 0.24 | 1.1 |
| AsEgtA + AsEgtB transformant | 4.23 | 384.4 | 746 | 3.16 | 8.21 | 373 |
| AsEgtA + AsEgtC transformant | 3.09 | 531.5 | 1120 | 3.46 | 6.51 | 29.6 |
| AsEgtA transformant | 2.80 | 550.7 | 1152 | 3.23 | 5.86 | 26.6 |
| AsEgtB transformant | 0.08 | 575.8 | 1380 | 0.11 | 0.19 | 0.9 |
| AsEgtC transformant | 0.12 | 505.7 | 1127 | 0.14 | 0.27 | 1.2 |

As can be seen from Table 9 and FIG. 1, the amount of ergothioneine produced was higher in each of the AsEgtA transformant, the (AsEgtA+AsEgtB) transformant, and the (AsEgtA+AsEgtC) transformant, which were transformed by introducing one or two of the three genes of interest, as compared to any of the non-transformed control strain and the AsEgtB transformant and the AsEgtC transformant. As can be seen, although the AsEgtA transformant shows high production of ergothioneine, the ergothioneine production in each of the AsEgtB transformant and the AsEgtC transformant was comparable to that in the control strain. Also, the amount of ergothioneine produced in each of the (AsEgtA+AsEgtB) transformant and the (AsEgtA+AsEgtC) transformant was higher than the total amount of ergothioneine of the AsEgtA transformant and the AsEgtB transformant combined, or the AsEgtA transformant and the AsEgtC transformant combined. Considering these facts, it turns out that the ergothioneine production capability of each of the (AsEgtA+AsEgtB) transformant and the (AsEgtA+AsEgtC) transformant is increased multiplicatively, rather than additively, with respect to the AsEgtA transformant, the AsEgtB transformant and the AsEgtC transformant.

Also, the (AsEgtA+AsEgtB) transformant was able to produce as much as 37.3 mg/g dry cell of ergothioneine after a 3-day culture period using the same culture medium and culture conditions as those used to culture common filamentous fungi. In contrast, Patent Document 1 mentions that 34 mg/g dry cell of ergothioneine was obtained only when the mycelium of *Pleurotus citrinopileatus* was cultured in two culture periods for a total of 28 days in a culture medium supplemented with a high concentration of amino acids. These observations suggest that the transformed filamentous fungus of the present invention can produce high amounts of ergothioneine in a simple manner and in a short period of time by using the common culture method for filamentous fungi.

Also, as can be seen from FIG. 2, a comparison with the control strain suggests that the AsEgtA transformant can produce ergothioneine efficiently and at high purity. This is supported by the results of the measurement of the ergothioneine purity in an ergothioneine extract obtained from the AsEgtA transformant. Similarly, it was also found that each of the (AsEgtA+AsEgtB) transformant and the (AsEgtA+AsEgtC) transformant can produce ergothioneine efficiently and at high purity.

Example 4: Confirmation of Transformed *Aspergillus sojae*

In a test tube, conidia of each of the fungi shown in Table 8 were inoculated in 10 ml of a DPY liquid medium and the inoculated medium was subjected to shake culture at 30° C. for 3 days. Subsequently, the cells were collected. The collected cells were triturated in a bead cell disrupter (MS-100R; Tomy Digital Biology) under a chilled condition to give triturated cell powder, which in turn was suspended in a 0.1 (w/v) % aqueous SDS solution to form a SDS suspension. To the resulting SDS suspension, a one-quarter volume of sample buffer (Lane Marker Reducing Sample Buffer, ImmunoPure (5×); Thermo Fisher Scientific) was added and the mixture was stirred. The mixture was then subjected to a heat treatment at 98° C. for 3 min. Following the heat treatment, the mixture was centrifuged and the supernatant was collected. The supernatant in an amount equivalent to 0.2 mg cell was then applied to an acrylamide gel and electrophoresed to perform an SDS-PAGE. The results are shown in FIG. 3

As can be seen from FIG. 3, the AsEgtA protein appeared as two bands at approximately 90 kDa in SDS-PAGE while its expected molecular weight estimated from the amino acid sequence was 95.7 kDa. Similarly, the AsEgtB protein appeared as a band at little less than 50 kDa while its expected molecular weight estimated from the amino acid sequence was 56.4 kDa. Also, the AsEgtC protein appeared as a band at 50 kDa while its expected molecular weight estimated from the amino acid sequence was 51.2 kDa.

As can be seen from FIG. 3, the control strain expressed little amount of each of the AsEgtA protein, the AsEgtB protein and the AsEgtC protein whereas the (AsEgtA+AsEgtB) transformant and the (AsEgtA+AsEgtC) transformant expressed the AsEgtA protein and either the AsEgtB protein or the AsEgtC protein. Also, the AsEgtA transfoii-nant, the AsEgtB transformant and the AsEgtC transformant expressed the AsEgtA protein, the AsEgtB protein and the AsEgtC protein, respectively.

Example 5: Preparation of DNA Constructs with Inserted Genes AoEgtA, AoEgtB and AoEgtC (1) Search for Proteins of Interest Using the amino acid sequences of the AsEgtA, AsEgtB and AsEgtC proteins as query sequences, proteins with a high sequence identity were searched from the total protein of *Aspergillus oryzae* RIB 40 strain. DOGAN (http://www-.bio.nite.go.jp/dogan/project/view/AO) was used for the search.

As a result, proteins AO090012000265 (SEQ ID NO: 26), AO090020000619 (SEQ ID NO: 27) and AO090026000291 (SEQ ID NO: 28) were found as proteins having a relatively high sequence identity to the AsEgtA, AsEgtB and AsEgtC proteins, respectively. AO090012000265 is described in Table 2 of Non-Patent Document 5 as a protein similar to Egt1 of *S. pombe*. AO090012000265, AO090020000619 and AO090026000291 had 97%, 99% and 93% sequence identities to the AsEgtA, AsEgtB and AsEgtC proteins, respectively. Genes encoding each of AO090012000265, AO090020000619 and AO090026000291 were identified from the genomic DNA of *Aspergillus oryzae* and named as genes AoEgtA (SEQ ID NO: 23), AoEgtB (SEQ ID NO: 24) and AoEgtC (SEQ ID NO: 25), respectively, meaning egtA, egtB and egtC genes derived from *Aspergillus oryzae*.

(2) Extraction of Chromosomal DNA of *Aspergillus oryzae* RIB40 Strain

The same procedure was followed as in Example 1-(2), except that the conidia of *Aspergillus oryzae* RIB40 strain were used.

(3) Preparation of a Construct Plasmid

The vector fragments prepared in Example 1-(3) were used.

(4) Preparation of a Construct for Inserting a Gene of Interest

The same procedure was followed as in Example 1-(4), except that the genes of interest are the AoEgtA, AoEgtB and AoEgtC genes and the chromosomal DNA of *Aspergillus oryzae* RIB40 strain obtained above was used as a template DNA. Primers used to amplify AoEgtA, AoEgtB and AoEgtC genes and the PCR conditions are shown in Tables 10 to 12 below.

TABLE 10

| | |
|---|---|
| Amplified target region | AoEgtA |
| Forward primer SEQ ID NO: 29 | AoEgtA_1F_Ptef cgcaccaccttcaaaATGTCACCGTTGGCTCTT TCTCC |
| Reverse primer SEQ ID NO: 30 | AoEgtA_2917R_Talp atgtactcctggtacCTAAAGATCCCGCACTAG GCGTG |
| PCR condition | 2 min. at 94° C. (15 sec. at 94° C., 30 sec. at 62° C., 3 min. at 68° C.) × 25 cycles |

TABLE 11

| | |
|---|---|
| Amplified target region | AoEgtB |
| Forward primer SEQ ID NO: 19 | EgtB_1F_Ptef cgcaccaccttcaaaATGTCTAATGTTACCCAA TCAGCCTTGAG |
| Reverse primer SEQ ID NO: 20 | EgtB_1770R_Talp atgtactcctggtacTTAATGTTGACTCCATTC GATCGTGTTCAG |
| PCR condition | 2 min. at 94° C. (15 sec. at 94° C., 30 sec. at 62° C., 2 min. at 68° C.) × 25 cycles |

TABLE 12

| | |
|---|---|
| Amplified target region | AoEgtC |
| Forward primer SEQ ID NO: 31 | AoEgtC_1F_Ptef cgcaccaccttcaaaATGACCACACCCTTCGGA GCC |
| Reverse primer SEQ ID NO: 32 | AoEgtC_1528R_Talp atgtactcctggtacTCAAATCTTCGCAGAAGA AACCCCAACC |
| PCR condition | 2 min. at 94° C. (15 sec. at 94° C., 30 sec. at 62° C., 2 min. at 68° C.) × 25 cycles |

Similar to Examples 1-(4) above, the base sequence of DNA inserted in the extracted plasmid DNA was determined to confirm that DNA constructs in which genes AoEgtA, AoEgtB and AoEgtC had been inserted were obtained.

Example 6: Preparation of Transformed *Aspergillus oryzae*

The same procedure was followed as in Example 2-(1) or (2) above, except that a pyrG-disrupted strain derived from *Aspergillus oryzae* RIB40 strain described in Japanese Unexamined Patent Application Publication No. 2013-034416 was transformed with the DNA constructs in which the genes AoEgtA, AoEgtB and AoEgtC had been inserted.

Example 7: Production of Ergothioneine by Transformed *Aspergillus oryzae*

As shown in Table 13 below, the *Aspergillus oryzae* RIB40 strain to serve as control, the transformed *Aspergillus oryzae* transformed with the gene AoEgtA; and the transformed *Aspergillus oryzae* transformed with the gene AoEgtA and the gene AoEgtB or AoEgtC were compared for their ability to produce ergothioneine in the following manner.

TABLE 13

| Introduced gene | Strain |
|---|---|
| — | Control strain |
| AoEgtA, AoEgtB | (AoEgtA + AoEgtB) Transformant |
| AoEgtA, AoEgtC | (AoEgtA + AoEgtC) Transformant |
| AoEgtA | AoEgtA Transformant |

The same procedure was followed as in Example 3 above, except that the mycelia of the fungi shown in Table 13 were inoculated.

From each of the fungal strains shown in Table 13, the specimens that contained the largest amounts of ergothioneine were selected and were compared for the ergothioneine (EGT) production. The results of the comparison are shown in FIG. 5.

As can be seen from FIG. 5, similar to the transformed *Aspergillus sojae*, the transformed *Aspergillus oryzae* showed increased ergothioneine production as compared to the non-transformed control strain. The ergothioneine production by the (AoEgtA+AoEgtB) transformant and by the (AoEgtA+AoEgtC) transformant was higher than that of the AoEgtA transformant. These results indicate that the transformants of *Aspergillus oryzae* can also achieve efficient production of ergothioneine.

Example 8: Preparation of DNA Constructs with Inserted Gene AnEgtA (1) Search for Proteins of Interest Using the amino acid sequence of the AsEgtA protein of *Aspergillus sojae* as a query sequence, proteins with a high sequence identity were searched from the data base Non-redundant protein sequences (nr). Blastp (http://blast.ncbi.nlm.nih.gov/Blast.cgi?PROGRAM=blastp&PAGE_TYPE=BlastSearch&LINK_LOC=blasthome) was used for the search.

Of the proteins found to have a high sequence identity to the amino acid sequence of the AsEgtA protein, XP_001397117.2 (SEQ ID NO: 34) was found to be a homologous protein of the *Aspergillus niger* CBS 513.88 strain. XP_001397117.2 had a 73% sequence identity to the AsEgtA protein. A gene encoding XP_001397117.2 was identified from the genomic DNA of *Aspergillus niger* and named as a gene AnEgtA (SEQ ID NO: 33), meaning egtA gene derived from *Aspergillus niger*.

(2) Extraction of Chromosomal DNA of *Aspergillus niger* IAM2533 Strain

The same procedure was followed as in Example 1-(2), except that the conidia of *Aspergillus niger* IAM2533 strain were used.

(3) Preparation of a Construct Plasmid

The vector fragments prepared in Example 1-(3) were used.

(4) Preparation of a Construct for Inserting a Gene of Interest

The same procedure was followed as in Example 1-(4) above, except that the gene of interest is the AnEgtA and the chromosomal DNA of *Aspergillus niger* IAM2533 strain obtained above was used as a template DNA. Primers used to amplify AnEgtA gene and the PCR conditions are shown in Table 14 below.

TABLE 14

| | |
|---|---|
| Amplified target region | AnEgtA |
| Forward primer SEQ ID NO: 35 | AnEgtA_1F_Ptef cgcaccaccttcaaaATGTCACCCTTATGTCCG GTCGTCAAG |
| Reverse primer SEQ ID NO: 36 | AnEgtA_2890R_Talp atgtactcctggtacTCAGACATCCCGCACCAG CC |
| PCR condition | 2 min. at 94° C. (15 sec. at 94° C., 30 sec. at 62° C., 3 min. at 68° C.) × 25 cycles |

Similar to Examples 1-(4) above, the base sequence of DNA inserted in the extracted plasmid DNA was determined to confirm that DNA constructs in which the gene AnEgtA had been inserted were obtained.

The sequence of the cloned gene AnEgtA was confirmed and found to match with the sequence of a putative gene (ANI 1 792134) of the *A. niger* CBS 513.88 strain (the corresponding amino acid sequence is XP_001397117.2). The genome information of this gene is disclosed.

Example 9: Preparation of Transformed *Aspergillus sojae* (2)

The same procedure was followed as in Example 2-(1) and (2), except that a DNA construct in which the gene AnEgtA had been inserted was used.

Example 10: Production of Ergothioneine by Transformed *Aspergillus sojae* (2)

The same procedure was followed as in Example 3 above, except that the conidia of the *Aspergillus sojae* NBRC4239 strain to serve as control and a transformed *Aspergillus sojae* transformed with the gene AnEgtA were inoculated.

From each of the fungal strains, the specimens that contained the largest amounts of ergothioneine were selected and were compared for the ergothioneine (EGT) production. The results of the comparison are shown in Table 15.

TABLE 15

| Strain | EGT concentration (mg/ml extract) | Wet cell weight (mg) | Total extract volume (μl) | EGT total amount mg/10 ml cell culture | mg/g wet cell | Estimated with 78% moisture mg/g dry cell |
|---|---|---|---|---|---|---|
| control gene | 0.12 | 593.8 | 1396 | 0.17 | 0.28 | 1.3 |
| AnEgtA transformant | 4.84 | 455.9 | 992 | 4.80 | 10.53 | 47.9 |

As can be seen from Table 15, similar to the transformed *Aspergillus sojae* transformed with the gene AsEgtA, the transformed *Aspergillus sojae* transformed with the gene AnEgtA showed increased ergothioneine production as compared to the non-transformed control strain. These results indicate that the transformed *Aspergillus sojae* transformed with a heterologous gene AnEgtA derived from a different organism of origin can also achieve efficient production of ergothioneine.

Example 11: Preparation of Transformed *E. coli*

The gene sequences of AsEgtA and AsEgtC genes were optimized based on the amino acid sequences of the AsEgtA and AsEgtC proteins in terms of the codon, secondary structure and GC content. The EcoRV recognition sequence (GATATC) and the SpeI recognition sequence (ACTAGT) were attached to the upstream and the downstream of the respective genes to obtain EcEgtA(SEQ ID NO:37) and EcEgtC(SEQ ID NO:38), respectively.

Meanwhile, pUTE120K' was constructed as an expression vector. Specifically, pUTE100K' described in Japanese Unexamined Patent Application Publication No. 06-292584 was digested with NheI and HpaI to remove the lac promoter. Next, the Tac promoter region of pKK223-3 (GE) with the NheI site attached to the 3' end and the EcoRV site attached to the 5' end was PCR amplified and purified. The amplified promoter was digested with NheI and inserted into the site where the lac promoter was originally located in pUTE100K' to construct pUTE120K'.

pUTE120K' was then digested with restriction enzymes EcoRV and SpeI. Subsequently, EcEgtA or EcEgtC was ligated to construct plasmids pUTE120K'-EcEgtA and pUTE120K'-EcEgtC having EcEgtA or EcEgtC inserted therein.

*E. coli* transformed with the construct plasmids were cultured and the plasmids pUTE120K'-EcEgtA and pUTE120K'-EcEgtC were purified. Next, pUTE120K'-EcEgtC was digested with restriction enzymes BamHI and SpeI to excise a fragment containing the gene EcEgtC. This fragment was purified. Meanwhile, pUTE120K'-EcEgtA was digested with restriction enzymes BamHI and NheI and the fragment containing the gene EcEgtC obtained above was inserted to construct a plasmid pUTE120K'-EcEgtA-EcEgtC. This plasmid was used to transform *E. coli* JM109 strain to create a transformed *E. coli*.

When the transformed *E. coli* is cultured at 25° C. for 16 hours in a TY medium (1 (w/v) % Bacto Tryptone, 0.5 (w/v) % Bacto Yeast Extract, 0.5 (w/v) % NaCl, pH 7.0) containing 0.1 mM isopropyl-β-D-thiogalactopyranoside (IPTG), ergothioneine is detected both in the entire culture broth and in the hot water extract of the collected cells.

Example 12: Production of Ergothioneine by Transformed *E. coli* (1)

As shown in Table 16 below, the control *E. coli* in which the expression vector pUTE120K' had been introduced; the transformed *E. coli* transformed with the gene EcEgtA or EcEgtC; and the transformed *E. coli* transformed with the gene EcEgtA and the gene EcEgtC were compared for their ability to produce ergothioneine in the following manner.

TABLE 16

| Introduced gene | Strain |
|---|---|
| pUTE120K' | Control strain |
| EcEgtA | EcEgtA Transformant |
| EcEgtC | EcEgtC Transformant |
| EcEgtA, EcEgtC | (EcEgtA + EcEgtC) Transformant |

In a 19 ml test tube, each of the bacterial strains shown in Table 16 was inoculated into 2.5 ml of a TY medium. The inoculated medium was then seed-cultured at 37° C. for 16 hours while shaken at 180 rpm. In a 19 ml test tube, 0.02 ml of the seed culture broth was inoculated into 2.5 ml of a TY medium containing ampicillin and 0.5 mM IPTG. The inoculated medium was then main-cultured at 25° C. for 24 hours while shaken at 180 rpm. For the main culture, the following three types of TY medium were prepared: an amino acid-free TYmedium (TY-); a TYmedium supplemented with 0.005 (w/v) % histidine, methionine and cysteine (TY+); and a TY medium supplemented with 0.01 (w/v) % histidine, methionine and cysteine.

After the culture period, the culture was centrifuged (12,000 rpm, 4° C., 10 min) and the cells were collected as precipitate. To cells obtained from 1 ml of the culture, 0.5 ml water was added to form a cell suspension. The resulting cell suspension was subjected to a heat treatment at 98° C. for 10 min. Following the heat treatment, the suspension was centrifuged to collect the extracellular fluid as the supernatant, which in turn was filtered through a 0.45 µm filter to obtain an ergothioneine extract.

The resulting ergothioneine extract and the culture supernatant obtained from the culture after the main culture (filtered through 0.45 µm filter) were analyzed by LC-MS using the following conditions:
LC apparatus; Agilent 1100 series (Agilent)
mass spectrometer; QSTAR Elite (AB sciex)
column; COSMOSIL HILIC (4.6×250 mm)
eluent; acetonitrile+0.1% formic acid: water+0.1% formic acid=75:25 (v/v)
flow rate; 250 µl/ml
detection; ESI positive
Injection; 10 µl
temperature; room temperature
quantification method; calibration curve method using ergothioneine sample (Enzo Life Sciences; Cat. No. BML-FR111)

The bacterial strains shown in Table 16 were compared for the ergothioneine (EGT) production. For the (EcEgtA+EcEgtC) transformant, two arbitrarily selected specimens were used.

The results of the comparison are shown in FIG. 6. As can be seen from FIG. 6, no ergothioneine was detected in the control strain or the EcEgtC transformant whether in the culture supernatant or in the ergothioneine extract. This suggests that the control strain and the EcEgtC transformant each have little or no ability to produce ergothioneine.

In comparison, the EcEgtA transformant and the (EcEgtA+EcEgtC) transformant both exhibited an ability to produce ergothioneine. In addition, the amount of ergothioneine produced by the (EcEgtA+EcEgtC) transformant was higher than that of the EcEgtA transformant and the difference between the two transformants was more significant in the culture supernatants. Also, a comparison of the effect of the addition of histidine, methionine and cysteine into the culture medium indicates that the addition of histidine, methionine and cysteine into the culture medium causes an increase in the amount of ergothioneine in each of the EcEgtA transformant and the (EcEgtA+EcEgtC) transformant.

These results indicate that the (EcEgtA+EcEgtC) transformant has an enhanced ergothioneine production capability that is increased multiplicatively, rather than additively, from that of the EcEgtA transformant since the EcEgtA transformant showed high ergothioneine production whereas the EcEgtC transformant showed no production of ergothioneine.

Example 13: Production of Ergothioneine by Transformed *E. coli* (2)

In a 19 ml test tube, each of the bacterial strains shown in Table 16 was inoculated into 2.5 ml of a TY medium (1 (w/v) % Bacto Tryptone, 0.5 (w/v) % Bacto Yeast Extract, 1 (w/v) % NaCl, pH 7.0) containing 50 µg/ml ampicillin. The inoculated medium was then seed-cultured at 37° C. overnight while shaken at 180 rpm. Subsequently, in a 500 ml fluted Erlenmeyer flask, 0.8 ml of the resulting seed culture broth was inoculated into 100 ml of a TY medium containing 0.2 mM IPTG+50 µg/ml ampicillin. The inoculated medium was then main-cultured at 25° C. for 24 hours while shaken at 150 rpm.

After the culture period, the culture was centrifuged (12,000 rpm, 4° C., 10 min) and the cells were collected as precipitate. To cells obtained from 1 ml of the culture, 0.5 ml distilled water was added and the mixture was stirred to form a cell suspension. The resulting cell suspension was subjected to a heat treatment at 98° C. for 10 min. Following the heat treatment, the suspension was centrifuged to collect the extracellular fluid as the supernatant, which in turn was filtered through a 0.45 µm filter to obtain an ergothioneine extract.

The resulting ergothioneine extract and the culture supernatant obtained from the culture after the main culture (filtered through 0.45 µm filter) were analyzed by LC-MS using the conditions described in Example 12 above. Also, the cells obtained from 40 mL of the culture broth were dried in an incubator at 60° C. to measure the dry cell weight. The ergothioneine (EGT) production was compared and the results are shown in Table 17.

TABLE 17

| strain | Ergothioneine extract | | | Culture supernatant | | Dry cell weight | |
|---|---|---|---|---|---|---|---|
| | EGT Conc. (µg/ml extract) | EGT Conc. (µg/ml culture) | EGT Total amount (mg/100 ml culture) | EGT Conc. (µg/ml culture) | EGT Total amount (mg/100 ml culture) | Dry cell weight (g/100 ml culture) | EGT amount (mg/g dry cell) |
| EcEgtA Transformant | 14.1 | 7.05 | 0.71 | 12.4 | 1.24 | 0.14 | 5.04 |
| EcEgtC Transformant | N.D. | N.D. | N.D. | N.D. | N.D. | 0.15 | N.D. |

TABLE 17-continued

|  | Ergothioneine extract | | | Culture supernatant | | Dry cell weight | |
| --- | --- | --- | --- | --- | --- | --- | --- |
| strain | EGT Conc. (μg/ml extract) | EGT Conc. (μg/ml culture) | EGT Total amount (mg/100 ml culture) | EGT Conc. (μg/ml culture) | EGT Total amount (mg/100 ml culture) | Dry cell weight (g/100 ml culture) | EGT amount (mg/g dry cell) |
| (EcEgtA + EcEgtC) Transformant | 16.4 | 8.21 | 0.82 | 39.4 | 3.94 | 0.14 | 5.86 |
| Control strain | N.D. | N.D. | N.D. | N.D. | N.D. | 0.15 | N.D. |

As can be seen from Table 17, similar to Example 12, the control strain and the EcEgtC transformant exhibited little or no ability to produce ergothioneine. Also, the amount of ergothioneine produced by the (EcEgtA+EcEgtC) transformant was higher than that of the EcEgtA transformant and the difference between the two transformants was more significant in the culture supernatants. Further, the (EcEgtA+EcEgtC) transformant has an enhanced ergothioneine production capability that is increased multiplicatively, rather than additively, from that of the EcEgtA transformant.

Example 14: Production of Ergothioneine by Transformed *E. coli* (3)

In a 19 ml test tube, the (EcEgtA+EcEgtC) transformed *E. coli* shown in Table 16 was inoculated into 2.5 ml of a TY medium containing 1 μg/ml ampicillin. The inoculated medium was then seed-cultured at 30° C. for 16 hours while shaken at 140 rpm. Subsequently, in a 3l jar fermenter (B. E. Marubishi), all of the resulting seed culture broth was inoculated into 2000 ml of a medium for high density culture containing 0.1 mM IPTG, 0.1 (w/v) % histidine, 0.1 (w/v) % methionine and 0.6 (w/v) % sodium thiosulfate. The inoculated medium was then main-cultured while controlled to 25° C., 0.01 MPa, 750 rpm.

After the culture period, the culture was centrifuged (12,000 rpm, 4° C., 5 min) and the cells were collected as precipitate. To cells obtained from 1 ml of the culture, 1 ml distilled water was added and the mixture was stirred to form a cell suspension. The resulting cell suspension was subjected to a heat treatment at 100° C. for 15 min. Following the heat treatment, the suspension was centrifuged to collect the extracellular fluid as the supernatant, which in turn was filtered through a 0.45 μm filter to obtain an ergothioneine extract.

The resulting ergothioneine extract and the culture supernatant obtained from the culture after the main culture (filtered through 0.45 μm filter) were analyzed by HPLC using the conditions described in Example 3 above. The cell concentration was analyzed by absorbance (OD 600 nm).

FIG. 7 shows the absorbance (OD600) during the culture period, along with the results of measurement of the amounts of ergothioneine in the ergothioneine extract and in the culture supernatant. As shown in FIG. 7, the amount of ergothioneine in the ergothioneine extract (i.e., intracellular) was 0.64 mg/ml at its highest and the amount of ergothioneine in the culture supernatant (i.e., extracellular) was 0.05 mg/ml at its highest. Also, the cell concentration (OD600) was 47.1 at its highest. These results indicate that the high density culture of the (EcEgtA+EcEgtC) transformed *E. coli* enables production of ergothioneine in higher amounts per culture.

The results of Examples 11 to 14 above indicate that by transforming a host organism with the gene egtA or the genes egtA and egtC that have been optimized for expression in the host organism in terms of their codons, secondary structures and GC contents based on the amino acid sequences of the AsEgtA protein and AsEgtC protein derived from *Aspergillus sojae*, it is possible to achieve production of ergothioneine in the host organism regardless of their inherent ergothioneine production ability.

The results of Examples 11 to 14 also indicate that culturing the ergothioneine-producing transformants in large amounts or at high density can achieve production of ergothioneine in large quantity. These results suggest that the transformed filamentous fungus can also produce ergothioneine on an industrial scale when cultured in large amounts or at high density.

INDUSTRIAL APPLICABILITY

The transformed filamentous fungus of the present invention and the production method thereof can be used to produce ergothioneine at high purity. Accordingly, since ergothioneine is a sulfur-containing amino acid with high anti-oxidative property, the present invention can be used in the industrial-scale production of raw materials used for the production of antioxidative products such as cosmetic products and supplements with imparted antioxidative functions.

SEQUENCE LISTING

The invention claimed is:

1. A transformed filamentous fungus comprising a gene encoding an enzyme (1) or genes encoding enzymes (1) and (2) inserted therein and can overexpress the inserted gene or genes,
wherein the gene encoding the enzyme (1) is a gene having the base sequence set forth in SEQ ID NO: 1, 23 or 33, or the enzyme (1) is an enzyme having the amino acid sequence set forth in SEQ ID NO: 4, 26 or 34, and
wherein the gene encoding the enzyme (2) is a gene having the base sequence set forth in SEQ ID NO: 2, 3, 24 or 25, or the enzyme (2) is the enzyme having the amino acid sequence set forth in SEQ ID NO: 5, 6, 27 or 28, wherein the enzyme (1) catalyzes the reaction in which hercynyl cysteine sulfoxide represented by the following formula (I)

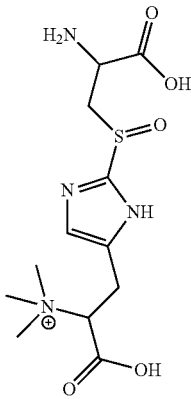

[Formula (I)]

is produced from histidine and cysteine in the presence of S-adenosylmethionine, iron (II), and oxygen; and wherein the enzyme (2) catalyzes the reaction in which ergothioneine is produced from hercynyl cysteine sulfoxide using pyridoxal 5'-phosphate as a coenzyme.

2. The transformed filamentous fungus of claim 1, wherein the filamentous fungus is a microorganism of the genus *Aspergillus*.

3. The transformed filamentous fungus of claim 1, wherein the filamentous fungus is a fungus of the genus *Aspergillus* selected from the group consisting of *Aspergillus sojae*, *Aspergillus oryzae*, *Aspergillus niger*, *Aspergillus tamarii*, *Aspergillus awamori*, *Aspergillus usamii*, *Aspergillus kawachii*, and *Aspergillus saitoi*.

4. The transformed filamentous fungus of claim 1, wherein the transformed filamentous fungus is a transformed filamentous fungus in which the expression of the gene encoding the enzyme (1) or the genes encoding the enzymes (1) and (2) is enhanced such that the amount of ergothioneine is increased compared to a host filamentous fungus.

5. The transformed filamentous fungus of claim 1, wherein the transformed filamentous fungus is a transfmmed filamentous fungus in which the expression of the genes encoding the enzymes (1) and (2) is enhanced such that the amount of ergothioneine is increased compared to transformed filamentous fungi in which the expression of the gene encoding the enzyme (1) is enhanced.

6. The transformed filamentous fungus of claim 1, wherein the transformed filamentous fungus is a transformed filamentous fungus in which the expression of the gene encoding the enzyme (1) or the genes encoding the enzymes (1) and (2) is enhanced such that when the transformed filamentous fungi is cultured at 30° C. for 3 days in a culture medium suitable for the growth of the host filamentous fungus, the amount of ergothioneine is 10.0 mg or more per 1 g of dry cell mass.

7. A method for producing ergothioneine, comprising the step of applying histidine and cysteine to the transfoiined filamentous fungus according to claim 1 to obtain ergothioneine.

8. A method for producing a high-purity-ergothioneine-containing composition, comprising the step of obtaining an ergothioneine-containing composition having purity of 5% or higher from a culture obtained by culturing a transformed filamentous fungus according to claim 1 with the use of a culture medium containing histidine and cysteine.

9. The transformed filamentous fungus of claim 1, wherein the enzyme (1) and/or the enzyme (2) is overexpressed under the control of a high expression promoter selected from the group consisting of a promoter region of translation elongation factor TEF1 gene (tef1), a promoter region of α-amylase gene (amy), and a promoter region of alkaline protease gene (alp).

\* \* \* \* \*

SEQUENCE LISTING

<160> NUMBER OF SEQ ID NOS: 38

<210> SEQ ID NO 1
<211> LENGTH: 2925
<212> TYPE: DNA
<213> ORGANISM: Aspergillus sojae

<400> SEQUENCE: 1

```
atgtcacctt tggctctctc tcctaagacc gttgacattg tcaacatctt tcagaatgat      60
gtggagttct ccctcgtaaa tgagatccat aagggtatta gtcctcccgc tggcgttagg     120
aagtcaatgc caacgatgct tctttacgat gccaatggcc tcaagctttt tgagaacatc     180
acctatgtga aggagtatta tctaacaaat gcggaaattg aggtcttgga gacaaattcc     240
aggaggatag ttgaacggat tccagacaat gcgcaactgc ttgaattagg tagcgggtgc     300
gtcatccttc caaatcaaat cgtaaccttt caggctgcgt agcgtatcat taccgttctc     360
cggttttaac cgccttttag gaatcttcgg aaaattgaga ttctgctacg ggagtttgag     420
cgcgtgggaa agcgcgtgga ttattatgcc ctggacctgt ctctatcaga actgcagcgc     480
acattcgcag aggtgtccat tgatgattac acacacgttg gcctccatgg tctccatgga     540
acctacgatg atgccgtcac ttggcttaac agccccgaaa acaggaagcg gcccacggtg     600
atcatgtcta tgggttcctc tttagggaac tttgaccgtc ccggcgcagc aaagtttctc     660
tcgcagtatg ctagccttct tggtccatcc gatatgatga tcattggtct ggatggctgc     720
aaggacccgg gcaaagtata cagggcatac aatgattcag aaggtgttac acggcagttc     780
tacgagaacg gactagtgca tgcaaatgtt gttcttggat acgaagcctt caaatctgat     840
gagtgggaag tagtgactga ctacgatacc gtggagggac gacactgggc agcctactca     900
cccaagaagg acgtcactat caacggggtc cttcttaaga agggtgagaa acttttcttt     960
gaagaggcgt acaagtacgg accagaggaa cgcgatcaac tgtggcgtga tgccaagtta    1020
attcagtcta cggaaatggg caatgggtct gacgattacc gtgagtagca atggctgcc    1080
tcatttcaat agacgtgtat gctgactctg gcttttcgca aaatagatct ccatcttctg    1140
acatcggcta ccctcaacct ccccacgtct ccctctcaat atgcagctca tcctataccc    1200
agctttgaag aatggcagtc cctgtggaca gcatgggata tgctacaaa ggctatggtc    1260
cctcgcgagg agcttctgtc aaagccgatc aagctacgga actctttgat cttctatctg    1320
ggacacattc ctacattctt gggttagtct acatggctta ctattcccaa cacatagctt    1380
gatgctaatt atgcaaacag acatccatct gacccgagcc ctgcgcggaa aattaacaga    1440
gccaaagtct tataaactaa ttttcgaacg tgggattgat cctgatgtag atgaccccga    1500
gaagtgccac tcccatagcg agatcccaga cgagtggcca gctcttgatg acattctaga    1560
ctaccaagag cgagtcagaa gcagagttag atccatctac caaatcgagg ccttgcagaa    1620
gaacagaatc ctgggtgagg cgctttggat tggatttgag cacgaagtga tgcacctcga    1680
gacattcctg tacatgttga tccagagcga aaggatactt cccccgcccg ccactgagcg    1740
gccggacttc aaaaaactgt atcaagaagc tcggagaagc atgaaagcaa atgagtggtt    1800
ctctgttcct gaacagacac ttactattgg ccttgatggt gctgatacca acgacgtacc    1860
cccaacgacc tatgggtggg acaatgagaa acctgcgaga acagtcacgg ttccagcatt    1920
tgaggcgcag gcaggcccca tcaccaatgg tgagtacgcc aagtacttgc aagcgaatca    1980
gtcgcgcaga aggccagcat catgggtcct gacccattcg gatgaagact acgccatacc    2040
tatggcggtc aacggaagca gtgtcggggc tacgcaggac tttatgtcca actttgctgt    2100
ccgtacggtc ttcggcccag ttccacttga atttgctcag gactggcctg tgatggcgtc    2160
atatgatgaa ttagctgaat acgccgaatg ggtgggttgc aggatcccaa ccttcgaaga    2220
gacaaggagt atctatctgc actcagcgct attgaaggaa agaggtggcg tgaatcataa    2280
tggggagccc aacggccata ggttagtgca gcctcattat aacaccacat tcggattaa    2340
gctgagctaa cggctgtcag tttgaacggc gatctgaatg gggtgaatgg aaatggttac    2400
```

```
tcgaagatca acccaggcaa acctcgtaag ccggatcacc agcctgtaca atatccttcc    2460
cgagacgccc tgccagtgtt ccttgatctg cacggtctca acgtcgggtt caagcactgg    2520
caccccaccc cagttatcca gaacggcgat cgactcgccg gtcagggtga actgggaggc    2580
gcatgggagt ggactagcac gccattagcg ccacacgatg gctttaaagc catggagatc    2640
tacccgggat acacctgtaa gtaccagtcc cgttatcggg taccctctaa aagtctatca    2700
ttacatacta attccgcaca gccgatttct tcgacggtaa acataatatc atcctgggtg    2760
gttcttgggc tactcatccc cgcgtcgctg ggcgtaccac tttgtaagtt taccggtata    2820
gaactcgggg cactataaga tgctgacatc acctctagcg tcaattggta ccagcacaac    2880
tatccttaca cctgggcagg agcacgcctg gtgcgggatc tttag                    2925

<210> SEQ ID NO 2
<211> LENGTH: 1770
<212> TYPE: DNA
<213> ORGANISM: Aspergillus sojae

<400> SEQUENCE: 2
atgtctaatg ttacccaatc agccttgaga caggcaactc gcgcctacgc tcgccgactg      60
ccatcgacgc agcatggctc cttcgcttcc gcccttccca gacgggcgct cgccactcca     120
tacagacggt tctatgtctc cgaaactaag gctggaaatg ctcaggtttc ggtagatacc     180
gctatgaagc aggagcagaa ggaattcatg aaacaaactg gggtgcagcc gcagaaggtg     240
gagctcccta gttctggtgt ttccggcgat gcctcgatga gcccgtctgc cggcatcctc     300
aagcaggcca ctgtcatgga ccaaggaacg cgaccgatct atctcgatat gcaggccaca     360
accccaacgg atccccgtgt tctcgacgcc atgctcccct tcttgaccgg aatttacggc     420
aaccctcatt cgagaaccca tgcatacggt tgggagtcag aaaaggcagt cgagcaatcc     480
cgagagcata tcgccaagct gatcggcgcg gacccgaaag agatcatctt cactagcggt     540
gctactgaga gtaacaacat gagcattaag ggtgtggcga ggttttttgg gcgctccggc     600
aaaaaaaacc acatcatcac aacgcagacc gagcacaagt gtgttcttga cagctgtcgg     660
catcttcagg atgagggcta cgaggttacg tatctccccg tgcagaacaa cggcttgatt     720
cggatggaag acctcgaggc cgccattcgc cctgaaacgg ccctggtcag catcatggcc     780
gtcaacaatg agatcggtgt tatccagccc ctggaacaga ttggaaagtt gtgccgctcc     840
aagaagattt tcttccacac ggacgctgca caggccgtgg aaagatcccg ttggatgtgg     900
aataaattga atattgattt gatgtctatt tcgagccaca agatttacgg ccccaagggt     960
attggagctt gctatgtcag acgtcgtccc agggttcgcc ttgaccctct cattactgga    1020
ggtgacagag ccgaggcctg gcgcagtggt actcttgctc ctcatctggt cgttgggttc    1080
ggtgaggcct gccggatcgc cgcccaagat atggaggtac gttctatttt tcttttgttt    1140
ctgcttactt gcaatcccct ttctatttc cgatgattat atactgcaaa tatggatttc    1200
cgagaccggt gggggtagct gcacgcctaa gcgtgaccc atgggcctat gacgtctcag    1260
caggggtgat gagttgacta ttgctttgtt tgccttgttt gcctcatgcg gctatgcgtc    1320
agtggacatc gctaatcgag ttggcagtat gacaccaagc acattgatcg tttgtccaag    1380
cgcctgaccg acgggctcct atccatggag cacacacacc tcaacggaga ccctgaacat    1440
cactacccgg gatgtgtcaa tgtctccttt gcctacatcg aaggagagtc tctcctgatg    1500
gccttgaaag acattgctct gtcgtcgggt agtgcctgta cctctgcgtc attggagccc    1560
```

```
agctacgtcc ttcgtgcctt gggtagcagt gacgagagcg cccatagcag tatccggttt    1620
ggaattggac gattcacttc ggatagcgaa attgactacg tgctgaaggc ggtacaggac    1680
cgcgttcatt tcctacgcga gctgagcccc ttgtgggaat tggtgcagga aggtatcgac    1740
ctgaacacga tcgaatggag tcaacattaa                                    1770
```

<210> SEQ ID NO 3
<211> LENGTH: 1529
<212> TYPE: DNA
<213> ORGANISM: Aspergillus sojae

<400> SEQUENCE: 3

```
atgaccactc ccttcggagc tcccatgaga gagcacttcc tctttgacac caacttcaaa     60
aacctcaacc atggtatagt atcctactcc agtaacaagt accaacatta gctaactata    120
aaccaggctc cttcggcaca taccccgtg ccgtccagac agtcctccgc caacaccaac     180
actccgccga ggcccgtcca gacctcttct accgcatcac ccgcggccaa ggcatcgacg    240
gatcgcgccg catcgtagcc aacctgctca catccccgt caacgaatgt gtcttcgtca     300
agaacgcaac cacggggggtc gccaccgtgc tccgtaatct agtcttccag aagggagacg    360
cagtcgtgta cttcgacact atctatggcg ctgtggagaa gaatgtacac tctattatgg    420
aggctagtcc tgtgactact cgaaaggttg agtgtgcgtt acccgttagc catgaggacc    480
tggtgaaacg gttcagggat gtcgtgagtc gtgcaagagg ggaagggctg catgtgaaag    540
ttgcggtgtt tgacaccatc gtcagtgtgc ctggggtcag gttcccgttc gagaccttgg    600 tagggtctg tcgggaggag ggtatactca gtcttatcga tggggcgcat ggtattggac     660
atataccgtt ggatttgggg actttgaggc cggatttctt tactagtaac ctgcataagt    720
atgttccttt cccctttctt tctttctttc gtttgattac tgtgtgagga tcttgtatgc    780
tgatatagag caaaaaaaaa agatggctat tcgtccccg cggctgcgca gttctccacg     840
tcccactccg caaccaacat ctcatccgca ccacattccc aacctcatgg ggatacatcc     900
cccctccctc atccggggag ataacccca ccgccacgca gggtaaatcc gccttcgaat      960
atctcttcga acacatctcc acaaccgacg acacgccctg gctatgcgtc cccgccgcca    1020
tgaaattccg aactgaagtc tgcggcggcg aagaccgcat ctacgcttac ctggagaccc    1080
tagcccgcga ggccggggat atcgttgccc gcgccctcgg gacggaagtc atgcaggagc    1140 ccggggttgaa ggagggagag gtgagtcagc ttaggaggtg tgggatggct actgtgcggt    1200
tgccgattgc tgtgacttct tcttcttctt ctgattctgg gtctggtaat ggtggggtg     1260 ctgttatgag ggtgcagggt gaggatggga gttcgtattt gcgaatccag acgtctttgg    1320
tggggactgt gagtaattgg tttcgggata cgttgtttga taagtacgag acgtttgtgc    1380
cggtgttcca gcatgggggg tggttgtgga cgagactcag tgcgcaggtt tatttggaga    1440 aggggggattt tgagtggttg gggggtgttt tgagggagtg ttgtgagagg gttgagaggg    1500
aggttggggt tcttctgcg aagctttga                                       1529
```

<210> SEQ ID NO 4
<211> LENGTH: 845
<212> TYPE: PRT
<213> ORGANISM: Aspergillus sojae

<400> SEQUENCE: 4

```
Met Ser Pro Leu Ala Leu Ser Pro Lys Thr Val Asp Ile Val Asn Ile
1               5                   10                  15
```

```
Phe Gln Asn Asp Val Glu Phe Ser Leu Val Asn Glu Ile His Lys Gly
             20                  25                  30

Ile Ser Pro Pro Ala Gly Val Arg Lys Ser Met Pro Thr Met Leu Leu
             35                  40                  45

Tyr Asp Ala Asn Gly Leu Lys Leu Phe Glu Asn Ile Thr Tyr Val Lys
         50                  55                  60

Glu Tyr Tyr Leu Thr Asn Ala Glu Ile Glu Val Leu Glu Thr Asn Ser
65                  70                  75                  80

Arg Arg Ile Val Glu Arg Ile Pro Asp Asn Ala Gln Leu Leu Glu Leu
                 85                  90                  95

Gly Ser Gly Asn Leu Arg Lys Ile Glu Ile Leu Leu Arg Glu Phe Glu
                100                 105                 110

Arg Val Gly Lys Arg Val Asp Tyr Tyr Ala Leu Asp Leu Ser Leu Ser
            115                 120                 125

Glu Leu Gln Arg Thr Phe Ala Glu Val Ser Ile Asp Tyr Thr His
        130                 135                 140

Val Gly Leu His Gly Leu His Gly Thr Tyr Asp Asp Ala Val Thr Trp
145                 150                 155                 160

Leu Asn Ser Pro Glu Asn Arg Lys Arg Pro Thr Val Ile Met Ser Met
                165                 170                 175

Gly Ser Ser Leu Gly Asn Phe Asp Arg Pro Gly Ala Ala Lys Phe Leu
                180                 185                 190

Ser Gln Tyr Ala Ser Leu Leu Gly Pro Ser Asp Met Met Ile Ile Gly
            195                 200                 205

Leu Asp Gly Cys Lys Asp Pro Gly Lys Val Tyr Arg Ala Tyr Asn Asp
210                 215                 220

Ser Glu Gly Val Thr Arg Gln Phe Tyr Glu Asn Gly Leu Val His Ala
225                 230                 235                 240

Asn Val Val Leu Gly Tyr Glu Ala Phe Lys Ser Asp Glu Trp Glu Val
            245                 250                 255

Val Thr Asp Tyr Asp Thr Val Glu Gly Arg His Trp Ala Ala Tyr Ser
        260                 265                 270

Pro Lys Lys Asp Val Thr Ile Asn Gly Val Leu Leu Lys Lys Gly Glu
    275                 280                 285

Lys Leu Phe Phe Glu Glu Ala Tyr Lys Tyr Gly Pro Glu Glu Arg Asp
290                 295                 300

Gln Leu Trp Arg Asp Ala Lys Leu Ile Gln Ser Thr Glu Met Gly Asn
305                 310                 315                 320

Gly Ser Asp Asp Tyr His Leu His Leu Leu Thr Ser Ala Thr Leu Asn
            325                 330                 335

Leu Pro Thr Ser Pro Ser Gln Tyr Ala Ala His Pro Ile Pro Ser Phe
        340                 345                 350

Glu Glu Trp Gln Ser Leu Trp Thr Ala Trp Asp Asn Ala Thr Lys Ala
    355                 360                 365

Met Val Pro Arg Glu Glu Leu Leu Ser Lys Pro Ile Lys Leu Arg Asn
370                 375                 380

Ser Leu Ile Phe Tyr Leu Gly His Ile Pro Thr Phe Leu Asp Ile His
385                 390                 395                 400

Leu Thr Arg Ala Leu Arg Gly Lys Leu Thr Pro Lys Ser Tyr Lys
            405                 410                 415

Leu Ile Phe Glu Arg Gly Ile Asp Pro Asp Val Asp Pro Glu Lys
        420                 425                 430

Cys His Ser His Ser Glu Ile Pro Asp Glu Trp Pro Ala Leu Asp Asp
```

```
            435                 440                 445
Ile Leu Asp Tyr Gln Glu Arg Val Arg Ser Arg Val Arg Ser Ile Tyr
450                 455                 460

Gln Ile Glu Gly Leu Ala Glu Asn Arg Ile Leu Gly Glu Ala Leu Trp
465                 470                 475                 480

Ile Gly Phe Glu His Glu Val Met His Leu Glu Thr Phe Leu Tyr Met
                    485                 490                 495

Leu Ile Gln Ser Glu Arg Ile Leu Pro Pro Ala Thr Glu Arg Pro
                500                 505                 510

Asp Phe Lys Lys Leu Tyr Gln Glu Ala Arg Arg Ser Met Lys Ala Asn
                515                 520                 525

Glu Trp Phe Ser Val Pro Glu Gln Thr Leu Thr Ile Gly Leu Asp Gly
                530                 535                 540

Ala Asp Thr Asn Asp Val Pro Pro Thr Thr Tyr Gly Trp Asp Asn Glu
545                 550                 555                 560

Lys Pro Ala Arg Thr Val Thr Val Pro Ala Phe Glu Ala Gln Gly Arg
                    565                 570                 575

Pro Ile Thr Asn Gly Glu Tyr Ala Lys Tyr Leu Gln Ala Asn Gln Ser
                580                 585                 590

Arg Arg Arg Pro Ala Ser Trp Val Leu Thr His Ser Asp Glu Asp Tyr
            595                 600                 605

Ala Ile Pro Met Ala Val Asn Gly Ser Ser Val Gly Ala Thr Gln Asp
            610                 615                 620

Phe Met Ser Asn Phe Ala Val Arg Thr Val Phe Gly Pro Val Pro Leu
625                 630                 635                 640

Glu Phe Ala Gln Asp Trp Pro Val Met Ala Ser Tyr Asp Glu Leu Ala
                    645                 650                 655

Glu Tyr Ala Glu Trp Val Gly Cys Arg Ile Pro Thr Phe Glu Glu Thr
                660                 665                 670

Arg Ser Ile Tyr Leu His Ser Ala Leu Leu Lys Glu Arg Gly Gly Val
            675                 680                 685

Asn His Asn Gly Glu Pro Asn Gly His Ser Leu Asn Gly Asp Leu Asn
            690                 695                 700

Gly Val Asn Gly Asn Gly Tyr Ser Lys Ile Asn Pro Gly Lys Pro Arg
705                 710                 715                 720

Lys Pro Asp His Gln Pro Val Gln Tyr Pro Ser Arg Asp Ala Leu Pro
                    725                 730                 735

Val Phe Leu Asp Leu His Gly Leu Asn Val Gly Phe Lys His Trp His
                    740                 745                 750

Pro Thr Pro Val Ile Gln Asn Gly Asp Arg Leu Ala Gly Gln Gly Glu
            755                 760                 765

Leu Gly Gly Ala Trp Glu Trp Thr Ser Thr Pro Leu Ala Pro His Asp
            770                 775                 780

Gly Phe Lys Ala Met Glu Ile Tyr Pro Gly Tyr Thr Ser Asp Phe Phe
785                 790                 795                 800

Asp Gly Lys His Asn Ile Ile Leu Gly Gly Ser Trp Ala Thr His Pro
                    805                 810                 815

Arg Val Ala Gly Arg Thr Thr Phe Val Asn Trp Tyr Gln His Asn Tyr
                    820                 825                 830

Pro Tyr Thr Trp Ala Gly Ala Arg Leu Val Arg Asp Leu
            835                 840                 845

<210> SEQ ID NO 5
```

```
<211> LENGTH: 512
<212> TYPE: PRT
<213> ORGANISM: Aspergillus sojae

<400> SEQUENCE: 5

Met Ser Asn Val Thr Gln Ser Ala Leu Arg Gln Ala Thr Arg Ala Tyr
1               5                   10                  15

Ala Arg Arg Leu Pro Ser Thr Gln His Gly Ser Phe Ala Ser Ala Leu
            20                  25                  30

Pro Arg Ala Leu Ala Thr Pro Tyr Arg Arg Phe Tyr Val Ser Glu
        35                  40                  45

Thr Lys Ala Gly Asn Ala Gln Val Ser Val Asp Thr Ala Met Lys Gln
50                  55                  60

Glu Gln Lys Glu Phe Met Lys Gln Thr Gly Val Gln Pro Gln Lys Val
65                  70                  75                  80

Glu Leu Pro Ser Ser Gly Val Ser Gly Asp Ala Ser Met Ser Pro Ser
                85                  90                  95

Ala Gly Ile Leu Lys Gln Ala Thr Val Met Asp Gln Gly Thr Arg Pro
            100                 105                 110

Ile Tyr Leu Asp Met Gln Ala Thr Thr Pro Thr Asp Pro Arg Val Leu
        115                 120                 125

Asp Ala Met Leu Pro Phe Leu Thr Gly Ile Tyr Gly Asn Pro His Ser
130                 135                 140

Arg Thr His Ala Tyr Gly Trp Glu Ser Glu Lys Ala Val Glu Gln Ser
145                 150                 155                 160

Arg Glu His Ile Ala Lys Leu Ile Gly Ala Asp Pro Lys Glu Ile Ile
                165                 170                 175

Phe Thr Ser Gly Ala Thr Glu Ser Asn Asn Met Ser Ile Lys Gly Val
            180                 185                 190

Ala Arg Phe Phe Gly Arg Ser Gly Lys Lys Asn His Ile Ile Thr Thr
        195                 200                 205

Gln Thr Glu His Lys Cys Val Leu Asp Ser Cys Arg His Leu Gln Asp
210                 215                 220

Glu Gly Tyr Glu Val Thr Tyr Leu Pro Val Gln Asn Asn Gly Leu Ile
225                 230                 235                 240

Arg Met Glu Asp Leu Glu Ala Ala Ile Arg Pro Glu Thr Ala Leu Val
                245                 250                 255

Ser Ile Met Ala Val Asn Asn Glu Ile Gly Val Ile Gln Pro Leu Glu
            260                 265                 270

Gln Ile Gly Lys Leu Cys Arg Ser Lys Lys Ile Phe Phe His Thr Asp
        275                 280                 285

Ala Ala Gln Ala Val Gly Lys Ile Pro Leu Asp Val Asn Lys Leu Asn
290                 295                 300

Ile Asp Leu Met Ser Ile Ser Ser His Lys Ile Tyr Gly Pro Lys Gly
305                 310                 315                 320

Ile Gly Ala Cys Tyr Val Arg Arg Pro Arg Val Arg Leu Asp Pro
                325                 330                 335

Leu Ile Thr Gly Gly Gly Gln Glu Arg Gly Leu Arg Ser Gly Thr Leu
            340                 345                 350

Ala Pro His Leu Val Val Gly Phe Gly Glu Ala Cys Arg Ile Ala Ala
        355                 360                 365

Gln Asp Met Glu Tyr Asp Thr Lys His Ile Asp Arg Leu Ser Lys Arg
370                 375                 380

Leu Thr Asp Gly Leu Leu Ser Met Glu His Thr His Leu Asn Gly Asp
```

```
            385                 390                 395                 400
Pro Glu His His Tyr Pro Gly Cys Val Asn Val Ser Phe Ala Tyr Ile
                    405                 410                 415

Glu Gly Glu Ser Leu Leu Met Ala Leu Lys Asp Ile Ala Leu Ser Ser
                420                 425                 430

Gly Ser Ala Cys Thr Ser Ala Ser Leu Glu Pro Ser Tyr Val Leu Arg
            435                 440                 445

Ala Leu Gly Ser Ser Asp Glu Ser Ala His Ser Ser Ile Arg Phe Gly
        450                 455                 460

Ile Gly Arg Phe Thr Ser Asp Ser Glu Ile Asp Tyr Val Leu Lys Ala
465                 470                 475                 480

Val Gln Asp Arg Val His Phe Leu Arg Glu Leu Ser Pro Leu Trp Glu
                485                 490                 495

Leu Val Gln Glu Gly Ile Asp Leu Asn Thr Ile Glu Trp Ser Gln His
            500                 505                 510

<210> SEQ ID NO 6
<211> LENGTH: 463
<212> TYPE: PRT
<213> ORGANISM: Aspergillus sojae

<400> SEQUENCE: 6

Met Thr Thr Pro Phe Gly Ala Pro Met Arg Glu His Phe Leu Phe Asp
1               5                   10                  15

Thr Asn Phe Lys Asn Leu Asn His Gly Ser Phe Gly Thr Tyr Pro Arg
                20                  25                  30

Ala Val Gln Thr Val Leu Arg Gln His Gln His Ser Ala Glu Ala Arg
            35                  40                  45

Pro Asp Leu Phe Tyr Arg Ile Thr Arg Gly Gln Gly Ile Asp Gly Ser
        50                  55                  60

Arg Arg Ile Val Ala Asn Leu Leu Asn Ile Pro Val Asn Glu Cys Val
65                  70                  75                  80

Phe Val Lys Asn Ala Thr Thr Gly Val Ala Thr Val Leu Arg Asn Leu
                85                  90                  95

Val Phe Gln Lys Gly Asp Ala Val Val Tyr Phe Asp Thr Ile Tyr Gly
            100                 105                 110

Ala Val Glu Lys Asn Val His Ser Ile Met Glu Ala Ser Pro Val Thr
        115                 120                 125

Thr Arg Lys Val Glu Cys Ala Leu Pro Val Ser His Glu Asp Leu Val
    130                 135                 140

Lys Arg Phe Arg Asp Val Val Ser Arg Ala Arg Gly Glu Gly Leu His
145                 150                 155                 160

Val Lys Val Ala Val Phe Asp Thr Ile Val Ser Val Pro Gly Val Arg
                165                 170                 175

Phe Pro Phe Glu Thr Leu Val Gly Val Cys Arg Glu Glu Gly Ile Leu
            180                 185                 190

Ser Leu Ile Asp Gly Ala His Gly Ile Gly His Ile Pro Leu Asp Leu
        195                 200                 205

Gly Thr Leu Arg Pro Asp Phe Phe Thr Ser Asn Leu His Lys Trp Leu
    210                 215                 220

Phe Val Pro Arg Gly Cys Ala Val Leu His Val Pro Leu Arg Asn Gln
225                 230                 235                 240

His Leu Ile Arg Thr Thr Phe Pro Thr Ser Trp Gly Tyr Ile Pro Pro
                245                 250                 255
```

Pro Ser Ser Gly Glu Ile Thr Pro Thr Ala Thr Gln Gly Lys Ser Ala
            260                 265                 270

Phe Glu Tyr Leu Phe Glu His Ile Ser Thr Thr Asp Asp Thr Pro Trp
        275                 280                 285

Leu Cys Val Pro Ala Ala Met Lys Phe Arg Thr Glu Val Cys Gly Gly
    290                 295                 300

Glu Asp Arg Ile Tyr Ala Tyr Leu Glu Thr Leu Ala Arg Glu Ala Gly
305                 310                 315                 320

Asp Ile Val Ala Arg Ala Leu Gly Thr Glu Val Met Gln Glu Pro Gly
                325                 330                 335

Leu Lys Glu Gly Glu Val Ser Gln Leu Arg Arg Cys Gly Met Ala Thr
            340                 345                 350

Val Arg Leu Pro Ile Ala Val Thr Ser Ser Ser Ser Asp Ser Gly
        355                 360                 365

Ser Gly Asn Gly Gly Gly Ala Val Met Arg Val Gln Gly Glu Asp Gly
    370                 375                 380

Ser Ser Tyr Leu Arg Ile Gln Thr Ser Leu Val Gly Thr Val Ser Asn
385                 390                 395                 400

Trp Phe Arg Asp Thr Leu Phe Asp Lys Tyr Glu Thr Phe Val Pro Val
                405                 410                 415

Phe Gln His Gly Gly Trp Leu Trp Thr Arg Leu Ser Ala Gln Val Tyr
            420                 425                 430

Leu Glu Lys Gly Asp Phe Glu Trp Leu Gly Gly Val Leu Arg Glu Cys
        435                 440                 445

Cys Glu Arg Val Glu Arg Glu Val Gly Val Ser Ser Ala Lys Leu
    450                 455                 460

<210> SEQ ID NO 7
<211> LENGTH: 748
<212> TYPE: DNA
<213> ORGANISM: Aspergillus sojae

<400> SEQUENCE: 7
tgtggaccag acaggcgcca ctcggccggg ccacaactgc ttgggttttg accgggagcg    60
gaccaattaa ggactcgaac gaccgcgggg ttcaaatgca aacaagtaca acacgcagca   120
aacgaagcag cccaccactg cgttgatgcc cagtttgtct gtccgaaatc caccggaaag   180
gtggaaacat actatgtaac aatcagaggg aagaaaaatt ttttatcgac gaggcaggat   240
agtgactgat ggtggggtca tggtcgggtc tccgagcgaa agagaaccaa ggaaacaaga   300
tcaacgaggt tggtgtaccc aaaaggccgc agcaacaaga gtcatcgccc aaaagtcaac   360
agtctggaag agactccgcc gtgcagattc tgcgtcggtc ccgcacatgc gtggtggggg   420
cattacccct ccatgtccaa tgataagggc ggcggtcgag ggcttaagcc cgcccactaa   480
ttcgccttct cgcttgcccc tccatataag gattcccctc cttcccctcc acaactttt    540 ttcctctttc tctcttcgtc cgcatcagta cgtatatctt tcccccctac ctctttctca   600
ctcttcctcg attcattcca ctcttctcct tactgacatc tgttttgctc agtacctcta   660
cgcgatcagc cgtagtatct gagcaagctt ttttacagaa tctttctagt atcttacaaa   720
gaactacaaa gttcgcacca ccttcaaa                                      748

<210> SEQ ID NO 8
<211> LENGTH: 800
<212> TYPE: DNA
<213> ORGANISM: Aspergillus sojae

<400> SEQUENCE: 8

```
gtaccaggag tacattggag agttctacca ttgttgctgg aatacaatga tgattagaaa        60
ccgaagagtg ttatgattcg gacggatata cgcatggcac gcatacagcg tgatacatag       120
gctgtttgct caagaattag gattttatct gaatccatgt acagagttta cttatgttag       180
tagtcaatga aatcttggct ttctaatttt gtccgatcta caaggggtag tcgatcacag       240
aacgaactag atgtgcaggg aacgatgatc acccgctctt agcaagacct ctagtagttt       300
tcgaccatag ctttaacgcg aatcatgacc ctactatttt ctagattgca gaccaagtca       360
catgacaatg tcctctttga agtaggatca gtagctgatt agattccggg aaatgaatta       420
gggctggcgt tccaactact ggggagtgcc gatgttgctg tatgaaagat agtaagatta       480
ctagtgcaca gctgtagtaa ttatttactc tagattatat attccaaata ataagtaatc       540
taagatagta gacagtccta tgatatagct ccgggttcga agtcggcaaa agatatgcaa       600
tcacctgtcg ggatgatata tgtatatctg aaataccgac atcaaccatc cagtcggatc       660
agctaaacga agtatcactt ctttcgccac tgccaataca tacttctatt aaagttcatg       720
ttacagtata agccacaaga cttatctcca gaactaactt gtgcatagga gctctgccga       780
tagccgggtg gttggatcgg                                                    800
```

<210> SEQ ID NO 9
<211> LENGTH: 1838
<212> TYPE: DNA
<213> ORGANISM: Aspergillus sojae

<400> SEQUENCE: 9

```
ttgggcttat tgctatgtcc ctgaaaggat atcaaaagca ggcaaaaagc caggcataac        60
cccgcgcgga tggtacccta aggataagcc ctaatcttat ctacatgtga ctgcgtcgat       120
gtgtttggtc caaatgaggc atgtggctca ccccacaggc ggagaaacgt gtggctagtg       180
catgacggtc ccctccatag attcaattta attttttcgcg gcaattgtcg tgcagtttgt       240
atctaccgtt cattctacat attaagggtt agtaattgga catcctgatt actttgtcta       300
attactgaaa actcgaagta ctaacctact aaataagtca gtttcaacca ctaagtactc       360
atttatacaa tagttgcaga accccgcgct acccctccat tgccaacatg tcttccaagt       420
cgcaattgac ctacagcgca cgcgctagca agcaccccaa tgcgctcgtg aagaagctct       480
tcgaggttgc cgaggccaag aaaaccaatg tcaccgtttc cgccgacgtg acaaccacca       540
aagagctgct ggatttggct gaccgtatgc gcaccgggga tgccacttac atatgatcta       600
gtaatggtta atggtggaat atataacagg actcggtccg tacattgccg tgatcaaaac       660
tcacatcgat atcctctccg atttcagcga agagaccatc atcggtctga aggcccttgc       720
agagaagcac aatttcctca tcttcgaaga tcgcaagttc atcgatatcg gaaacacagt       780
ccaaaagcag taccatggcg gcactctgcg catctctgag tgggcccaca tcatcaactg       840
cagtattctg cccggtgagg gtatcgtcga ggctctggcc cagactgctt cggccgagga       900
cttcccctat ggctctgaga ggggcctttt gatccttgcg gagatgacat ccaagggatc       960
tttggctacc ggtcaatata ctacttcttc tgttgactat gcccggaagt ataagaagtt      1020
tgtgatggga ttcgtctcga cgcgtcacct gggcgaggtt cagtctgaag ttagctcgcc      1080
ttcggaggag gaggatttcg tcgtcttcac gacaggtgtc aacctctcct cgaagggaga      1140
caaactggga cagcaatacc agactcctga gtctgctgtt ggacgcggtg ccgactttat      1200
cattgctggt cgtggaattt atgctgctcc tgatcccgtg gaggcagcga agcggtacca      1260
```

```
gaaagaggga tgggatgcat accagaagcg tgttggtgcg caataagtag tggtgaatac    1320
gtgctctttt tatggcagta tatcgcaagt atgatgcgat tcataaattc agcagtcgaa    1380
ttctacgaga gaacgatgct aagagatacc ctctctatat gaataatatg cctgcctcga    1440
gatatggaca tattcaagat cagagttaag ggtcatgttt caaaatcaca ccaatctcca    1500
acatagacga gaattttttac cggattgtct gaaggtgcag ctggagattg gtctattttc    1560
taagagtggg gtatcactaa tgtacagtcg gtcactatcg tacaaacaat cacaattata    1620
tacaagattt cccatcaccc cttactctaa catggcactt ttatccatcg agtccgagcc    1680
tagccaccat ttggtgcttt cgtagagacc aaagtataac cctgatccga cagcggccat    1740
aaacgtgttg atagcacacc ctcggaatag tcctctcggg ccatctgttc gtataatctc    1800
ccgtacggta ttgatcatcc ttttcttctg aggtgcgg                              1838
```

<210> SEQ ID NO 10
<211> LENGTH: 38
<212> TYPE: DNA
<213> ORGANISM: Artificial sequence
<220> FEATURE:
<223> OTHER INFORMATION: Primer

<400> SEQUENCE: 10

```
cggtacccgg ggatctgtgg accagacagg cgccactc                              38
```

<210> SEQ ID NO 11
<211> LENGTH: 40
<212> TYPE: DNA
<213> ORGANISM: Artificial sequence
<220> FEATURE:
<223> OTHER INFORMATION: Primer

<400> SEQUENCE: 11

```
atgtactcct ggtactttga aggtggtgcg aactttgtag                            40
```

<210> SEQ ID NO 12
<211> LENGTH: 28
<212> TYPE: DNA
<213> ORGANISM: Artificial sequence
<220> FEATURE:
<223> OTHER INFORMATION: Primer

<400> SEQUENCE: 12

```
gtaccaggag tacattggag agttctac                                         28
```

<210> SEQ ID NO 13
<211> LENGTH: 23
<212> TYPE: DNA
<213> ORGANISM: Artificial sequence
<220> FEATURE:
<223> OTHER INFORMATION: Primer

<400> SEQUENCE: 13

```
ccgatccaac cacccggcta tcg                                              23
```

<210> SEQ ID NO 14
<211> LENGTH: 43
<212> TYPE: DNA
<213> ORGANISM: Artificial sequence
<220> FEATURE:
<223> OTHER INFORMATION: Primer

<400> SEQUENCE: 14
gggtggttgg atcggttggg cttattgcta tgtccctgaa agg        43

<210> SEQ ID NO 15
<211> LENGTH: 39
<212> TYPE: DNA
<213> ORGANISM: Artificial sequence
<220> FEATURE:
<223> OTHER INFORMATION: Primer

<400> SEQUENCE: 15
cgactctaga ggatcccgca cctcagaaga aaaggatga        39

<210> SEQ ID NO 16
<211> LENGTH: 25
<212> TYPE: DNA
<213> ORGANISM: Artificial sequence
<220> FEATURE:
<223> OTHER INFORMATION: Primer

<400> SEQUENCE: 16
tttgaaggtg gtgcgaactt tgtag        25

<210> SEQ ID NO 17
<211> LENGTH: 38
<212> TYPE: DNA
<213> ORGANISM: Artificial sequence
<220> FEATURE:
<223> OTHER INFORMATION: Primer

<400> SEQUENCE: 17
cgcaccacct tcaaaatgtc acctttggct ctctctcc        38

<210> SEQ ID NO 18
<211> LENGTH: 37
<212> TYPE: DNA
<213> ORGANISM: Artificial sequence
<220> FEATURE:
<223> OTHER INFORMATION: Primer

<400> SEQUENCE: 18
atgtactcct ggtacctaaa gatcccgcac caggcgt        37

<210> SEQ ID NO 19
<211> LENGTH: 44
<212> TYPE: DNA
<213> ORGANISM: Artificial sequence
<220> FEATURE:
<223> OTHER INFORMATION: Primer

<400> SEQUENCE: 19
cgcaccacct tcaaaatgtc taatgttacc caatcagcct tgag        44

<210> SEQ ID NO 20
<211> LENGTH: 45
<212> TYPE: DNA
<213> ORGANISM: Artificial sequence
<220> FEATURE:
<223> OTHER INFORMATION: Primer

<400> SEQUENCE: 20
atgtactcct ggtacttaat gttgactcca ttcgatcgtg ttcag        45

<210> SEQ ID NO 21
<211> LENGTH: 36
<212> TYPE: DNA
<213> ORGANISM: Artificial sequence

```
<220> FEATURE:
<223> OTHER INFORMATION: Primer

<400> SEQUENCE: 21
cgcaccacct tcaaaatgac cactcccttc ggagct                                36

<210> SEQ ID NO 22
<211> LENGTH: 43
<212> TYPE: DNA
<213> ORGANISM: Artificial sequence
<220> FEATURE:
<223> OTHER INFORMATION: Primer

<400> SEQUENCE: 22
atgtactcct ggtactcaaa gcttcgcaga agaaacccca acc                        43

<210> SEQ ID NO 23
<211> LENGTH: 2917
<212> TYPE: DNA
<213> ORGANISM: Aspergillus oryzae

<400> SEQUENCE: 23
atgtcaccgt tggctctttc tcctaagacc gttgacattg tcaacatctt tcagaatgac       60
gtggagttct ccctcgtaaa tgagatccat aagggcatta gtcctcccgc tggcgttagg      120
aagtcaatgc caacgatgct tctttacgat gccaatggcc tcaagctttt tgagaaaatc      180
acctatgtga aggagtatta tctaacaaat gcggaaatcg aggtcttgga gacaaattcc      240
aggaggatag ttgaacggat tccagacaat gcgcaactgc ttgaattagg tagcgggtgc      300
gtcatccttc caaatcaaat cgtaaccttt caggctgcgt agcgtatcat taccgttctc      360
cggttttaac cgccttttag gaatcttcgg aaaattgaga ttctgctacg ggagtttgag      420
cgcgtgggaa agcgcgtgga ttattatgcc cttgacctgt ctctatcaga actgcagcgc      480
acattcgcag aggtgtccat tgatgattac acacacgttg gcctccatgg tctccatgga      540
acctacgacg atgccgtcac ttggcttaac agccccgaaa acaggaagcg gcccacggtg      600
atcatgtcta tggttcctc tttagggaac tttgaccgtc ctggcgcagc aaagtttctc      660
tcgcagtatg ctagccttct tggtccatcc gatatgatga tcattggtct ggatggctgc      720
aaggacccgg gcaaagtata cagggcatac aatgattcag aaggtgttac acggcagttc      780
tatgagaacg gactagtgca tgcaaatgtt gttcttggat acgaagcctt caaacctgat      840
gagtgggaag tagtgactga ctacgatgcc gtggagggac gacactgggc agcctactca      900
cccaggaggg acgtcactat caacgggtc cttcttaaga agggggagaa actcttctt       960 gaagaggcgt acaagtacgg accagaggaa cgcgatcaac tgtggcgtga tgccaagtta     1020
ctccagtcta cggaagtggg caatgggtct gacgattacc gtgagtagca atggctgcc     1080 tcatttcagt agacgtgtat gctaaatctg gcttttcgca aaatagatct ccatcttctg     1140
acatccgctg ccctcaacct ccccacgtct ccctctcaat atgcagctca tcctataccc     1200
agctttgaag aatggcagtc cctgtggaca gcatgggata atgctacaaa ggctatggtc     1260
cctcgcgagg agcttctgtc aaagccgatc aagctacgga actctttaat cttctatctg     1320
gggcacattc ctacattctt gggttagtct acatggctta ctattcccaa cacataactt     1380
gatgctaatt atgcaaacag acatccatct gacccgagcc ctgcgcggaa aactgacaga     1440
gccaaagtct tataaactaa ttttcgaacg tgggattgat cctgatgtag atgaccccca     1500
gaagtgccac tcccatagcg agatcccaga cgagtggcca gctcttgatg acattctaga     1560
```

```
ctaccaagag cgagtcagaa gcagagttag atccatctac cagatcgagg gccttgcaga    1620
aaacagaatc ctgggtgagg cgctttggat tggatttgag cacgaagtga tgcacctcga    1680
gacattcctg tacatgttga tccagagcga aaggatactt ccccgcccg ccactgaacg     1740 gccggacttc aaaaaactgt accaagacgc tcggagaagc atgaaaacaa atgagtggtt    1800
ctccgttcct gaacagacac ttactattgg ccttgatggt gctgatacca acgacgtacc    1860
cccaacgacc tatgggtggg acaatgagaa acctgcgaga acagtgacgg ttccagcatt    1920
tgaggcgcag ggcaggccca tcaccaatgg tgagtacgcc aagtacttgc aagcgaatca    1980
gtcgcgcaga aggccagcat catgggtcct gacccattcg gatgaaaact accccatacc    2040
tatggccgtc aacggaagca gtgtcgggc tacgcaggac tttatgtcca actttgctgt     2100
ccgtactgtc ttcggcccag ttccacttga atttgctcag gactggcctg tgatggcgtc    2160
atatgatgaa ttagccgaat atgccgaatg ggtgggttgc agaatcccaa ccttcgaaga    2220
gacaaggagt atctatctgc actcagcgct actgaaggaa agaggtggcg taaatcataa    2280
tggggagccc aatggccata ggttagtgca gcctcattat aacgccacat tccggggatt    2340
gagctgagct aacggctttc agtgtgaacg gctatctgaa cgggatgaat ggaaatagct    2400
actcgaagat caacccaggc aaacctcgta cgccggacca ccagcctgta caatatcctt    2460
cccgggacgc cttgccagtg ttccttgatc tggacggtct caacgtcggg ttcaagcact    2520
ggcaccccac cccagttatc cagaacgcg atcgactcgc cggtcagggt gaactgggag     2580
gcgcatggga gtggactagc acgccattag cgccacacga tggctttaaa gccatggaga    2640
tctacccggg atacacctgt aagtaccagt cccgttatcg ggtaccctct cattacatac    2700
taattccgca cagccgattt cttcgacggt aaacataaca tcatcctggg tggttcttgg    2760
gctactcatc cccgcgttgc tgggcgtacc actttgtaag tttaccggta tagaacccgg    2820
ggcactataa gatgctgaca acacctctag cgtcaattgg taccagcaca actatcctta    2880
cacctgggca ggagcacgcc tagtgcggga tctttag                             2917
```

<210> SEQ ID NO 24
<211> LENGTH: 1769
<212> TYPE: DNA
<213> ORGANISM: Aspergillus oryzae

<400> SEQUENCE: 24

```
atgtctaatg ttacccaatc agccttgaga caggcaactc gcgcctacgc tcgtcgactg    60
ccatcgacgc agcatggctc cttcgcttcc gcccttccca gacgggcgct cgccactccg    120
tacagacggt tctatgtctc cgaaaccaag gctggaaatg ctcaggtttc ggtagatacc    180
gctattaagc aggagcagaa ggaattcatg aagcaaactg gggtgcagcc gcagaaggtg    240
gagctcccta gttctggtgt tccggcgat gcctcgatga gcccgtctgc cggcatcctc     300
aagcaggcca ctgtcatgga ccaaggaacg cgaccgatct atctcgatat gcaggccaca    360
accccaacgg accccgtgt tctagacgca atgctcccct tcttgaccgg aatttacggc     420
aaccctcact cgagaaccca tgcatacggt tgggagtcag aaaaggcagt cgagcaatcc    480
cgagagcaca tcgccaagct gatcggcgcg acccgaaag agatcatctt cactagcggt     540
gctactgaga gtaacaacat gagcattaag ggtgtggcga ggtttttgg tcgctccggc     600 aaaaagaacc acatcatcac aacgcagacc gagcacaagt gtgttcttga cagctgtcgg    660
catcttcagg atgagggcta cgaggttacg tatctccccg tgcagaacaa cggcttgatt    720
cggatggaag acctcgaggc cgccattcgc cctgaaacgg ccctggtcag catcatggcc    780
```

```
gtcaacaacg agatcggtgt tatccagccc ctggaacaga ttggaaagtt gtgccgctcc    840
aagaagattt tcttccacac ggacgctgca caggccgtgg gaaagattcc gttggatgtg    900
aataaattga atattgatct gatgtctatt tcgagccaca agatttacgg ccccaagggt    960
attggagctt gctatgtcag acgtcgtccc agggttcgcc ttgaccctct cattactgga   1020
ggtggacagg agcgaggcct gcgcagtggt acccttgctc ctcatctggt cgttgggttc   1080
ggtgaggcct gccgtatcgc cgcccaagat atggaggtac gttctatttt tcttttgttt   1140
tctgcttact tgcaatctct tttttatttc cgatgattat atactgcaaa cttgatttcc   1200
gagatcagtg ggagtagctg cacgcctaac gcgtgaccca tcggcctatg acgtctcagc   1260
aggggtgatg agttgactat tgctttgttt gccctgtttg cctcatgcgg ctatgcgtca   1320
gtggacatcg ctaatagaat tgacagtatg acaccaagca cattgatcgt ttgtccaagc   1380
gcctgaccga cgggctccta tccatggagc acccacct caacggagac cctgaacatc     1440
actacccggg atgtgtcaat gtctcctttg cctacatcga aggagagtct cttctgatgg   1500
ccctgaaaga cattgctctg tcgtcgggta gtgcctgtac ctctgcgtca ctggagccca   1560
gctacgtcct tcgtgccttg ggtagcagtg acgagcgc ccatagcagt atccgatttg      1620
gaattggacg attcacttcg gatagcgaga tcgactacgt actgaaggcg gtacaggacc   1680
gcgttcattt cctacgcgag ctgagccccc tgtgggagtt ggtgcaggaa ggtatcgatc   1740
tgaacacgat cgaatggagt caacattaa                                    1769

<210> SEQ ID NO 25
<211> LENGTH: 1528
<212> TYPE: DNA
<213> ORGANISM: Aspergillus oryzae

<400> SEQUENCE: 25
atgaccacac ccttcggagc ccccatgaga gagcacttcc tcttcgacac caagttcaaa     60
aacctcaacc atggtataac tcaaccttac aagtaacaag tacaaacacc aactaactat    120
aatccaggct ccttcggcac ataccccgc gccgtccaaa cagccctccg ccaacaccaa     180
cactcggcgg aggcccgtcc agacctcttc taccgcatca cccgcggcca aggcatcgac    240
gaatcgcgcc gcatcgtagc caacctgctc aacatccccg tcaacgaatg cgtctttgtc    300
aagaacgcaa ccacgggtgt cgccaccgtg ctccgtaatc tagtcttcca aagggagac    360 acagtcgtct acttcgacac gatctatggc gccgtggaga agaatgtaca ctctattatg    420
gagtccagcc ccgtgactac ccggaaggtt gagtatgcgt tgcctgttag ccatgaggac    480
ctggtgaaac ggttccagga tgtcgtgagt cgtgcaaggg gtgaggggct gaatgtgaag    540
gtcgcggtgt tcgacaccat cgtcagtatg cctggtgtac ggttcccgtt tgaggccttg    600
gtagaggtct gtcgggagga gggcatactc agtcttgttg atgggcaca tggtattggc     660 cacataccgt tggatttggg gcttttgaga ccggatttct ttactagtaa tctgcataag   720
tatgtcccct ccttctttcc ttctttcctc cgtttgatta ctatgtggga atacagtttt    780
gggatgctga tatggaacca aaaaagatg gctattcgtc cccgcggct gcgcagtcct      840 ccacgtccca ctccgcaacc aacatctcat ccgcaccaca ttcccaacct catggggata    900
catcccccct ccctcatccg gggagataac ccccaccacc acgcagggta aatccgcctt    960
cgaataccct tcgaatacac tctccacaac cgacgacacg ccctggctct gcgtccccgc   1020
ggccatgaaa ttccgaacgg aagtctgcgc cggcgaagac cgcatctacg cttacctgga   1080
```

```
gaccctagcc cgcgaggccg gggatatcgt tgcccgcgcc ctcgggacgg aagtcatgca   1140
ggaggctggg ctgaaggagg gagaggccag tcagcttagg aggtgtggga tggctactgt   1200
gcggttgccg attgctgtgt cttcttcttc tgatgctggg tctggtcgtg gagggatgc    1260 tgttatgagg gtgcagggtg aggatgggac ttcgtatctg cggattcagg cgtctttggt   1320
ggcgacggtc agtaattggt tcgggatac gttgtttgag aagtatgaga cgtttgtgcc    1380
ggtgtttcag catgggggt ggttgtggac cagactctgt gcgcaggttt atttggagaa    1440
aggggatttt gagtggttgg ggggtgtttt gagggagtgt tgtgagaggg ttgaggggga   1500
ggttggggtt tcttctgcga agatttga                                      1528
```

<210> SEQ ID NO 26
<211> LENGTH: 845
<212> TYPE: PRT
<213> ORGANISM: Aspergillus oryzae

<400> SEQUENCE: 26

```
Met Ser Pro Leu Ala Leu Ser Pro Lys Thr Val Asp Ile Val Asn Ile
1               5                   10                  15

Phe Gln Asn Asp Val Glu Phe Ser Leu Val Asn Glu Ile His Lys Gly
            20                  25                  30

Ile Ser Pro Pro Ala Gly Val Arg Lys Ser Met Pro Thr Met Leu Leu
        35                  40                  45

Tyr Asp Ala Asn Gly Leu Lys Leu Phe Glu Lys Ile Thr Tyr Val Lys
    50                  55                  60

Glu Tyr Tyr Leu Thr Asn Ala Glu Ile Glu Val Leu Glu Thr Asn Ser
65                  70                  75                  80

Arg Arg Ile Val Glu Arg Ile Pro Asp Asn Ala Gln Leu Leu Glu Leu
                85                  90                  95

Gly Ser Gly Asn Leu Arg Lys Ile Glu Ile Leu Leu Arg Glu Phe Glu
            100                 105                 110

Arg Val Gly Lys Arg Val Asp Tyr Tyr Ala Leu Asp Leu Ser Leu Ser
        115                 120                 125

Glu Leu Gln Arg Thr Phe Ala Glu Val Ser Ile Asp Asp Tyr Thr His
    130                 135                 140

Val Gly Leu His Gly Leu His Gly Thr Tyr Asp Asp Ala Val Thr Trp
145                 150                 155                 160

Leu Asn Ser Pro Glu Asn Arg Lys Arg Pro Thr Val Ile Met Ser Met
                165                 170                 175

Gly Ser Ser Leu Gly Asn Phe Asp Arg Pro Gly Ala Ala Lys Phe Leu
            180                 185                 190

Ser Gln Tyr Ala Ser Leu Leu Gly Pro Ser Asp Met Met Ile Ile Gly
        195                 200                 205

Leu Asp Gly Cys Lys Asp Pro Gly Lys Val Tyr Arg Ala Tyr Asn Asp
    210                 215                 220

Ser Glu Gly Val Thr Arg Gln Phe Tyr Glu Asn Gly Leu Val His Ala
225                 230                 235                 240

Asn Val Val Leu Gly Tyr Glu Ala Phe Lys Pro Asp Glu Trp Glu Val
                245                 250                 255

Val Thr Asp Tyr Asp Ala Val Glu Gly Arg His Trp Ala Ala Tyr Ser
            260                 265                 270

Pro Arg Arg Asp Val Thr Ile Asn Gly Val Leu Leu Lys Lys Gly Glu
        275                 280                 285

Lys Leu Phe Phe Glu Glu Ala Tyr Lys Tyr Gly Pro Glu Glu Arg Asp
```

```
            290                 295                 300
Gln Leu Trp Arg Asp Ala Lys Leu Leu Gln Ser Thr Glu Val Gly Asn
305                 310                 315                 320

Gly Ser Asp Asp Tyr His Leu His Leu Leu Thr Ser Ala Ala Leu Asn
                325                 330                 335

Leu Pro Thr Ser Pro Ser Gln Tyr Ala Ala His Pro Ile Pro Ser Phe
                340                 345                 350

Glu Glu Trp Gln Ser Leu Trp Thr Ala Trp Asp Asn Ala Thr Lys Ala
                355                 360                 365

Met Val Pro Arg Glu Glu Leu Leu Ser Lys Pro Ile Lys Leu Arg Asn
                370                 375                 380

Ser Leu Ile Phe Tyr Leu Gly His Ile Pro Thr Phe Leu Asp Ile His
385                 390                 395                 400

Leu Thr Arg Ala Leu Arg Gly Lys Leu Thr Glu Pro Lys Ser Tyr Lys
                405                 410                 415

Leu Ile Phe Glu Arg Gly Ile Asp Pro Asp Val Asp Asp Pro Gln Lys
                420                 425                 430

Cys His Ser His Ser Glu Ile Pro Asp Glu Trp Pro Ala Leu Asp Asp
                435                 440                 445

Ile Leu Asp Tyr Gln Glu Arg Val Arg Ser Arg Val Arg Ser Ile Tyr
                450                 455                 460

Gln Ile Glu Gly Leu Ala Glu Asn Arg Ile Leu Gly Glu Ala Leu Trp
465                 470                 475                 480

Ile Gly Phe Glu His Glu Val Met His Leu Glu Thr Phe Leu Tyr Met
                485                 490                 495

Leu Ile Gln Ser Glu Arg Ile Leu Pro Pro Ala Thr Glu Arg Pro
                500                 505                 510

Asp Phe Lys Lys Leu Tyr Gln Asp Ala Arg Arg Ser Met Lys Thr Asn
                515                 520                 525

Glu Trp Phe Ser Val Pro Glu Gln Thr Leu Thr Ile Gly Leu Asp Gly
                530                 535                 540

Ala Asp Thr Asn Asp Val Pro Pro Thr Thr Tyr Gly Trp Asp Asn Glu
545                 550                 555                 560

Lys Pro Ala Arg Thr Val Thr Val Pro Ala Phe Glu Ala Gln Gly Arg
                565                 570                 575

Pro Ile Thr Asn Gly Glu Tyr Ala Lys Tyr Leu Gln Ala Asn Gln Ser
                580                 585                 590

Arg Arg Arg Pro Ala Ser Trp Val Leu Thr His Ser Asp Glu Asn Tyr
                595                 600                 605

Pro Ile Pro Met Ala Val Asn Gly Ser Ser Val Gly Ala Thr Gln Asp
                610                 615                 620

Phe Met Ser Asn Phe Ala Val Arg Thr Val Phe Gly Pro Val Pro Leu
625                 630                 635                 640

Glu Phe Ala Gln Asp Trp Pro Val Met Ala Ser Tyr Asp Glu Leu Ala
                645                 650                 655

Glu Tyr Ala Glu Trp Val Gly Cys Arg Ile Pro Thr Phe Glu Glu Thr
                660                 665                 670

Arg Ser Ile Tyr Leu His Ser Ala Leu Leu Lys Glu Arg Gly Gly Val
                675                 680                 685

Asn His Asn Gly Glu Pro Asn Gly His Ser Val Asn Gly Tyr Leu Asn
                690                 695                 700

Gly Met Asn Gly Asn Ser Tyr Ser Lys Ile Asn Pro Gly Lys Pro Arg
705                 710                 715                 720
```

```
Thr Pro Asp His Gln Pro Val Gln Tyr Pro Ser Arg Asp Ala Leu Pro
            725                 730                 735

Val Phe Leu Asp Leu Asp Gly Leu Asn Val Gly Phe Lys His Trp His
            740                 745                 750

Pro Thr Pro Val Ile Gln Asn Gly Asp Arg Leu Ala Gly Gln Gly Glu
            755                 760                 765

Leu Gly Gly Ala Trp Glu Trp Thr Ser Thr Pro Leu Ala Pro His Asp
770                 775                 780

Gly Phe Lys Ala Met Glu Ile Tyr Pro Gly Tyr Thr Ser Asp Phe Phe
785                 790                 795                 800

Asp Gly Lys His Asn Ile Ile Leu Gly Gly Ser Trp Ala Thr His Pro
            805                 810                 815

Arg Val Ala Gly Arg Thr Thr Phe Val Asn Trp Tyr Gln His Asn Tyr
            820                 825                 830

Pro Tyr Thr Trp Ala Gly Ala Arg Leu Val Arg Asp Leu
            835                 840                 845

<210> SEQ ID NO 27
<211> LENGTH: 512
<212> TYPE: PRT
<213> ORGANISM: Aspergillus oryzae

<400> SEQUENCE: 27

Met Ser Asn Val Thr Gln Ser Ala Leu Arg Gln Ala Thr Arg Ala Tyr
1               5                   10                  15

Ala Arg Arg Leu Pro Ser Thr Gln His Gly Ser Phe Ala Ser Ala Leu
            20                  25                  30

Pro Arg Arg Ala Leu Ala Thr Pro Tyr Arg Arg Phe Tyr Val Ser Glu
        35                  40                  45

Thr Lys Ala Gly Asn Ala Gln Val Ser Val Asp Thr Ala Ile Lys Gln
    50                  55                  60

Glu Gln Lys Glu Phe Met Lys Gln Thr Gly Val Gln Pro Gln Lys Val
65                  70                  75                  80

Glu Leu Pro Ser Ser Gly Val Ser Gly Asp Ala Ser Met Ser Pro Ser
                85                  90                  95

Ala Gly Ile Leu Lys Gln Ala Thr Val Met Asp Gln Gly Thr Arg Pro
            100                 105                 110

Ile Tyr Leu Asp Met Gln Ala Thr Thr Pro Thr Asp Pro Arg Val Leu
        115                 120                 125

Asp Ala Met Leu Pro Phe Leu Thr Gly Ile Tyr Gly Asn Pro His Ser
    130                 135                 140

Arg Thr His Ala Tyr Gly Trp Glu Ser Glu Lys Ala Val Glu Gln Ser
145                 150                 155                 160

Arg Glu His Ile Ala Lys Leu Ile Gly Ala Asp Pro Lys Glu Ile Ile
                165                 170                 175

Phe Thr Ser Gly Ala Thr Glu Ser Asn Asn Met Ser Ile Lys Gly Val
            180                 185                 190

Ala Arg Phe Phe Gly Arg Ser Gly Lys Lys Asn His Ile Ile Thr Thr
        195                 200                 205

Gln Thr Glu His Lys Cys Val Leu Asp Ser Cys Arg His Leu Gln Asp
    210                 215                 220

Glu Gly Tyr Glu Val Thr Tyr Leu Pro Val Gln Asn Asn Gly Leu Ile
225                 230                 235                 240

Arg Met Glu Asp Leu Glu Ala Ala Ile Arg Pro Glu Thr Ala Leu Val
```

245                 250                 255
Ser Ile Met Ala Val Asn Asn Glu Ile Gly Val Ile Gln Pro Leu Glu
            260                 265                 270

Gln Ile Gly Lys Leu Cys Arg Ser Lys Lys Ile Phe Phe His Thr Asp
        275                 280                 285

Ala Ala Gln Ala Val Gly Lys Ile Pro Leu Asp Val Asn Lys Leu Asn
    290                 295                 300

Ile Asp Leu Met Ser Ile Ser Ser His Lys Ile Tyr Gly Pro Lys Gly
305                 310                 315                 320

Ile Gly Ala Cys Tyr Val Arg Arg Pro Arg Val Arg Leu Asp Pro
                325                 330                 335

Leu Ile Thr Gly Gly Gly Gln Glu Arg Gly Leu Arg Ser Gly Thr Leu
            340                 345                 350

Ala Pro His Leu Val Val Gly Phe Gly Glu Ala Cys Arg Ile Ala Ala
        355                 360                 365

Gln Asp Met Glu Tyr Asp Thr Lys His Ile Asp Arg Leu Ser Lys Arg
    370                 375                 380

Leu Thr Asp Gly Leu Leu Ser Met Glu His Thr His Leu Asn Gly Asp
385                 390                 395                 400

Pro Glu His His Tyr Pro Gly Cys Val Asn Val Ser Phe Ala Tyr Ile
                405                 410                 415

Glu Gly Glu Ser Leu Leu Met Ala Leu Lys Asp Ile Ala Leu Ser Ser
            420                 425                 430

Gly Ser Ala Cys Thr Ser Ala Ser Leu Glu Pro Ser Tyr Val Leu Arg
        435                 440                 445

Ala Leu Gly Ser Ser Asp Glu Ser Ala His Ser Ser Ile Arg Phe Gly
    450                 455                 460

Ile Gly Arg Phe Thr Ser Asp Ser Glu Ile Asp Tyr Val Leu Lys Ala
465                 470                 475                 480

Val Gln Asp Arg Val His Phe Leu Arg Glu Leu Ser Pro Leu Trp Glu
                485                 490                 495

Leu Val Gln Glu Gly Ile Asp Leu Asn Thr Ile Glu Trp Ser Gln His
            500                 505                 510

<210> SEQ ID NO 28
<211> LENGTH: 461
<212> TYPE: PRT
<213> ORGANISM: Aspergillus oryzae

<400> SEQUENCE: 28

Met Thr Thr Pro Phe Gly Ala Pro Met Arg Glu His Phe Leu Phe Asp
1               5                   10                  15

Thr Lys Phe Lys Asn Leu Asn His Gly Ser Phe Gly Thr Tyr Pro Arg
            20                  25                  30

Ala Val Gln Thr Ala Leu Arg Gln His Gln His Ser Ala Glu Ala Arg
        35                  40                  45

Pro Asp Leu Phe Tyr Arg Ile Thr Arg Gly Gln Gly Ile Asp Glu Ser
    50                  55                  60

Arg Arg Ile Val Ala Asn Leu Leu Asn Ile Pro Val Asn Glu Cys Val
65                  70                  75                  80

Phe Val Lys Asn Ala Thr Thr Gly Val Ala Thr Val Leu Arg Asn Leu
                85                  90                  95

Val Phe Gln Lys Gly Asp Thr Val Val Tyr Phe Asp Thr Ile Tyr Gly
            100                 105                 110

```
Ala Val Glu Lys Asn Val His Ser Ile Met Glu Ser Ser Pro Val Thr
            115                 120                 125
Thr Arg Lys Val Glu Tyr Ala Leu Pro Val Ser His Glu Asp Leu Val
        130                 135                 140
Lys Arg Phe Gln Asp Val Val Ser Arg Ala Arg Gly Glu Gly Leu Asn
145                 150                 155                 160
Val Lys Val Ala Val Phe Asp Thr Ile Val Ser Met Pro Gly Val Arg
                165                 170                 175
Phe Pro Phe Glu Ala Leu Val Glu Val Cys Arg Glu Gly Ile Leu
            180                 185                 190
Ser Leu Val Asp Gly Ala His Gly Ile Gly His Ile Pro Leu Asp Leu
        195                 200                 205
Gly Ala Leu Arg Pro Asp Phe Phe Thr Ser Asn Leu His Lys Trp Leu
    210                 215                 220
Phe Val Pro Arg Gly Cys Ala Val Leu His Val Pro Leu Arg Asn Gln
225                 230                 235                 240
His Leu Ile Arg Thr Thr Phe Pro Thr Ser Trp Gly Tyr Ile Pro Pro
                245                 250                 255
Pro Ser Ser Gly Glu Ile Thr Pro Thr Thr Gln Gly Lys Ser Ala
            260                 265                 270
Phe Glu Tyr Leu Phe Glu Tyr Ile Ser Thr Thr Asp Asp Thr Pro Trp
        275                 280                 285
Leu Cys Val Pro Ala Ala Met Lys Phe Arg Thr Glu Val Cys Gly Gly
    290                 295                 300
Glu Asp Arg Ile Tyr Ala Tyr Leu Glu Thr Leu Ala Arg Glu Ala Gly
305                 310                 315                 320
Asp Ile Val Ala Arg Ala Leu Gly Thr Glu Val Met Gln Glu Ala Gly
                325                 330                 335
Leu Lys Glu Gly Glu Ala Ser Gln Leu Arg Arg Cys Gly Met Ala Thr
            340                 345                 350
Val Arg Leu Pro Ile Ala Val Ser Ser Ser Asp Ala Gly Ser Gly
        355                 360                 365
Arg Gly Gly Asp Ala Val Met Arg Val Gln Gly Glu Asp Gly Thr Ser
370                 375                 380
Tyr Leu Arg Ile Gln Ala Ser Leu Val Ala Thr Val Ser Asn Trp Phe
385                 390                 395                 400
Arg Asp Thr Leu Phe Glu Lys Tyr Glu Thr Phe Val Pro Val Phe Gln
                405                 410                 415
His Gly Gly Trp Leu Trp Thr Arg Leu Cys Ala Gln Val Tyr Leu Glu
            420                 425                 430
Lys Gly Asp Phe Glu Trp Leu Gly Gly Val Leu Arg Glu Cys Cys Glu
        435                 440                 445
Arg Val Glu Gly Glu Val Gly Val Ser Ser Ala Lys Ile
    450                 455                 460

<210> SEQ ID NO 29
<211> LENGTH: 38
<212> TYPE: DNA
<213> ORGANISM: Artificial sequence
<220> FEATURE:
<223> OTHER INFORMATION: Primer

<400> SEQUENCE: 29
cgcaccacct tcaaaatgtc accgttggct ctttctcc                            38
```

<210> SEQ ID NO 30
<211> LENGTH: 38
<212> TYPE: DNA
<213> ORGANISM: Artificial sequence
<220> FEATURE:
<223> OTHER INFORMATION: Primer

<400> SEQUENCE: 30

```
atgtactcct ggtacctaaa gatcccgcac taggcgtg                               38
```

<210> SEQ ID NO 31
<211> LENGTH: 36
<212> TYPE: DNA
<213> ORGANISM: Artificial sequence
<220> FEATURE:
<223> OTHER INFORMATION: Primer

<400> SEQUENCE: 31

```
cgcaccacct tcaaaatgac cacacccttc ggagcc                                 36
```

<210> SEQ ID NO 32
<211> LENGTH: 43
<212> TYPE: DNA
<213> ORGANISM: Artificial sequence
<220> FEATURE:
<223> OTHER INFORMATION: Primer

<400> SEQUENCE: 32

```
atgtactcct ggtactcaaa tcttcgcaga agaaacccca acc                         43
```

<210> SEQ ID NO 33
<211> LENGTH: 2890
<212> TYPE: DNA
<213> ORGANISM: Aspergillus niger

<400> SEQUENCE: 33

```
atgtcaccct tatgtccggt cgtcaagggc gttgacatcg tcgatatccg tcaaaatgac     60
gtggagtttt ccctggtaaa tgatatccag cgaggtatag atcctccggc aggaacttgc    120
cgatccatgc ccacaatgct tctttacgat gctcaggggc tcaagctgtt cgaggacatt    180
acgtacctgg aggaatacta tctcacaaat gcggagatta cgttctacg  acacatgcg     240
aagaggattg ttgaacgcat cccggacaat gcgcaattac tggaactagg cagtgggtgc    300
gtcttccttc cgcttggagc atgtatagag tatagggtac agacacggga ttctaacata    360
cggtagcaat ctgcgcaaga ttgagatcct tctccaggaa ttcgaagcag cgagcaaaaa    420
agtggactac tatgccttgg atctgtcgct ctcagagttg gagcgcacat tctcggaagt    480
gtccctcgat caatatcaat atgtcaagct ccacggcctg catggcacgt acgacgacgc    540
cctcacctgg ctagaaaacc ccgcgaatcg aaaggtccca acgtgatca tgtcaatggg    600
ctcgtcgata ggaaatttg atcgtcctgc agcggcaaaa ttcttgtcgc aatttgccag    660
gctcttaggg ccgtcggatt tgatggtgct cggtttggat agttgcacgg actcggataa    720
agtgtacaag gcatacaatg attccaaggg tatcacacgg cagttctacg agaacgggtt    780
gttgcatgcg aacgctgtgc ttggatacga agcattcaaa ctcgatgaat gggatatcgt    840
gacggagtac gataacgtcg aagggcggca ccaggcgttc tacgcgccaa accgggacgt    900
gactataaac ggggtactac ttcagaaagg cgagaagcta attttgagg aggcattcaa    960
atatgatccc gagcagtgcg atcagctctg catgatgcg ggtttaattg aggacgctga   1020
gtttggcaat gagtctgggg attaccgtat gtcatccttt ggcaatgtgc tactctgcat   1080
```

```
gtcatgttgc actgcattgt gtaaaaacat gttacaccag ttgagaccat catactaaca    1140
taatctgtcg agcagttatc cacgtgctct cttcggcttc tctcaacttt tcaacgagac    1200
catcacagta tgcggctcaa tctattccga gctttgagga attccagtca ctgtggacag    1260
catgggacat tgtcaccaag gccatggttc tagagagga acttctttcg aagccaatca    1320
aattgcgcaa tgcattaatc ttctacctcg gtcacatacc tacgtttctc ggtcagtgtt    1380
ctgcttggct atttgtggag tgcaagtata ggggtcagca tattgacaag cgcagatgtt    1440
catttgaccc gagcattggg cgaaaagcca acgcacccca agtcatatcg actcattttc    1500
gaacgcggaa tcgaccccga tgtggatgac cccgaaaagt gccattctca cagcgagatt    1560
ccagacgaat ggcctgccct tggagacatc ttggactacc aagtgcgggt tcgaagtagg    1620
gtgaggtcca tttttcagaa gcataatgtg gctgagaata gggtgcttgg tgaagcactc    1680
tggatcgggt ttgagcatga agccatgcat ctggaaacgt tcctttacat gcttatccag    1740
agtgaaagaa cacttccgcc ccccgccgtt ccgcgcccg attttaggaa gtttttccac    1800
gatgcccggc aagagtcaag accaaacgag tggttttcga ttcccgagaa gacgctttcg    1860
gttggattac atgatgatgg acattcagtt cctcgtgact cttttggctg gacaacgaa     1920 aagcccccaga gaaagataac cgttaaagca ttcgaagctc aagcgcgacc aataacaaat    1980
ggagagtacg cgaagtatct acaggcgaat cagctgcccc agaagccaga gtcctgggtc    2040
ttgatcaagc ccgagacgta cccgacttgc aatggtgtca gtcaagacgg tagctacgct    2100
acgaatgaat tcatggcaca ctttgccgtt cgcactgtgt ttggctccgt cccgctcgag    2160
ctagcccagc actggccggt tatcgcgtcg tacgatgaat tggccaagta tgccaagtgg    2220
gtggactgca ggataccaac cttcgaagag gcaaagagta tctacgcgca tgcagctcgg    2280
ctgaaggaaa ctagccacgg cctgaacggt cacaggtaag cataccgctt ccactagatg    2340
cacaggactt actgtcatag tgaaacgaac ggagtcaacg gcacgaaca tagcgagacc     2400 aacccccctac ggcctcgcac cccggaccac caaccggtac agcacccttc gcaagaatct    2460
ctgccggtgt ttgttgagct cgacaattgc aacgtcggct tcaaacactg cacccctacc    2520
ccggtcatcc agaacggcga ccgactcgcc ggtcatggag agctgggagg cgtctgggag    2580
tggacgagca cggaacttgc accccacgaa gggttcgagg ccatgcaaat ctaccccgga    2640
tatacatgta agcttgctgt gtgagatata tgaacacaag ctaactgaga acagccgact    2700
tcttcgacgg aaaacacaat atcatcctcg gagggtcatg ggcgacgcat ccacggatcg    2760
ccggccgcac taccttgtaa gtccgtatgc aagactagcg ggttcatgag ctaatctgtt    2820
cagtgtcaat tggtaccagc ggaactaccc ataccctgg gctggtgccc ggctggtgcg    2880
ggatgtctga                                                          2890
```

<210> SEQ ID NO 34
<211> LENGTH: 835
<212> TYPE: PRT
<213> ORGANISM: Aspergillus niger

<400> SEQUENCE: 34

```
Met Ser Pro Leu Cys Pro Val Val Lys Gly Val Asp Ile Val Asp Ile
 1               5                  10                  15

Arg Gln Asn Asp Val Glu Phe Ser Leu Val Asn Asp Ile Gln Arg Gly
            20                  25                  30

Ile Asp Pro Pro Ala Gly Thr Cys Arg Ser Met Pro Thr Met Leu Leu
        35                  40                  45
```

```
Tyr Asp Ala Gln Gly Leu Lys Leu Phe Glu Asp Ile Thr Tyr Leu Glu
    50                  55                  60
Glu Tyr Tyr Leu Thr Asn Ala Glu Ile Asp Val Leu Arg Thr His Ala
 65                  70                  75                  80
Lys Arg Ile Val Glu Arg Ile Pro Asp Asn Ala Gln Leu Leu Glu Leu
                 85                  90                  95
Gly Ser Gly Asn Leu Arg Lys Ile Glu Ile Leu Leu Gln Glu Phe Glu
                100                 105                 110
Ala Ala Ser Lys Lys Val Asp Tyr Tyr Ala Leu Asp Leu Ser Leu Ser
            115                 120                 125
Glu Leu Glu Arg Thr Phe Ser Glu Val Ser Leu Asp Gln Tyr Gln Tyr
    130                 135                 140
Val Lys Leu His Gly Leu His Gly Thr Tyr Asp Asp Ala Leu Thr Trp
145                 150                 155                 160
Leu Glu Asn Pro Ala Asn Arg Lys Val Pro Thr Val Ile Met Ser Met
                165                 170                 175
Gly Ser Ser Ile Gly Asn Phe Asp Arg Pro Ala Ala Lys Phe Leu
                180                 185                 190
Ser Gln Phe Ala Arg Leu Leu Gly Pro Ser Asp Leu Met Val Leu Gly
    195                 200                 205
Leu Asp Ser Cys Thr Asp Ser Asp Lys Val Tyr Lys Ala Tyr Asn Asp
    210                 215                 220
Ser Lys Gly Ile Thr Arg Gln Phe Tyr Glu Asn Gly Leu Leu His Ala
225                 230                 235                 240
Asn Ala Val Leu Gly Tyr Glu Ala Phe Lys Leu Asp Glu Trp Asp Ile
                245                 250                 255
Val Thr Glu Tyr Asp Asn Val Glu Gly Arg His Gln Ala Phe Tyr Ala
                260                 265                 270
Pro Asn Arg Asp Val Thr Ile Asn Gly Val Leu Leu Gln Lys Gly Glu
    275                 280                 285
Lys Leu Ile Phe Glu Glu Ala Phe Lys Tyr Asp Pro Glu Gln Cys Asp
    290                 295                 300
Gln Leu Trp His Asp Ala Gly Leu Ile Glu Asp Ala Glu Phe Gly Asn
305                 310                 315                 320
Glu Ser Gly Asp Tyr Leu Ile His Val Leu Ser Ser Ala Ser Leu Asn
                325                 330                 335
Phe Ser Thr Arg Pro Ser Gln Tyr Ala Ala Gln Ser Ile Pro Ser Phe
                340                 345                 350
Glu Glu Phe Gln Ser Leu Trp Thr Ala Trp Asp Ile Val Thr Lys Ala
            355                 360                 365
Met Val Pro Arg Glu Glu Leu Leu Ser Lys Pro Ile Lys Leu Arg Asn
370                 375                 380
Ala Leu Ile Phe Tyr Leu Gly His Ile Pro Thr Phe Leu Asp Val His
385                 390                 395                 400
Leu Thr Arg Ala Leu Gly Glu Lys Pro Thr His Pro Lys Ser Tyr Arg
                405                 410                 415
Leu Ile Phe Glu Arg Gly Ile Asp Pro Asp Val Asp Pro Glu Lys
                420                 425                 430
Cys His Ser His Ser Glu Ile Pro Asp Glu Trp Pro Ala Leu Gly Asp
            435                 440                 445
Ile Leu Asp Tyr Gln Val Arg Val Arg Ser Arg Val Arg Ser Ile Phe
    450                 455                 460
Gln Lys His Asn Val Ala Glu Asn Arg Val Leu Gly Glu Ala Leu Trp
```

```
                465                 470                 475                 480
        Ile Gly Phe Glu His Glu Ala Met His Leu Glu Thr Phe Leu Tyr Met
                            485                 490                 495
        Leu Ile Gln Ser Glu Arg Thr Leu Pro Pro Ala Val Pro Arg Pro
                    500                 505                 510
        Asp Phe Arg Lys Phe Phe His Asp Ala Arg Gln Glu Ser Arg Pro Asn
                        515                 520                 525
        Glu Trp Phe Ser Ile Pro Glu Lys Thr Leu Ser Val Gly Leu His Asp
                    530                 535                 540
        Asp Gly His Ser Val Pro Arg Asp Ser Phe Gly Trp Asp Asn Glu Lys
        545                 550                 555                 560
        Pro Gln Arg Lys Ile Thr Val Lys Ala Phe Glu Ala Gln Ala Arg Pro
                            565                 570                 575
        Ile Thr Asn Gly Glu Tyr Ala Lys Tyr Leu Gln Ala Asn Gln Leu Pro
                        580                 585                 590
        Gln Lys Pro Glu Ser Trp Val Leu Ile Lys Pro Glu Thr Tyr Pro Thr
                    595                 600                 605
        Cys Asn Gly Val Ser Gln Asp Gly Ser Tyr Ala Thr Asn Glu Phe Met
                610                 615                 620
        Ala His Phe Ala Val Arg Thr Val Phe Gly Ser Val Pro Leu Glu Leu
        625                 630                 635                 640
        Ala Gln Asp Trp Pro Val Ile Ala Ser Tyr Asp Glu Leu Ala Lys Tyr
                            645                 650                 655
        Ala Lys Trp Val Asp Cys Arg Ile Pro Thr Phe Glu Glu Ala Lys Ser
                        660                 665                 670
        Ile Tyr Ala His Ala Ala Arg Leu Lys Glu Thr Ser His Gly Leu Asn
                    675                 680                 685
        Gly His Ser Glu Thr Asn Gly Val Asn Gly His Glu His Ser Glu Thr
                690                 695                 700
        Asn Pro Leu Arg Pro Arg Thr Pro Asp His Gln Pro Val Gln His Pro
        705                 710                 715                 720
        Ser Gln Glu Ser Leu Pro Val Phe Val Glu Leu Asp Asn Cys Asn Val
                            725                 730                 735
        Gly Phe Lys His Trp His Pro Thr Pro Val Ile Gln Asn Gly Asp Arg
                        740                 745                 750
        Leu Ala Gly His Gly Glu Leu Gly Gly Val Trp Glu Trp Thr Ser Thr
                    755                 760                 765
        Glu Leu Ala Pro His Glu Gly Phe Glu Ala Met Gln Ile Tyr Pro Gly
                770                 775                 780
        Tyr Thr Ser Asp Phe Phe Asp Gly Lys His Asn Ile Ile Leu Gly Gly
        785                 790                 795                 800
        Ser Trp Ala Thr His Pro Arg Ile Ala Gly Arg Thr Thr Phe Val Asn
                            805                 810                 815
        Trp Tyr Gln Arg Asn Tyr Pro Tyr Pro Trp Ala Gly Ala Arg Leu Val
                        820                 825                 830
        Arg Asp Val
                835

<210> SEQ ID NO 35
<211> LENGTH: 42
<212> TYPE: DNA
<213> ORGANISM: Artificial sequence
<220> FEATURE:
<223> OTHER INFORMATION: Primer
```

<400> SEQUENCE: 35
cgcaccacct tcaaaatgtc acccttatgt ccggtcgtca ag        42

<210> SEQ ID NO 36
<211> LENGTH: 35
<212> TYPE: DNA
<213> ORGANISM: Artificial sequence
<220> FEATURE:
<223> OTHER INFORMATION: Primer

<400> SEQUENCE: 36
atgtactcct ggtactcaga catcccgcac cagcc        35

<210> SEQ ID NO 37
<211> LENGTH: 2550
<212> TYPE: DNA
<213> ORGANISM: Artificial sequence
<220> FEATURE:
<223> OTHER INFORMATION: Synthesized gene

<400> SEQUENCE: 37
gatatcatga gcccgctggc gctgagcccg aagaccgtgg acattgtgaa catttttcag    60
aacgacgtgg agtttagcct ggtgaacgag attcataaag gcatcagccc gccggcgggt   120
gttcgtaaaa gcatgccgac catgctgctg tacgatgcga acggtctgaa gctgttcgaa   180
aacattacct atgtgaaaga gtactatctg accaacgcgg agatcgaagt gctggaaacc   240
aacagccgtc gtatcgttga gcgtattccg gacaacgcgc agctgctgga actgggtagc   300
ggcaacctgc gtaagatcga gattctgctg cgtgagttcg aacgtgtggg caaacgtgtt   360
gattactatg cgctggacct gagcctgagc gaactgcaac gtacctttgc ggaagtgagc   420
attgacgatt acacccacgt tggtctgcac ggcctgcacg gtacctatga cgatgcggtt   480
acctggctga acagcccgga aaaccgtaag cgtccgaccg tgatcatgag catgggcagc   540
agcctgggta acttcgatcg tccgggtgcg gcgaaatttc tgagccaata tgcgagcctg   600
ctgggtccga gcgacatgat gatcattggc ctggatggtt gcaaggaccc gggtaaagtg   660
taccgtgcgt ataacgacag cgaaggcgtt acccgtcaat tctacgagaa cggtctggtg   720
cacgcgaacg tggttctggg ctatgaagcg tttaagagcg atgagtggga agtggttacc   780
gactacgata ccgttgaggg tcgtcactgg cggcgtata gcccgaagaa agacgtgacc   840
attaacggcg ttctgctgaa gaaaggtgaa aagctgttct ttgaggaagc gtacaaatat   900
ggcccggagg aacgtgatca gctgtggcgt gacgcgaagc tgatccaaag caccgagatg   960
ggtaacggca gcgacgatta ccacctgcac ctgctgacca gcgcgaccct gaacctgccg  1020
accagcccga gccagtatgc ggcgcacccg attccgagct cgaggaatg gcaaagcctg  1080
tggaccgcgt gggataacgc gaccaaagcg atggttccgc gtgaggaact gctgagcaag  1140
ccgatcaaac tgcgtaacag cctgatcttc tacctgggtc acattccgac ctttctggac  1200
atccacctga cccgtgcgct gcgtggcaag ctgaccgaac cgaagagcta taaactgatc  1260
tttgagcgtg gcattgaccc ggatgtggac gatccggaaa aatgccacag ccacagcgaa  1320
attccggatg agtggccggc gctggacgac atcctggact accaggagcg tgtgcgtagc  1380
cgtgttcgta gcatctatca aattgaaggt ctggcggaga accgtattct gggcgaagcg  1440
ctgtggatcg gtttcgagca cgaagtgatg cacctggaga cctttctgta catgctgatt  1500
caaagcgaac gtatcctgcc gccgccggcg accgagcgtc cggatttcaa gaaactgtat  1560
caggaagcgc gtcgtagcat gaaggcgaac gaatggggttta gcgttccgga gcaaaccctg  1620

| | |
|---|---|
| accatcggcc tggacggtgc ggataccaac gacgtgccgc cgaccaccta cggttgggac | 1680 |
| aacgaaaaac cggcgcgtac cgttaccgtt ccggcgtttg aagcgcaggg tcgtccgatt | 1740 |
| accaacggcg agtacgcgaa atatctgcag gcgaaccaaa gccgtcgtcg tccggcgagc | 1800 |
| tgggttctga cccacagcga cgaagattac gcgatcccga tggcggtgaa cggcagcagc | 1860 |
| gttggtgcga cccaggactt catgagcaac tttgcggtgc gtaccgtttt cggtccggtt | 1920 |
| ccgctggagt ttgcgcaaga ttggccggtg atggcgagct acgacgagct ggcggaatat | 1980 |
| gcggagtggg tgggctgccg tattccgacc ttcgaggaaa cccgtagcat ctacctgcac | 2040 |
| agcgcgctgc tgaaggaacg tggtggcgtt aaccacaacg gcgagccgaa cggtcacagc | 2100 |
| ctgaacggcg atctgaacgg tgtgaacggt aacggctaca gcaaaatcaa cccgggcaag | 2160 |
| ccgcgtaaac cggaccacca gccggttcaa tatccgagcc gtgatgcgct gccggtgttc | 2220 |
| ctggacctgc acggtctgaa cgttggtttt aaacactggc acccgacccc ggtgattcag | 2280 |
| aacggtgatc gtctggcggg tcaaggtgaa ctgggtggcg cgtgggagtg gaccagcacc | 2340 |
| ccgctggcgc cgcacgacgg cttcaaggcg atggagatct acccgggcta taccagcgat | 2400 |
| ttctttgacg gtaaacacaa catcattctg ggtggcagct gggcgaccca cccgcgtgtg | 2460 |
| gcgggtcgta ccacctttgt taactggtat caacacaatt atccgtacac ctgggcgggt | 2520 |
| gcgcgtctgg ttcgtgacct gtaaactagt | 2550 |

<210> SEQ ID NO 38
<211> LENGTH: 1404
<212> TYPE: DNA
<213> ORGANISM: Artificial sequence
<220> FEATURE:
<223> OTHER INFORMATION: Synthesized gene

<400> SEQUENCE: 38

| | |
|---|---|
| gatatcatga ccacgccgtt tggtgcgccg atgcgtgaac attttctgtt cgataccaac | 60 |
| ttcaaaaacc tgaatcacgg ttccttcggc acgtatccgc gtgcggtcca gaccgtgctg | 120 |
| cgtcagcatc aacactcagc agaagctcgc ccggacctgt tttatcgtat tacccgcggt | 180 |
| caaggcatcg acggttctcg tcgcattgtc gcgaacctgc tgaatatccc ggtgaacgaa | 240 |
| tgcgttttcg tcaaaaatgc caccacgggc gttgcaaccg tcctgcgtaa cctggtgttt | 300 |
| cagaaaggtg atgcagtggt ttatttcgac accatctacg gcgctgtgga gaaaaacgtt | 360 |
| cattctatta tggaagcaag tccggtcacc acgcgcaaag tggaatgtgc tctgccggtt | 420 |
| tctcatgaag atctggtcaa acgttttcgc gacgtcgtga gtcgtgcgcg cggtgaaggc | 480 |
| ctgcacgtga agttgccgt cttcgatacg attgtgtcgg ttccgggcgt tcgttttccg | 540 |
| ttcgaaaccc tggtcggtgt gtgccgcgaa gaaggcattc tgagcctgat cgatggtgcg | 600 |
| catggtattg ccacattcc gctggatctg gtaccctgc gtccggactt tttcacctct | 660 |
| aacctgcata aatggctgtt tgtgccgcgc ggttgtgccg tgctgcatgt tccgctgcgt | 720 |
| aatcagcacc tgatccgcac cacgttcccg accagttggg gttatattcc gccgccgagc | 780 |
| tctggcgaaa ttaccccgac ggcaacccag ggcaaatcgg cttttgaata cctgttcgaa | 840 |
| cacattagca ccacgatga tacgccgtgg ctgtgtgttc cggccgcaat gaaatttcgt | 900 |
| accgaagtgt gtggcggtga agatcgcatc tatgcatacc tggaaacgct ggcacgtgaa | 960 |
| gctggtgaca ttgttgcccg tgcactgggt accgaagtga tgcaggaacc gggtctgaaa | 1020 |
| gaaggcgaag ttagccaact gcgtcgctgc ggtatggcca ccgtgcgtct gccgatcgcc | 1080 |

```
gttaccagtt cctcatcgag cgatagcggt agcggtaatg gcggtggcgc cgtcatgcgt    1140
gtgcagggtg aagacggctc tagttatctg cgcattcaaa cgtccctggt tggcaccgtc    1200
tcaaattggt ttcgcgatac gctgttcgac aaatatgaaa cctttgttcc ggtcttccag    1260
catggtggct ggctgtggac ccgtctgtcc gcacaagtgt acctggaaaa gggtgatttt    1320
gaatggctgg gtggcgttct gcgcgaatgc tgtgaacgtg tggaacgcga agtgggcgtt    1380
tcctcagcta aactgtaaac tagt                                           1404
```